(12) United States Patent
Balasubramanian

(10) Patent No.: US 9,421,208 B2
(45) Date of Patent: Aug. 23, 2016

(54) METHODS FOR THE TREATMENT OF SOLID TUMORS

(71) Applicant: Pharmacyclics LLC, Sunnyvale, CA (US)

(72) Inventor: Sriram Balasubramanian, San Carlos, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 14/450,068

(22) Filed: Aug. 1, 2014

(65) Prior Publication Data

US 2015/0038518 A1 Feb. 5, 2015

Related U.S. Application Data

(60) Provisional application No. 61/861,853, filed on Aug. 2, 2013.

(51) Int. Cl.
*A61K 31/519* (2006.01)
*A61K 31/343* (2006.01)
*A61K 45/06* (2006.01)

(52) U.S. Cl.
CPC ........... *A61K 31/519* (2013.01); *A61K 31/343* (2013.01); *A61K 45/06* (2013.01)

(58) Field of Classification Search
CPC .................................................... A61K 31/519
USPC ........................................................ 549/462
See application file for complete search history.

(56) References Cited

U.S. PATENT DOCUMENTS

| | | | |
|---|---|---|---|
| 4,999,378 A | 3/1991 | Fujii et al. |
| 5,254,731 A | 10/1993 | Zimmer et al. |
| 5,397,787 A | 3/1995 | Buzzetti et al. |
| 5,593,997 A | 1/1997 | Dow et al. |
| 5,972,978 A | 10/1999 | Andersen et al. |
| 6,160,010 A | 12/2000 | Uckun et al. |
| 6,211,197 B1 | 4/2001 | Belley et al. |
| 6,221,900 B1 | 4/2001 | Uckun et al. |
| 6,306,897 B1 | 10/2001 | Uckun et al. |
| 6,326,469 B1 | 12/2001 | Ullrich et al. |
| 6,506,769 B2 | 1/2003 | Snow et al. |
| 6,660,744 B1 | 12/2003 | Hirst et al. |
| 6,753,348 B2 | 6/2004 | Uckun et al. |
| 6,770,639 B2 | 8/2004 | Snow et al. |
| 6,921,763 B2 | 7/2005 | Hirst et al. |
| 6,960,685 B2 | 11/2005 | Watkins et al. |
| 7,138,420 B2 | 11/2006 | Bentzien et al. |
| 7,276,612 B2 | 10/2007 | Verner et al. |
| 7,332,497 B2 | 2/2008 | Hirst et al. |
| 7,420,089 B2 | 9/2008 | Verner et al. |
| 7,482,466 B2 | 1/2009 | Verner et al. |
| 7,514,444 B2 | 4/2009 | Honigberg et al. |
| 7,517,988 B2 | 4/2009 | Verner et al. |
| 7,718,662 B1 | 5/2010 | Chen et al. |
| 7,732,454 B2 | 6/2010 | Verner |
| 7,741,330 B1 | 6/2010 | Chen et al. |
| 7,825,118 B2 | 11/2010 | Honigberg et al. |
| 7,834,054 B2 | 11/2010 | Verner et al. |
| 7,960,396 B2 | 6/2011 | Honigberg et al. |
| 8,008,309 B2 | 8/2011 | Honigberg et al. |
| 8,026,371 B2 | 9/2011 | Verner et al. |
| 8,088,781 B2 | 1/2012 | Honigberg et al. |
| 8,158,786 B2 | 4/2012 | Honigberg et al. |
| 8,232,280 B2 | 7/2012 | Honigberg et al. |
| 8,236,812 B2 | 8/2012 | Honigberg et al. |
| 8,306,897 B2 | 11/2012 | Yolles |
| 8,389,570 B2 | 3/2013 | Verner et al. |
| 8,399,470 B2 | 3/2013 | Honigberg et al. |
| 8,476,284 B2 | 7/2013 | Honigberg et al. |
| 8,497,277 B2 | 7/2013 | Honigberg et al. |
| 8,501,724 B1 | 8/2013 | Chen et al. |
| 8,552,010 B2 | 10/2013 | Honigberg et al. |
| 8,563,563 B2 | 10/2013 | Honigberg et al. |
| 8,603,521 B2 | 12/2013 | Loury et al. |
| 8,658,653 B2 | 2/2014 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,741,908 B2 | 6/2014 | Honigberg et al. |
| 8,748,439 B2 | 6/2014 | Honigberg et al. |
| 8,779,171 B2 | 7/2014 | Verner et al. |
| 8,809,273 B2 | 8/2014 | Honigberg et al. |
| 8,883,435 B2 | 11/2014 | Honigberg et al. |
| 8,940,750 B2 | 1/2015 | Honigberg et al. |
| 8,987,233 B2 | 3/2015 | Pan et al. |
| 9,012,463 B2 | 4/2015 | Chen et al. |
| 9,079,908 B2 | 7/2015 | Honigberg et al. |

(Continued)

FOREIGN PATENT DOCUMENTS

CN 103923084 A 7/2014
DE 2201968 8/1973

(Continued)

OTHER PUBLICATIONS

U.S. Appl. No. 14/188,390, filed Feb. 24, 2014, Buggy et al.
U.S. Appl. No. 14/340,483, filed Jul. 24, 2014, Honigberg et al.
Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).
Advani et al. The BTK inhibitor PCI-32765 is highly active and well tolerated in patients (PTS) with relapsed/refractory B cell malignancies: final results from a phase I study, Ann. Oncol., 22(suppl 4): abstract 153 (2011).
Arnold et al. Pyrrolo[2,3-d]pyrimidines Containing an Extended 5-Substituent as Potent and Selective Inhibitors of lck 1, Bioorg. Med. Chem. Ltrs. 10:2167-2170 (2000).
Banker et al. Modern Pharmaceutics, p. 596 (1996).
Banwell et al. Antiproliferative signalling by 1,25(OH)2D3 in prostate and breast cancer is suppressed by a mechanism involving histone deacetylation. Recent Results Cancer Res.: 164:83-98 (2003).

(Continued)

*Primary Examiner* — Taofiq A. Solola
(74) *Attorney, Agent, or Firm* — Foley Hoag LLP

(57) ABSTRACT

Described herein are combinations of ACK inhibitors and HDAC inhibitors in the treatment of diseases and disorders characterized by the presence or development of solid tumors.

15 Claims, 16 Drawing Sheets

(56) References Cited

U.S. PATENT DOCUMENTS

| | | |
|---|---|---|
| 9,125,889 B2 | 9/2015 | Buggy |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 2002/0016460 A1 | 2/2002 | Snow et al. |
| 2002/0155505 A1 | 10/2002 | Wells et al. |
| 2003/0013125 A1 | 1/2003 | Braisted et al. |
| 2003/0035833 A1 | 2/2003 | He |
| 2003/0040461 A1 | 2/2003 | Mcatee |
| 2003/0125235 A1 | 7/2003 | Foxwell |
| 2004/0053908 A1 | 3/2004 | Funahashi et al. |
| 2004/0077726 A1 | 4/2004 | Watkins et al. |
| 2004/0132825 A1 | 7/2004 | Bacopoulos et al. |
| 2005/0008640 A1 | 1/2005 | Waegell et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0137232 A1 | 6/2005 | Bressi et al. |
| 2005/0196851 A1 | 9/2005 | Uckun |
| 2005/0209255 A1 | 9/2005 | Jimenez et al. |
| 2005/0272755 A1 | 12/2005 | Denis et al. |
| 2006/0079494 A1 | 4/2006 | Santi et al. |
| 2006/0167090 A1 | 7/2006 | Uckun et al. |
| 2006/0178367 A1 | 8/2006 | Currie et al. |
| 2007/0105136 A1 | 5/2007 | Staudt et al. |
| 2007/0281907 A1 | 12/2007 | Watkins |
| 2007/0293499 A1 | 12/2007 | Flynn et al. |
| 2007/0293540 A1 | 12/2007 | Verner et al. |
| 2008/0153877 A1 | 6/2008 | Adimoolam et al. |
| 2009/0105209 A1 | 4/2009 | Dewdney et al. |
| 2009/0186898 A1 | 7/2009 | Dewdney et al. |
| 2009/0312284 A1 | 12/2009 | Arts et al. |
| 2009/0317836 A1 | 12/2009 | Kuhn et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0324050 A1 | 12/2010 | Honigberg et al. |
| 2011/0039840 A1 | 2/2011 | Varasi et al. |
| 2011/0039868 A1 | 2/2011 | Honigberg et al. |
| 2011/0177011 A1 | 7/2011 | Currie et al. |
| 2011/0224235 A1 | 9/2011 | Honigberg et al. |
| 2011/0281322 A1 | 11/2011 | Honigberg et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0252821 A1 | 10/2012 | Honigberg et al. |
| 2012/0252822 A1 | 10/2012 | Honigberg et al. |
| 2012/0277254 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0064880 A1 | 3/2013 | Kloos et al. |
| 2013/0178483 A1 | 7/2013 | Buggy et al. |
| 2013/0195852 A1 | 8/2013 | Buggy et al. |
| 2013/0202611 A1 | 8/2013 | Buggy et al. |
| 2013/0273030 A1 | 10/2013 | Buggy et al. |
| 2013/0310402 A1 | 11/2013 | Buggy et al. |
| 2014/0039186 A1 | 2/2014 | Honigberg et al. |
| 2014/0057862 A1 | 2/2014 | Loury et al. |
| 2014/0057907 A1 | 2/2014 | Honigberg et al. |
| 2014/0128413 A1 | 5/2014 | Honigberg et al. |
| 2014/0128414 A1 | 5/2014 | Honigberg et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194446 A1 | 7/2014 | Buggy et al. |
| 2014/0212485 A1 | 7/2014 | Honigberg et al. |
| 2014/0243355 A1 | 8/2014 | Honigberg et al. |
| 2014/0275125 A1 | 9/2014 | Honigberg et al. |
| 2014/0301976 A1 | 10/2014 | Verner et al. |
| 2014/0378446 A1 | 12/2014 | Chen et al. |
| 2015/0118222 A1 | 4/2015 | Levy et al. |
| 2015/0164854 A1 | 6/2015 | Loury et al. |

FOREIGN PATENT DOCUMENTS

| | | |
|---|---|---|
| EP | 0084236 | 7/1983 |
| EP | 0394440 | 10/1990 |
| EP | 1473039 A1 | 11/2004 |
| EP | 1611088 B1 | 6/2009 |
| JP | 3-215470 | 9/1991 |
| JP | 2008519047 A | 6/2008 |
| JP | 2010514777 A | 5/2010 |
| JP | 2010518811 | 6/2010 |
| JP | 2011516594 A1 | 5/2011 |
| JP | 4934197 | 2/2012 |
| WO | WO-95-05358 | 2/1995 |
| WO | WO-97-28161 | 8/1997 |
| WO | WO-99-54286 | 10/1999 |
| WO | WO-0000823 A1 | 1/2000 |
| WO | WO-00-20371 | 4/2000 |
| WO | WO-00-56737 | 9/2000 |
| WO | WO-01-14331 | 3/2001 |
| WO | WO-01-19829 | 3/2001 |
| WO | WO-01-25238 | 4/2001 |
| WO | WO-01-38322 | 5/2001 |
| WO | WO-01-41754 | 6/2001 |
| WO | WO-01-44258 | 6/2001 |
| WO | WO-02-26703 | 4/2002 |
| WO | WO-02-30879 | 4/2002 |
| WO | WO-02-38797 | 5/2002 |
| WO | WO-02-076986 | 10/2002 |
| WO | WO-02-080926 | 10/2002 |
| WO | WO-03-000187 | 1/2003 |
| WO | WO-03013540 A1 | 2/2003 |
| WO | WO-03046200 A2 | 6/2003 |
| WO | WO-03-070691 | 8/2003 |
| WO | WO-03097645 A1 | 11/2003 |
| WO | WO-2004-013130 | 2/2004 |
| WO | WO-2004074290 A1 | 9/2004 |
| WO | WO-2004-092115 | 10/2004 |
| WO | WO-2004-096253 | 11/2004 |
| WO | WO-2004100868 A3 | 11/2004 |
| WO | WO-2005-005429 | 1/2005 |
| WO | WO-2005000197 A2 | 1/2005 |
| WO | WO-2005-014599 | 2/2005 |
| WO | WO-2005037843 A1 | 4/2005 |
| WO | WO-2004100868 A3 | 7/2005 |
| WO | WO-2005060956 A1 | 7/2005 |
| WO | WO-2005074603 A2 | 8/2005 |
| WO | WO-2005-097770 | 10/2005 |
| WO | WO-2006-036941 | 4/2006 |
| WO | WO-2006036527 A1 | 4/2006 |
| WO | WO-2006-050946 | 5/2006 |
| WO | WO-2006-053121 | 5/2006 |
| WO | WO-2006-099075 | 9/2006 |

(56) References Cited

FOREIGN PATENT DOCUMENTS

| WO | WO-2006124462 A2 | 11/2006 |
|---|---|---|
| WO | WO-2007002325 A1 | 1/2007 |
| WO | WO-2007058832 A2 | 5/2007 |
| WO | WO-2007087088 A2 | 8/2007 |
| WO | WO-2007-136790 | 11/2007 |
| WO | WO-2008-054827 | 5/2008 |
| WO | WO-2008108636 A1 | 9/2008 |
| WO | WO-2008121742 A2 | 10/2008 |
| WO | WO-2009051822 A1 | 4/2009 |
| WO | WO-2009158571 A1 | 12/2009 |
| WO | WO-2010009342 A2 | 1/2010 |
| WO | WO-2010009342 A3 | 5/2010 |
| WO | WO-2010126960 A1 | 11/2010 |
| WO | WO-2011034907 A2 | 3/2011 |
| WO | WO-2011-153514 | 12/2011 |
| WO | WO-2011162515 A2 | 12/2011 |
| WO | WO-2012021444 A1 | 2/2012 |

OTHER PUBLICATIONS

Browning. B cells move to centre stage: novel opportunities for autoimmune disease treatment. Nature Reviews/Drug Discovery 5:564-576 (Jul. 2006).
Brzozowski et al. Derivatives of 2-Mercapobenzenesulphonamide XI. Synthesis and Some Pharmacological Properties of 2-{2-[2-(3,4,5-Trimethoxybenzamido)Ethylthio]Benzenesulphonyl} Guanadines. Acta Poloniae Pharmaceutica-Drug Research 50(4-5):345-352 (1993).
Byrd et al. Entering the era of targeted therapy for chronic lymphocytic leukemia: impact on the practicing clinician, J. Clinical Oncology (Jul. 21, 2014) (pii: JCO.2014.55.8262).
Byrd et al. Targeting BTK with Ibrutinib in relapsed chronic lymphocytic leukemia. NEJM 369(1): 32-42 (Jul. 4, 2013).
Carter et al. Chemotherapy of Cancer, 2nd ed. John Wiley & Sons. N.Y., N.Y. 1981. pp. 362-365.
Chang et al. The Bruton tyrosine kinase inhibitor PCI-32765 ameliorates autoimmune arthritis by inhibition of multiple effector cells. Arthritis Research & Therapy 13:R115 (2011).
Chang et al. PCI-45292, a Novel Btk Inhibitor with Optimized Pharmaceutical Properties, Demonstrates Potent Activities in Rodent Models of Arthritis. ACR/ARHP Scientific Meeting, Nov. 6-11, 2010, Poster #286.
Cohen et al. Structural Bioinformatics-Based Design of Selective, Irreversible Kinase Inhibitors. Science 308:1318-1321 (May 27, 2005).
Czuczman et al. Rituximab in combination with fludarabine chemotherapy in low-grade or follicular lymphoma, J. Clin. Oncol. 23(4):694-704 (Feb. 1, 2005).
De Schepper et al. Inhibition of Histone Deacetylases by chlamydocin Induces Apoptosis and Proteasome-Mediated Degradation of Survivin. The Journal of Pharmacology and Experimental Therapeutics. 304(2):881-888 (2003).
Desiderio. Role of Btk in B cell development and signaling. Curr. Opin. Imm. 9:534-540 (1997).
Fabian et al. A small molecule-kinase interaction map for clinical kinase inhibitors. Nature Biotechnology 23(3): 329-336 (2005).
Fisher et al. Prolonged disease-free survival in Hodgkin's disease with MOPP reinduction after first relapse, Ann. Intern. Med., 90(5):761-763 (1979).
Fowler et al. The Bruton's tyrosine kinase inhibitor ibrutinib (PCI-32765) is active and tolerated in relapsed follicular lymphoma, 54th American Society of Hematology Annual Meeting and Exposition, Atlanta, GA, Abstract 156 (Dec. 8-11, 2012).
Fruman. Xid-like Phenotypes: A B Cell Signalosome Takes Shape. Immunity 13:1-3 (Jul. 2000).
Furumal et al. Potent histone deacetylase inhibitors built from trichostatin A and cyclic tetrapeptide antibiotics including trapoxin. PNAS. Jan. 2, 2001. 98(1):87-92.
Ghia. Ibrutinib: better combined with other drugs? Lancet 15:1043-1044 (2014).
Glassman et al. The value of fluorescence in situ hybridization in the diagnosis and prognosis of chronic lymphocytic leukemia. Cancer Genetics and Cytogenetics 158:88-91 (2005).
Gold. To make antibodies or not: signaling by the B-cell antigen receptor. Trends in Pharmacological Sciences 23(7):316-324 (Jul. 2002).
Hagemeister, F. Rituximab for the treatment of non-Hodgkin's lymphoma and chronic lymphocytic leukaemia, Drugs, 70(3):261-272 (2010).
Herman et al. Bruton tyrosine kinase represents a promising therapeutic target for treatment of chronic lymphocytic leukemia and is effectively targeted by PCI-32765, Blood (Epub Mar. 21, 2011), 117(23):6287-6296 (Jun. 2011).
Hiddeman et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group, Blood (Epub Aug. 25, 2005), 106(12):3725-3732 (Dec. 2005).
Hiddeman et al. Rituximab Plus Chemotherapy in Follicular and Mantle Cell Lymphomas, Seminars in Oncology 30(1)Suppl.2:16-20 (Feb. 2003).
Horwood et al. Bruton's Tyrosine Kinase Is Required for Lipopolysaccharide-induced Tumor Necrosis Factor α Production, J. Exp. Med., 197(12):1603-1611 (Jun. 2003).
http://www.uspto.gov/web/offices/pac/dapp/lpecba.htm#7, last accessed Feb. 16, 2011.
Huhn et al. Rituximab therapy of patients with B-cell chronic lymphocytic leukemia. Blood 98(5):1326-1331 (Sep. 1, 2001).
Iwaki et al. Btk Plays a Crucial Role in the Amplification of FcεRI-mediated Mast Cell Activation by Kit. J. Biol. Chem. 280(48):40261-40270 (Dec. 2, 2005).
Jefferies et al. Bruton's Tyrosine Kinase Is a Toll/Interleukin-1 Receptor Domain-binding Protein That Participates in Nuclear Factor κB Activation by Toll-like Receptor 4, J. Biol. Chem., 278:26258-26264 (2003).
Kawakami et al. Terreic acid, a quinone epoxide inhibitor of Bruton's tyrosine kinase. PNAS USA 96:2227-2232 (1999).
Kelly et al. Histone deacetylase inhibitors: from target to clinical trials. Expert Opin Investig Drugs. Dec; 11(12):1695-713 (2002).
Kuppers. Mechanisms of B-cell lymphoma pathogenesis. Nature Reviews/Cancer 5:251-262 (Apr. 2005).
Kurosaki. Functional dissection of BCR signaling pathways. Curr. Opin. Imm. 12:276-281 (2000).
LaVoie. Design and Synthesis of a Novel Class of Histone Deacetylase Inhibitors. Bioorg. Med. Chem. Ltrs. 11:2847-2850 (2001).
Lichtman. Battling the hematological malignancies: The 200 years' war. The Oncologist 13:126-138 (2008).
Lin et al., Selective Itk inhibitors block T-cell activation and murine lung inflammation, Biochemistry 43:11056-11062 (2004).
Liu et al. Structural Basis for selective inhibition of Src family kinases by PPI. Chemistry and Biology 6:671-678, in particular table 1, p. 671 (1999).
Lou et al. Bruton's tyrosine kinase inhibitors: approaches to potent and selective inhibition, preclinical and clinical evaluation for inflammatory diseases and B cell malignancies. J. Med. Chem. 55:4539-4550 (2012).
Luskov A et al. Modulation of the Fcε Receptor I Signaling by Tyrosine Kinase Inhibitors: Search for Therapeutic Targets of Inflammatory and Allergy Diseases. Curr. Pharmaceutical Design 10:1727-1737 (2004).
Mangla et al. Pleiotropic consequences of Bruton tyrosine kinase deficiency in myeloid lineages lead to poor inflammatory responses. Blood 104(4):1191-1197 (2004).
Marks et al. Histone Deacetylase Inhibitors: Inducers of Differentiation or Apoptosis of Transformed Cells, Journal of the National Cancer Institute. 92(15):1210-1216. Aug. 2, 2000.
Merged Markush Service Search, Jun. 27, 2005.
Mori et al. FR235222, a fungal metabolite, is a novel immunosuppressant that inhibits mammalian histone deacetylase (HDAC). I.

(56) References Cited

OTHER PUBLICATIONS

Taxonomy, fermentation, isolation and biological activities. J Antibiot (Tokyo). Feb; 56(2):72-9 (2003).
Niiro et al. Regulation of B-Cell Fate by Antigen-Receptor Signals. Nature Reviews 2:945-956 (2002).
Oligino et al. Targeting B cells for the treatment of rheumatoid arthritis. Arthirits Res. Ther., 5(Suppl.4):S7-S11 (2002).
Pan et al. Discovery of Selective Irreversible Inhibitors for Bruton's Tyrosine Kinase, ChemMedChem, 2:58-61 (2007).
PCT/US2004/010549 International Search Report dated Dec. 20, 2004.
PCT/US2004/010549 International Preliminary Report on Patentability dated Jul. 15, 2005.
PCT/US2006/49626 International search report mailed Apr. 9, 2008.
PCT/US2006/49626 International Preliminary Report on Patentability Search Report dated Mar. 24, 2009.
PCT/US2011/051470 International Preliminary Report on Patentability dated Mar. 18, 2014.
PCT/US2011/051470 International Search Report dated Apr. 20, 2012.
Peterson et al. Prolonged single-agent versus combination chemotherapy in indolent follicular lymphomas: a study of the cancer and leukemia group, Br. J. Clin. Oncol., 21(1):5-15 (Jan. 1, 2003).
Pollyea et al. A Phase I Dose Escalation Study of the Btk Inhibitor PCI-32765 in Relapsed and Refractory B Cell Non-Hodgkin Lymphoma and Use of a Novel Fluorescent Probe Pharmacodynamic Assay, Poster Abstract #3713, 51st ASH Annual Meeting and Exposition (Dec. 3, 2009).
Ponader et al. The Bruton tyrosine kinase inhibitor PCI-32765 thwarts chronic lymphocytic leukemia cell survival and tissue homing in vitro and in vivo. Blood (Epub Dec. 16, 2011) 119(5):1182-1189 (Feb. 2012).
PRNewswire, Pharmacyclics, Inc. Announces Presentation of Interim Results from Phase I Trial of its First-in-Human Btk Inhibitor PCI-32765, Dec. 7, 2009.
PRNewswire, Update on Preclinical Finding and Development Timeline for PCI-45292, Mar. 2, 2011.
Quek et al. A role for Bruton's tyrosine kinase (Btk) in platelet activation by collagen. Curr. Biol. 8(20):1137-1140 (1998).
Rastetter et al. Rituximab: expanding role in therapy for lymphomas and autoimmune diseases. Ann. Rev. Med 55:477-503 (2004).
Sada et al. Protein-Tyrosine Kinases and Adaptor Proteins in FceRI-Mediated Signaling in Mast Cells. Curr. Mol. Med. 3(1):85-94 (2003).
Schaeffer et al. Tec family kinases in lymphocyte signaling and function. Curr. Opin. Imm. 12:282-288 (2000).
Schnute et al. Bruton's tyrosine kinase (Btk). Anti-Inflammatory Drug Discovery.Ed. J.I. Levin and S. Laufer. (2012), pp. 297-326.
Science Daily Counting tumor cells in blood predicts treatment benefit in prostate cancer. (Jul. 7, 2008), http://www.sciencedaily.com/releases/2008/07/080706083142.htm , last accessed Jul. 23, 2013.
Science Daily Drug shows surprising efficacy as treatment for chronic leukemia, mantle cell lymphoma. (Jun. 19, 2013), http://www.sciencedaily.com/releases/2013/06/130619195217.htm, last accessed Jan. 30, 2014.
SCIENCE IP CAS Search, Mar. 16, 2006.
SCIENCE IP CAS Search, Sep. 5, 2006.
Shaffer et al. Lymphoid malignancies: the dark side of B-cell differentiation, Nature Rev. Immun., 2:920-932 (Dec. 2002).
Shah et al. Ibrutinib for the treatment of mantle cell lymphoma, Expert Rev. Hematol. 7(5):521-531 (2014) (Epub Aug. 27, 2014).
Smith et al. The Tec family of cytoplasmic tyrosine kinases: mammalian Btk, Bmx, Itk, Tec, Txk and homologs in other species, BioEssays, 23:436-446 (2001).
Smolen et al. Therapeutic Strategies for Rheumatoid Arthritis. Nature Reviews 2:473-488 (2003).
Tinmouth et al. Fludarabine in alkylator-resistant follicular non-Hodgkin's lymphoma, Leuk. Lymphoma, 41(1-2):137-145 (2001).

U.S. Appl. No. 10/818,755 Office action mailed Mar. 15, 2007.
U.S. Appl. No. 11/617,645 Final Office Action mailed Oct. 16, 2008.
U.S. Appl. No. 11/617,645 Notice of Allowance mailed Feb. 9, 2009.
U.S. Appl. No. 11/617,645 Office Action mailed Jan. 24, 2008.
U.S. Appl. No. 11/617,645 Office Action mailed May 13, 2008.
U.S. Appl. No. 11/692,870 Final Office Action mailed Aug. 19, 2009.
U.S. Appl. No. 11/692,870 Office Action mailed Jan. 26, 2009.
U.S. Appl. No. 11/834,558 Office Action mailed Feb. 5, 2008.
U.S. Appl. No. 12/356,498 Final Office Action mailed Jul. 8, 2011.
U.S. Appl. No. 12/356,498 Office Action mailed Apr. 14, 2011.
U.S. Appl. No. 12/499,002 Final Office Action mailed Dec. 14, 2012.
U.S. Appl. No. 12/499,002 Final Office Action mailed Oct. 25, 2011.
U.S. Appl. No. 12/499,002 Office Action mailed Jun. 5, 2012.
U.S. Appl. No. 12/499,002 Office Action mailed Mar. 3, 2011.
U.S. Appl. No. 12/499,005 Office Action mailed Feb. 17, 2011.
U.S. Appl. No. 12/499,008 Office Action mailed Jul. 19, 2011.
U.S. Appl. No. 12/499,008 Office Action mailed Mar. 9, 2011.
U.S. Appl. No. 12/727,703 Final Office Action mailed Jul. 19, 2011.
U.S. Appl. No. 12/727,703 Office Action mailed Mar. 3, 2011.
U.S. Appl. No. 12/761,588 Office Action mailed Feb. 20, 2013.
U.S. Appl. No. 12/761,588 Office Action mailed Jul. 24, 2012.
U.S. Appl. No. 12/887,428 Office Action mailed Apr. 20, 2011.
U.S. Appl. No. 12/896,535 Office action mailed Mar. 8, 2011.
U.S. Appl. No. 12/907,759 Final Office Action mailed Nov. 8, 2013.
U.S. Appl. No. 12/907,759 Office Action mailed Aug. 13, 2013.
U.S. Appl. No. 12/907,759 Office Action mailed Dec. 31, 2013.
U.S. Appl. No. 12/907,759 Office Action mailed Jul. 10, 2014.
U.S. Appl. No. 13/011,258 Office Action mailed Nov. 22, 2011.
U.S. Appl. No. 13/153,317 Final Office Action mailed Jan. 23, 2014.
U.S. Appl. No. 13/153,317 Office Action mailed Jul. 29, 2013.
U.S. Appl. No. 13/162,449 Office Action mailed Feb. 9, 2012.
U.S. Appl. No. 13/209,147 Office Action mailed Apr. 18, 2012.
U.S. Appl. No. 13/249,066 Final Office Action mailed May 15, 2013.
U.S. Appl. No. 13/249,066 Office Action mailed Dec. 11, 2013.
U.S. Appl. No. 13/249,066 Office Action mailed Nov. 27, 2012.
U.S. Appl. No. 13/312,606 Final Office Action mailed Apr. 5, 2013.
U.S. Appl. No. 13/312,606 Office Action mailed Sep. 19, 2012.
U.S. Appl. No. 13/328,718 Final Office Action mailed Dec. 27, 2012.
U.S. Appl. No. 13/328,718 Office Action mailed Jul. 3, 2012.
U.S. Appl. No. 13/335,719 Final Office Action mailed Nov. 8, 2013.
U.S. Appl. No. 13/335,719 Office Action mailed Jul. 31, 2013.
U.S. Appl. No. 13/340,409 Final Office Action mailed Nov. 12, 2013.
U.S. Appl. No. 13/340,409 Office Action mailed Jul. 19, 2013.
U.S. Appl. No. 13/340,522 Final Office Action mailed Nov. 1, 2013.
U.S. Appl. No. 13/340,522 Office Action mailed Mar. 13, 2013.
U.S. Appl. No. 13/340,533 Final Office Action mailed Feb. 25, 2013.
U.S. Appl. No. 13/340,556 Office Action mailed Jul. 31, 2013.
U.S. Appl. No. 13/361,726 Office Action mailed Jul. 18, 2013.
U.S. Appl. No. 13/361,733 Office Action mailed Jul. 6, 2012.
U.S. Appl. No. 13/450,158 Office Action mailed Oct. 31, 2013.
U.S. Appl. No. 13/472,292 Office Action mailed Mar. 13, 2013.
U.S. Appl. No. 13/479,053 Office Action mailed Sep. 6, 2013.
U.S. Appl. No. 13/526,161 Final Office Action mailed May 15, 2013.
U.S. Appl. No. 13/526,161 Office Action mailed Aug. 1, 2013.
U.S. Appl. No. 13/526,161 Office Action mailed Nov. 27, 2012.
U.S. Appl. No. 13/526,163 Final Office Action mailed May 15, 2013.
U.S. Appl. No. 13/526,163 Office Action mailed Aug. 2, 2013.
U.S. Appl. No. 13/526,163 Office Action mailed Nov. 28, 2012.
U.S. Appl. No. 13/542,440 Office Action mailed Oct. 31, 2013.
U.S. Appl. No. 13/542,440 Office Action mailed Jan. 7, 2014.
U.S. Appl. No. 13/654,173 Office Action mailed Apr. 7, 2014.
U.S. Appl. No. 13/736,812 Office Action mailed Mar. 18, 2014.
U.S. Appl. No. 13/736,812 Office Action mailed Oct. 10, 2014.
U.S. Appl. No. 13/744,265 Final Action mailed Oct. 23, 2013.

(56) References Cited

OTHER PUBLICATIONS

U.S. Appl. No. 13/744,265 Office action mailed Jun. 10, 2013.
U.S. Appl. No. 13/747,319 Office Action mailed Mar. 20, 2014.
U.S. Appl. No. 13/747,319 Office Action mailed Oct. 10, 2014.
U.S. Appl. No. 13/747,322 Office Action mailed Mar. 20, 2014.
U.S. Appl. No. 13/849,399 Office Action mailed Aug. 4, 2014.
U.S. Appl. No. 13/849,399 Office Action mailed Jul. 23, 2014.
U.S. Appl. No. 13/869,700 Office Action mailed May 16, 2014.
U.S. Appl. No. 13/890,498 Office Action mailed Aug. 19, 2014.
U.S. Appl. No. 14/069,233 Office Action mailed Dec. 18, 2013.
U.S. Appl. No. 14/069,233 Office Action mailed Jul. 22, 2014.
U.S. Appl. No. 14/311,025 Office Action mailed Sep. 30, 2014.
U.S. Appl. No. 14/448,963 Office Action mailed Nov. 12, 2014.
Uckun et al. Bruton's tyrosine kinase as a molecular target in treatment of leukemias and lymphomas as well as inflammatory disorders and autoimmunity. Expert Opinion Ther. Patents 2010, 20(11):1-14.
Uckun et al. BTK as a Mediator of Radiation-Induced Apoptosis in DT-40 Lymphoma B Cells, Science, 273(5278):1096-1100 (1996).
Uckun et al. The Anti-leukemic Bruton's Tyrosine Kinase Inhibitor α-cyano-β-hydroxy-β-mehyl-N-(2,5-dibromophenyl)Propenamide (LFM-A13) Prevents Fatal Thromboembolism. Leuk. Lymphoma 44(9):1569-1577 (2003).
Uckun. Bruton's Tyrosine Kinase (BTK) as a Dual-Function Regulator of Apoptosis. Biochem. Pharmacology 56:683-691 (1998).
Uesato. Novel Histone Deacetylase Inhibitors: N-Hydroxycarboxamides Possessing a Terminal Bicyclic Aryl Group. Bioorg. Med. Chem. Ltrs. 12:1347-1349 (2002).
Vassilev et al. Bruton's Tyrosine Kinase as an Inhibitor of the Fas/CD95 Death-inducing Signaling Complex, J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al., Crystalline Solids, Advanced Drug Delivery Reviews, 48:3-26 (2001).
Wang et al. Targeting BTK with ibrutinib in relapsed or refractory mantel-cell lymphoma. N Engl J Med 369(6):507-516 (Aug. 8, 2013).
Watanabe et al. Synthesis of 4-[1-(substituted phenyl)-2-oxo-pyrrolidin4-yl]methyloxybenzoic acids and related compounds, and their inhibitory capacities toward fatty-acid and sterol biosynthesis. Eur. J. Med. Chem. 29:675-686 (1994).
Witzig et al. Detection of myeloma cells in the peripheral blood by flow cytometry. Cytometry (Communications in Clinical Cytometry), 26:113-120 (1996).
Witzig et al. Lenalidomide oral monotherapy produces durable responses in relapsed or refractory indolent non-Hodgkin's lymphoma, J. Clin. Oncol. (Epub Oct. 5, 2009), 27:5404-5409 (2009).
Wolff. Burger's Medicinal Chemistry and Drug Discovery, 5th Ed. Part 1, pp. 975-977 (1995).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents, J. Pharma. and Exp. Therapeutics, 306(3):1174-1181 (2003).
ACS 2015 (http://www.cancer.org/cancer/non-hodgkinlymphoma/detailedguide/non-hodgkin-lymphoma-types-of-non-hodgkinlymphoma).
Advani, R.H., et al., 2013, "Bruton tyrosine kinase inhibitor Ibrutnib (PCI-32765) ha significant activity in patients with relapsed/refractory B-cell malignancies", Journal of Clinical Oncology, vol. 21, No. 1, pp. 88-94.
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia, Blood (ASH Annual Meeting Abstracts) 110:Abstract 2559 (2007).
Ahn et al. Michael acceptors as a tool for anticancer drug design. Current Pharmaceutical Design 2(3):247-262 (1996).

Apsel at al, Targeted Polypharmacology: Discovery of Dual Inhibitors of Tyrosine and Phosphoinositide Kinases. Nature Chem, Bio., 4(11):691-699 (2008).
Bhalla at al. PCI-24781 induces caspase and reactive oxygen species-dependent apoptosis through NF-kappaB mechanisms and is synergistic with bortezomib in lymphoma cells. Clin Cancer Res 15:3354-3365 (2009).
Biospace, Dec. 8, 2009, pharmacyclics, Inc. (PCYC) announces presentation of interim results from phase I trials of its first-in-human btk inhibitor PCI-32765.
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl): abstract 8032 (2012); [online][retrieved on Oct. 4, 2012] Retrieved for the Internet: < http://www.asco.org/ASCOv2/Meetings/Abstracts?&vmview=abst_detail_view&confID=114 &abstractID=98841>.
Buggy at al. CRA-024781: a novel synthetic inhibitor of histone deacetylase enzymes with antitumor activity in vitro and in vivo. Mol Cancer Ther. 5(5):1309-1317 (2006).
Burchat et al. Pyrazolo[3,4-d]pyrimidines Containing an Extended 3-Substituent as Potent Inhibitors of Lck—a Selectivity Insight, Bioorg. Med. Chem. Ltrs. 12:1687-1690 (2002).
Burger et al. CXCR4 antagonists: targeting the microenvironment in leukemia and other cancers, Leukemia 23:43-52 (2009).
Burger, Targeting the microenvironment in chronic lymphocytic leukemia is changing the therapeutic landscape. Curr. Opin. Oncol. 24(6):643-649 (Epub Sep. 8, 2012/Nov. 2012).
Byrd, J.C., et al., 2013, "Targeting BTK with Ibrutinib in relapsed chronic lymphocytic leukemia", New England Journal of Medicine, vol. 369, No. 1, pp. 32-42.
Carmi et al. Clinical perspectives for irreversible tyrosine kinase inhibitors in cancer, Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Chang et al. Egress of CD19+CD5+ cells into peripheral blood following treatment with the Bruton tyrosine Kinase inhibitor ibrutinib in mantel cell lymphoma patients. Blood, 122:2412-2424 (2013).
Chen et al. SYK-dependent tonic B-cell receptor signaling is a rational treatment target in diffuse large B-cell lymphoma. Blood 111(4):2230-2237 (2008) [E-pub Nov. 15. 2007].
Dana-Farber Cancer Institute. A Phase II Study of Ibrutinib Plus FCR in Previously Untreated, Younger Patients With Chronic Lymphocytic Leukemia (iFCR). In: ClinicaiTrials.gov [Internet]. Bethesda (MD): National Library of Medicine (US). Sep. 23, 2014 [cited Feb. 5, 2015] Avaliable from: https://clinicaltrial.gov/ct2/show/NCT02251548?term=NCT02251548 NLM Identifier: NCT02251548
Dana-Farber Cancer Institute. Ibrutinib (PCI-32735) in Waldenstrom's Macroglobulinemia. In: CiinicalTriais.gov [Internet]. Bethesda (MD): National Library of Medicine (US). May 17, 2012—[cited Nov. 22, 2013]. Avaliable from: http://clinicaltrials.gov/ct2/show/NCT01614821 NLM Identifier: NCT01614821.
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al. Chronic active B-cell receptor signalling in diffuse large B-cell lymphoma. Nature 463(7277):88-92 (2010).
De Miranda et al. DNA repair genes are selectively mutated in diffuse large B cell lymphomas. J Exp Med 210(9),1729-1742 (2013).
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Edwards. BTK inhibition in myeloma: targeting he seed and the soil. Blood 120(9);1757-1759 (Aug. 2012).
Friedberg at al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].

(56) References Cited

OTHER PUBLICATIONS

Gadtt et al. Differential mobilization of CD34+ Cells and lymphoma cells in non-Hodgkin's lymphoma patients mobilized with different growth factors, J of Hematotherapy & Stem Cell Research 10:167-176 (2001).
Giuliani. Multiple myeloma bone disease: pathophysiology of osteoblast inhibition. Blood (Epub Aug. 17, 2006) 108(13):3992-3996 (2006).
Gordon et al. Somatic hypermutation of the B cell receptor genes B29 (Igb, CD79b) and (Iga, CD79a), PNAS 100(7):4126-4131 (2003).
Hantschel et al. The Btk Tyrosine Kinase is a Major Target of the Bcr-Abl Inhibitor Dasatinib. PNAS 104(33):13283-13288 (2007).
Hata et al. Bruton's tyrosine kinase-mediated Interleukin-2 gene activation in mast cells. J. Biol. Chem, 273(18): 10979-10987 (1998).
Honigberg at al. Targeting Btk in Lymphoma: PCT-32765 Inhibits Tumor Growth in Mouse Lymphoma Models and a Fluorescent Analog of PCT-32765 Is an Active-Site Probe that Enables Assessment of Btk Inhibition In Vivo. Blood (Ash Annual Meeting Abstracts). 2007. 110: Abstract 1592.
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Availiable from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2013]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants With Relapsed or Refractory Mantle Cell Lymphoma, In: ClinicalTrials.gov [Internet]. Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.
Janssen Research & Development, LLC. Pharmacokinetic and Pharmacodynamic Study to Evaluate Safety and Efficacy of the Combination of Ibrutinib With Nivoiumab in Participants With Hematologic Malignancies. In: ClinicalTrials.gov [Internet]. Bethesda (MD): National Library of Medicine (US). Dec. 30, 2014 [cited Feb. 5, 2015] Available from: https://ciinicaltrial.gov/ct2/show/NCT02329847?term=NCT02329847 NLM Identifier: NCT02329847.
Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.
Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013—[cited Nov. 22, 2013]. Available from: http://clinicaltrials.gov/ct2/show/NCT01969268 NLM Identifier: NCT01989266.
Janssen Research and Development, LLC. A study combining Ibrutinib with rituximab, cyclophosphamide, doxorubicin, vincristine, and prednisone in patients with CD20-positive B-cell non Hodgkin lymphoma, In: ClinicalTrials.gov [Internet]. Bethesda (MD): National Library of Medicine (US), Mar. 30, 2012—[cited Nov. 22, 2013]. Available from: http://clinicaltrials.gov/ct2/show/NCT01569750 NLM Identifier: NCT01569750.
Janssen Research and Development, LLC. A study of ibrutinib in combination with bendamustine and rituximab in patients with relapsed or refractory chronic lymphocytic leukemia or small lymphocyic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.
Janssen Research and Development, LLC. A study of PCI-32765 (Ibrutinib) in combination with either bendamustine and rituxirnab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCTO1974440 NLM Identifier: NCT01974440,.
Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.
Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013], Available from: http://clinicaltrials.gov/ct2/show/NCT01776840 NLM Identifier: NCT01776840.
Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.
Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicaiTrials.gov [Internet], Bethesda (MD): National Library of Medicine (US). May 14, 2013—[cited Nov. 22, 2013], Available from: http://clinicaltrials.gov/ct2/show/NCTO1855750 NLM Identifier: NCT01855750.
Janssen Research and Development, LLC. A study to assess the absolute bioavailability of Oral PCI-32765 and the effect of grapefruit juice on the bioavailability of PCI-32765 in healthy participants, In: ClinicalTrials.gov [Internet], Bethesda (MD): National Library of Medicine (US). May 28, 2013—[cited Nov. 22, 2013]. Available from: http://clinicaltrials.gov/ct2/show/study/NCT01866033 NLM Identifier NCT01866033.
Janssen Research and Development, LLC. A study to assess the effect of ketoconazole on the pharmacokinetics of ibrutinib in healthy participants. In: ClinicaiTriais.gov [Internet]. Bethesda (MD): National Library of Medicine (US), Jun. 18, 2013—[cited Nov. 22, 2013]. Available from: http://clinicaltrials.gov/ct2/show/NCT01626651 NLM Identifier: NCT01626651.
Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013—[cited Nov. 22, 2013]. Available from: http://clinicaltrials.gov/ct2/show/NCT01763021 NLM Identifier: NCT01763021.
Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine

(56) References Cited

OTHER PUBLICATIONS (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012 [cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: CiinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have recieved at least one prior therapy. In: ClinicalTrials.gov [Internet]. Bethesda (MD): National Library of Medicine (US). Jul. 18, 2014—[cited Nov. 22, 2013]. Available from: http://clinicaitrials.gov/ct2/show/NCT01646021 NLM Identifier NCT01646021.

Korade-Mirnics et al. Src kinase-mediated signaling in leukocytes. J. Leukoc. Bio., 68(5):603-613 (Nov. 2000).

Kozaki et al. Development of a Bruton's tyrosine kinase (Btk) inhibitor —ONO-WG-307, a potential treatment for B-cell malignancies. 53rd American Society of Hematology Annual Meeting and Exposition, San Diego, CA, Poster #857 (Dec. 10-13, 2011).

Kuglstatter et al, Insights into the conformational flexibility of Bruton's tyrosine kinase from multiple ligand complex structures. Protein Science 20(2):428-436 (2011) [E-pub Dec. 17, 2010].

Lobe et al. Abstract C243: Activity of BTK and IIDAC inhibitors alone and in combination in a mouse model of non-small cell lung cancer. Molecular Cancer Therapeutics 12(1.1 Supp): Poster No. C243 (2013).

Lossos. Molecular Pathogenesis of Diffuse Large B-Cell Lymphoma. J. Clin. Oncol. 23(26):6351-6357 (Sep. 10, 2005).

Maddocks et al. Ibrutinib in B-cell lymphomas. Current Treatment Options in Oncology 15:226-237 (2014) (Epub: Feb. 1, 2014).

Mahajan et al. Rational Design and Synthesis of a Novel Antileukemic Agent Targeting Bruton's Tyrosine Kinase (BTK), LFM-A13 [α-Cyano-β-Methyl-N-(2,5-Dibromophenyl)Propenamide]. J. Biol. Chem. 274(14):9587-9599 (1999).

Mallis et al. Structural characterization of a proline-driven conformational switch within the Itk SH2 domain. Nat. Struct. Biol., 9(12):900-905 (2002).

Marina et al. Biology and Therapeutic Advances for Pediatric Osteosarcoma. The Oncologist 9:422-441 (2004).

M.D. Anderson Cancer Center, A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.

M.D. Anderson Cancer Center. A Phase I/II Trial of PCI-32765 (BTK Inhibitor) in Combination With Carfilzomib in Relapse/Refractory Mantel Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269065 NLM Identifier: NCT02269085.

M.D. Anderson Cancer Center, Ibrutinib Post Stem Cell Transplantation (SCT) in Double-Hit B-Cell Lymphoma, In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272686?term=NCT02272686 NLM Identifier: NCT02272686.

M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.

M.D. Anderson Cancer Center. Phase 2 ibrutinib + rituximab in relapsed/refractory mantel cell lymphoma (R/R MCL), In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.

M.D. Anderson Cancer Center, Phase 2 study of the combination of Barton's tyrosine kinase inhibitor PCI-32765 and rituximab in high-risk chronic lymphocytic leukemia and small lymphocytic lymphoma patients, In: ClinicalTrials.gov [Internet]. Bethesda (MD): National Library of Medicine (US). Jan. 25, 2015—[cited Nov. 22, 2013]. Available from http://clinicaltrials.gov/ct2/show/NCT01520519 NLM Identifier: NCT01520519.

M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012—[cited Nov. 22, 2013]. Available from: http://clinicaltrials.gov/ct2/show/NCT01752426 NLM Identifier: NCT01752426.

Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US), Dec. 9, 2014 [cited Feb. 5, 2015] Available from: https://clinicaltrial.gov/ct2/show/NCT023153267term=NCT02315326 NLM Identifier: NCT02315326.

Middendorp et al. Tumor Suppressor Function of Bruton Tyrosine Kinase is independent of its catalytic activity. Blood 105(1):259-261 (2005).

Mukoyama et al. Preparation of imidazol [1,5-a]pyrazirie derivatives, pharmaceutical compositions containing them, and their uses for prevention or treatment of protein tyrosine kinase-related diseases, retrieved from STN Database Accession No. 2005:299462 Patent. No. JP2005089352, Apr. 7, 2005.

National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [Feb. 5, 2015] Available from: https://clinicaltrial.gov/ct2/show/NCT02219737?term=NCT02219737 NLM Identifier: NCT02219737.

National Cancer institute, Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755.

National Cancer Institute, Ibrutinib in Treating Patients With Relapsed or Refractory B-cell Acute Lymphoblastic Leukemia. In: ClinicalTrials.gov [Internet]. Bethesda (MD); National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.

National Cancer institute. Ibrutinib in Treating Relapsed or Refractory B-cell Non-Hodgkin Lymphoma in Patients With HIV infection. In: ClinicalTrials.gov [Internet]. Bethesda (MD): National

(56) References Cited

OTHER PUBLICATIONS

Library of Medicine (US). Apr. 7, 2014 [cited Feb. 5, 2015]. Available from: https://clinicaltrial.gov/ct2/show/NCT02109224?term=NCT02109224. NLM Identifier: NCT02109224.
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://ciinicaltrial.gov/ct2/show/NCT02160015?term=NCT02160015 NLM Identifier: NCT02160015.
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US), Nov. 2, 2013— [cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr. 15, 2014], Available from: http://clinicaltrials.gov/ct2/show/NCT02048813 NLM Identifier: NCT02048813.
National Cancer Institute (NCI). Ibrutinib in treating patients with relapsed hairy cell leukemia. In: ClinicalTrials.gov [Internet]. Bethesda (MD): National Library of Medicine (US). Apr. 24, 2013—[cited Nov. 22, 2013]. Available from: http://clinicaltrials.gov/ct2/show/NCT01841723 NLM Identifier: NCT01841723.
National Cancer Institute (NCI). Ibrutinib in treating patients with relapsed or refractory follicular lymphoma, In: ClinicaiTrials.gov [Internet]. Bethesda (MD); National Library of Medicine (US). May 6, 2013—[cited Nov. 22, 2013]. Available from: http://clinicaltrials.gov/ct2/show/NCT01849263 NLM Identifier: NCT01849263.
National Cancer institute (NCI). Lenalidomide and ibrutinib in treating patients with relapsed or refractory B-Cell non-Hodgkin lymphoma. In: ClinicalTrials.gov [Internet], Bethesda (MD): National Library of Medicine (US). Sep. 27, 2013—[cited Nov. 22, 2013]. Available from: http://clinicaltrials.gov/ct2/show/NCT01855499 NLM Identifier: NCT01955499.
National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.
National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829588.
National Cancer Institute, Phase 1 Study of Ibrutinib and Immuno-Chemotherapy Using Dose-Adjusted-Temozolornide, Etoposide, Doxil, Dexamethasone, Ibrutinib, Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US), Jun. 24, 2013—[cited Nov. 22, 2013]. Available from: http://clinicaltriais.gov/ct2/show/NCT01886859 NLM Identifier: NCT01886859.

National Heart, Lung, and Blood Institute (NHLBI). PCI-32765 for special cases of chronic lymphocytic leukemia or small lymphocytic lymphoma. In: ClinicalTrials.gov [Internet], Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.
Nisitani et al. In situ detection of activated Bruton's tyrosine kinase in the Ig signalling complex by phosphopeptide-specific monoclonal antibodies. PNAS USA 96:2221-2226 (1999).
Northwestern University. Ibrutinib After Intensive Induction in Treating Patients With Previously Untreated Mantle Cell Lymphoma. In: ClinicalTrials.gov [Internet], Bethesda (MD): National Library of Medicine (US). Sep. 12, 2014 [cited Feb. 5, 2015] Available from: https://clinicaltrial.gov/ct2/show/NCT02242097?term=NCT02242097 NLM Identifier: NCT02242097.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2013—[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32785 in relapsed DLBCL, MCL, or indolent non-Hodgkin's lymphoma. In: ClinicalTrials.gov [Internet]. Bethesda (MD): National Library of Medicine (US). Nov. 1, 2011— [cited Feb. 6, 2014]. Available from: http://clinicaltrials.gov/ct2/show/NCT01479842 NLM Identifier: NCT01479842.
Pagel et al, Induction of apoptosis using inhibitors of lysophosphatidic acid acyltransferase-beta and anti-CD20 monoclonial antibodies for treatment of human non-Hodgkin's lymphomas. Clin. Cancer Res. (Epub Jul. 6, 2005), 11(13):4857-4866 (2005).
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (RESONATE-2). In: ClinicalTrials.gov [Internet]. Bethesda (MD): National Library of Medicine (US). Oct. 29, 2013—[cited Nov. 22, 2013]. Available from: http://clinicaltrials.gov/ct2/show/NC101722487 NLM Identifier: NCT01722487.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://ciinicaltrials.gov/ct2/show/NCT01744691 NLM Identifier: NCT01744691.
Pharmacyclics, Inc. A Multi-Center Study of Ibrutinib in Combination With Obinutuzumab Versus Chlorambucil in Combination With Obinutuzumab in Patients With Treatment naïve CLL or SLL In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A phase 3 study of ibrutinib (PCI-32765) versus ofatumurnab in patients with relapsed or refractory chronic lymphocytic leukemia (Resonate). In: ClinicalTrials.gov [Internet]. Bethesda (MD): National Library of Medicine (US). Apr. 11, 2012—[cited Nov. 22, 2013], Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine

(56) References Cited

OTHER PUBLICATIONS (US). Oct. 7, 2010—[cited Nov. 22, 2013]. Available from: http://clinicaltrials.gov/ct2/show/NCT01217749 NLM Identifier: NCT01217749.

Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.

Pharmacyclics, Inc. Ibrutinib in combination with lenalidomide, with and without rituximab in participants with relapsed or refractory diffuse large B-cell lymphoma. In: ClinicalTrials.gov [Internet], Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.

Pharmacyclics, Inc. Ibrutinib With Rituximab in Previously Treated Adults With Waldenstrom's Macroglobulinemia. In: ClinicalTrials.gov [Internet]. Bethesda (MD): National Library of Medicine (US) https://clinicaltrial.gov/ct2/show/NCT02165397?term=NCT02165397 NLM Identifier: NCT02165397.

Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://ciinicaltrials.gov/ct2/show/NCT01236391 NLM Identifier: NCT01236391.

Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.

Pharmacyclics, Inc. Safety and tolerability study of PCI-32765 combined with fiudarabine/cyclophospharnkle/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.

Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCTO1109069 NLM Identifier: NCT01109069.

Pharmacyclics, Inc. Safety of PCI-32765 in chronic lymphocytic leukemia, In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.

Pharmacyclics, Inc. Study of the Breton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.

Pharmacyclics, Inc. Study of the Barton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier NCT01980654.

Pharmacyclics, Inc. Study of the Bruton's Tyrosine kinase inhibitor in Subjects With Chronic Graft Versus Host Disease. In: ClinicalTrials.gov [Internet]. Bethesda (MD): National Library of Medicine (US). Oct. 24, 2013—[cited Nov. 22, 2013]. Available from: https://clinicaltrial.gov/ct2/show/NCT02195869?term=NCT02195869 NLM Identifier: NCT02195869.

Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier NCT01478581.

Pharmacyclics, Inc, Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29 2013—[cited Nov. 22, 2013]. Available from: http://clinicaltrials.gov/ct2/show/NCT01980628 NLM Identifier: NCT01980625.

Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.

Picci. Osteosarcoma (Osteogenic Sarcoma). Orphanet J. Rare Diseases 2(6):1-4 (2007).

Powers et al. Irreversible Inhibitors of Serine, Cysteine, and Threonine Proteases. Chem. Rev., 102(12):4639-4750 (2002).

Prakash et al. Chicken sarcoma to human cancers: a lesson in molecular therapeutics. The Ochsner Journal, 7(2):61-64 (Jan. 1, 2007).

Ritter et al. Osteosarcoma. Ann. Oncol. 21(Supplement 7):320-325 (2010).

Robak et al. A Targeted Therapy for Protien and Lipid Kinases in Chronic Lymphocytic Leukemia. Curr. Med. Chem. (Epub Jul. 24, 2012), 19(31):5294-5318 (2012).

Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).

Rushworth et al. BTK inhibitor ibrutinib is cytotoxic to myeloma and potently enhances bortezomlb and lanalidomide activities through NF-κB. Cell Signal. Sep. 11, 2012. pii: S0898-6568(12)00250-1, doi: 10.1016/j.cellsig.2012.09.008, [Epub ahead of print].

Rushworth et al. BTK inhibitor ibrutinib is cytotoxic to myeloma and potently enhances bortezomib and lenalidomide activities through NF-κB. Cell Signal (Epub Sep. 11, 2012), 25(1):106-112 (Jan. 2013).

Schwamb et al. B-cell receptor triggers drug sensitivity of primary CLL cells by controlling glucosylation of ceramides. Blood (Epub Aug. 27, 2012), 120(19):3978-3985 (Nov. 2012).

Science Daily. Counting tumor cells in blood predicts treatment benefit in prostate cancer. (Jul. 7, 2008), http://www.sciencedaily.com/releases/2008/07/080706083142.htm. last accessed Jul. 23, 2013.

Smaill et al. Tyrosine Kinase Inhibitors. 15. 4-(Phenylamino)quinazoline and 4-(Phenylamino)prido[d]pyrimidine Acrylamides as Irreversible Inhibitors of the ATP Binding Site of the Epidermal Growth Factor Receptor. J. Med. Chem. 42(10)1803-1815 (1999).

TG Therapeutics, Inc. Ublituximab + ibrutinib in select B-cell malignancies. In: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.

The Lymphoma Academic Research Organisation. Briton's tyrosine kinase (BTK) inhibition in B-cell lymphomas (BIBLOS), In: ClinicalTrials.gov [Internet]. Bethesda (MD): National Library of Medicine (US). Jan. 31, 2014—[cited Apr. 15, 2014]. Available from: http://clinicaltrials.gov/ct2/show/NCT02055924 NLM Identifier: NCT02055924.

Traxler et al. Use of a Pharmacophore Model for the Design of EGF-R Tyrosine Kinase Inhibitors: 4-(Phenylamino)pyrazolo[3,4-d]pyrimidines. J. Med Chem 40(22):3601-3616 (1997).

Uckun et al. In Vivo Pharmacokinetic Features, Toxicity Profile, and Chemosensitizing Activity of α-Cyano-β-hydroxy-β-methyl-N-

(56) References Cited

OTHER PUBLICATIONS (2,5-dibromochenyl)propenamide (LFM-A13), a Novel Antileukemic Agent Targeting Bruton's Tyrosine Kinase. Clin. Cancer Res. 8:1224-1233 (2002).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: htttps://clinicaltrial.gov/ct2/show/NCT02315768?term=NCT02315768 NLM Identifier: NCT02315768.
U.S. Appl. No. 14/671,384, filed Mar. 27, 2015.
U.S. Appl. No. 12/594,805 Final Office Action mailed Jun. 27, 2013.
U.S. Appl. No. 12/594,805 Office Action mailed Oct. 15, 2012.
U.S. Appl. No. 13/003,811 Office Action dated Feb. 25, 2013.
U.S. Appl. No. 13/153,291 Office Action mailed Jul. 5, 2013.
U.S. Appl. No. 13/153,317 Non-Final Office Action dated Jul. 23, 2015.
U.S. Appl. No. 13/340,276 Final Office Action mailed Apr. 4, 2013.
U.S. Appl. No. 13/340,276 Office Action mailed Sep. 26, 2012.
U.S. Appl. No. 13/341,695 Final Office Action mailed Jun. 7, 2013.
U.S. Appl. No. 13/341,695 Office Action mailed Feb. 1, 2013.
U.S. Appl. No. 13/361,733 Notice of Allowance mailed Nov. 14, 2012.
U.S. Appl. No. 13/404,422 Final Office Action dated Aug. 12, 2015.
U.S. Appl. No. 13/404,422 Final Office Action mailed Apr. 16, 2013.
U.S. Appl. No. 13/404,422 Office Action mailed Sep. 28, 2012.
U.S. Appl. No. 13/410,110 Final Office Action mailed Apr. 16, 2013.
U.S. Appl. No. 13/410,110 Office Action mailed Sep. 28, 2012.
U.S. Appl. No. 13/439,775 Final Office Action mailed Jun. 17, 2013.
U.S. Appl. No. 13/439,775 Office Action mailed Dec. 10, 2012.
U.S. Appl. No. 13/543,065 Office Action mailed Oct. 8, 2014.
U.S. Appl. No. 13/543,394 Office Action mailed Oct. 9, 2014.
U.S. Appl. No. 13/607,036 Final Office Action mailed Jun. 24, 2013.
U.S. Appl. No. 13/607,036 Office Action mailed Nov. 14, 2012.
U.S. Appl. No. 13/612,143 Office Action mailed Dec. 5, 2014.
U.S. Appl. No. 13/747,319 Non-Final Office Action dated Sep. 15, 2015.
U.S. Appl. No. 13/869,700 Non-Final Office Action dated Sep. 10, 2015.
U.S. Appl. No. 13/869,700 Office Action mailed Nov. 28, 2014.
U.S. Appl. No. 14/033,344 Non-Final Office Action mailed Dec. 10, 2014.
U.S. Appl. No. 14/069,222 Office Action mailed Oct. 9, 2014.
U.S. Appl. No. 14/069,233 Non-Final Office Action dated Jul. 2, 2015.
U.S. Appl. No. 14/073,543 Office Action mailed Dec. 15, 2014.
U.S. Appl. No. 14/073,594 Final Office Action dated Jul. 1, 2015.
U.S. Appl. No. 14/073,594 Office Action mailed Dec. 15, 2014.
U.S. Appl. No. 14/079,508 Office Action mailed Dec. 15, 2014.
U.S. Appl. No. 14/080,640 Final Office Action mailed May 13, 2015.
U.S. Appl. No. 14/080,649 Final Office Action dated May 21, 2015.
U.S. Appl. No. 14/091,196 Office Action dated May 19, 2015.
U.S. Appl. No. 14/179,457 Final Office Action dated Dec. 22, 2014.
U.S. Appl. No. 14/188,390 Non-Final Office Action dated Aug. 26, 2015.
U.S. Appl. No. 14/340,483 Office Action maied May 5, 2015.
U.S. Appl. No. 14/344,314 Non-Final Office Action dated May 22, 2015.
U.S. Appl. No. 14/450,068 Non-Final Office Action dated May 21, 2015.
Vose. Mantle cell lymphoma: 2012 update on diagnosis, risk-stratification, and clinical management. Am. J. Hematol. 87(6):604-809 (Jun. 2012).
Wilkinson et al. Selective tyrosine kinase inhibitors. Expert Opin. Emerging Drugs 5(3):287-297 (2000).
Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120: Abstract 686 (2012).
Witzens-Harig et al. Current treatment of mantle cell lymphoma: results of a national survey and consensus meeting. Ann Hematol. (Epub Aug. 29, 2012), 91(11):1765-1772 (Nov. 2012).
Yang et al. Histone deacetylase inhibitor (HDACI) PCI-24781 potentiates cytotoxic effects of doxorubicin in bone sarcoma cells. Cancer Chemother Pharmacol. 67(2):439-46 (2011).
Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].
Yasuhiro et al. ONO-WG-307, a Novel, Potent and Selective Inhibitor of Bruton's Tyrosine Kinase, in sustained inhibition of the Erk, Akt and PKD signaling pathways, 53rd American Society of Hematology Annual Meeting and Exposition, San Diego, CA, Poster #2021 (Dec. 10-13, 2011).
Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).
Zhu et al. Calpain Inhibitor II Induces Caspase-dependent Apoptosis in Human Acute Lymphoblastic Leukemia and Non-Hodgkin's Lymphoma Cells as well as Some Solid Tumor Cells. Clin. Cancer Res. 6:2456-2463 (2000).

FIG. 11

| Cell Line Name | Cancer Type | Combination Effects of lapatinib and abt-263/737 |
|---|---|---|
| MDA-MB-453 | Breast carcinoma | Synergy |
| DLD-1 | colorectal adenocarcinoma | Weak Synergy |
| NCI-H460 | lung | Additive |
| A549 | lung | no additional effect when combined |
| LNCaP | prostate carcinoma | no additional effect when combined |

METHODS FOR THE TREATMENT OF SOLID TUMORS

CROSS-REFERENCE

This application claims the benefit of U.S. Application Ser. No. 61/861,853, filed Aug. 2, 2013, which is incorporated herein by reference in its entirety.

SUMMARY OF THE INVENTION

Disclosed herein, in certain embodiments, are compositions comprising a therapeutically effective amount of an ACK inhibitor compound, a therapeutically effective amount of an HDAC inhibitor compound, and a pharmaceutically acceptable excipient. In some embodiments, the ACK inhibitor compound is a BTK inhibitor. In some embodiments, the BTK inhibitor is an irreversible BTK inhibitor. In some embodiments, the ACK inhibitor is a compound of Formula (A):

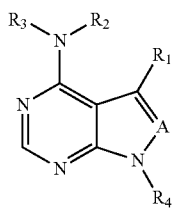

Formula (A)

wherein
A is independently selected from N or $CR_5$;
$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);
$R_2$ and $R_3$ are independently selected from H, lower alkyl and substituted lower alkyl;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;

G is

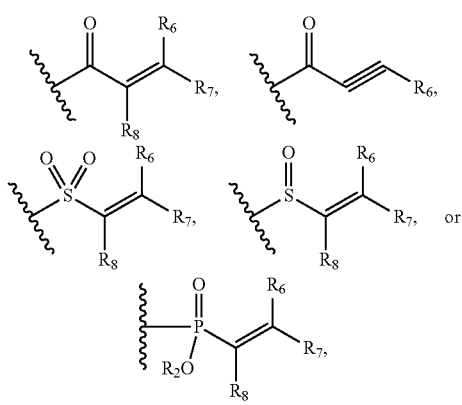

wherein,
$R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_9$ and $R_{10}$ can together form a 5-, 6-, 7-, or 8-membered heterocyclic ring; or
each $R_{11}$ is independently selected from H, —S(=O)$_2$R$_8$, —S(=O)$_2$NH$_2$, —C(O)R$_8$, —CN, —NO$_2$, heteroaryl, or heteroalkyl.
In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

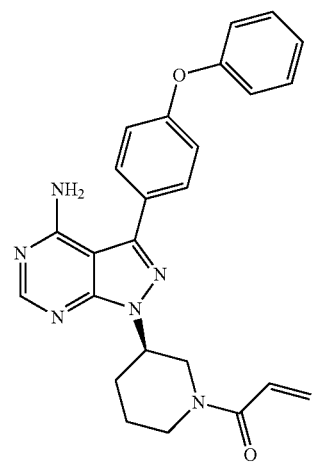

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B):

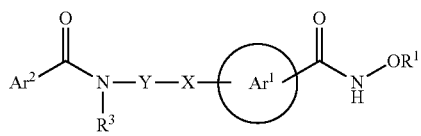

Formula (B)

wherein:
$R^1$ is hydrogen or alkyl;
X is —O—, —NR²—, or —S(O)$_n$ where n is 0-2 and $R^2$ is hydrogen or alkyl;
Y is alkylene optionally substituted with cycloalkyl, optionally substituted phenyl, alkylthio, alkylsulfinyl, alkylsulfonyl, optionally substituted phenylalkylthio, optionally substituted phenylalkylsulfonyl, hydroxy, or optionally substituted phenoxy;
$Ar^1$ is phenylene or heteroarylene wherein said $Ar^1$ is optionally substituted with one or two groups independently selected from alkyl, halo, hydroxy, alkoxy, haloalkoxy, or haloalkyl;
$R^3$ is hydrogen, alkyl, hydroxyalkyl, or optionally substituted phenyl; and
$Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl. In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

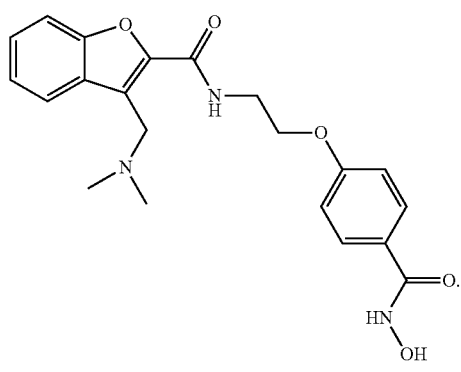

Abexinostat

In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

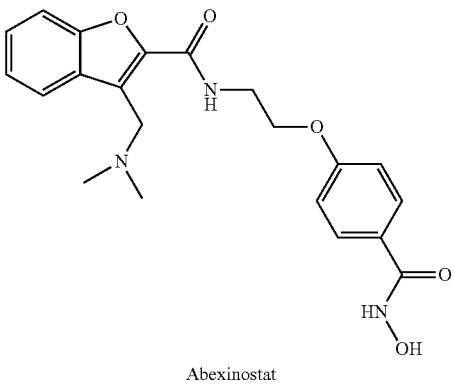 [SMILES: CN(C)Cc1c(C(=O)NCCOc2ccc(C(=O)NO)cc2)oc2ccccc12]

Abexinostat and,
the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

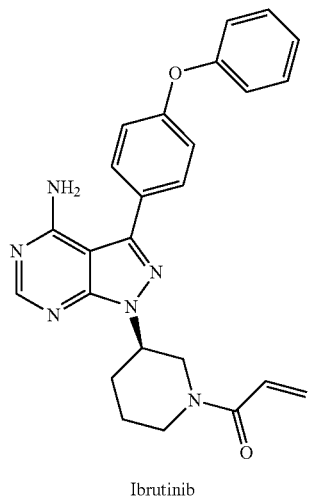

Ibrutinib

In some embodiments, the composition is in the form of a solid dosage form. In some embodiments, the composition is in the form of a capsule. In some embodiments, the composition is in the form of a solution. In some embodiments, the composition is in the form of a solution for intravenous administration. In some embodiments, the compositions comprise 140 mg of ibrutinib. In some embodiments, the composition is for use in treatment of a solid tumor. In some embodiments, the composition is for use in treatment of a sarcoma or carcinoma. In some embodiments, the composition is for use in treatment of a sarcoma. In some embodiments, the composition is for use in treatment of a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extraskeletal osteosarcoma; fibrosarcoma; giant cell tumor; hemangiopericytoma; infantile fibrosarcoma; inflammatory myofibroblastic tumor; Kaposi sarcoma; leiomyosarcoma of bone;

liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the non-small cell lung cancer is large cell lung cancer. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, the combination of ibrutinib and abexinostat is 5%, 10%, 15%, 20%, 25%, 30%, 35%, 40%, 45%, 50%, 55% or 60% more efficacious than administration of abexinostat alone. In some embodiments, the combination of the ibrutinib and abexinostat is 50% more efficacious than administration of abexinostat alone. In some embodiments, the combination of ibrutinib and abexinostat is 5%, 10%, 15%, 20%, 25%, 30%, or 35% more efficacious than administration of ibrutinib alone. In some embodiments, the combination of ibrutinib and abexinostat is 25% more efficacious than administration of ibrutinib alone.

Disclosed herein, in certain embodiments, are combinations of a therapeutically effective amount of an ACK inhibitor compound and a therapeutically effective amount of an HDAC inhibitor compound. In some embodiments, the ACK inhibitor compound is a BTK inhibitor. In some embodiments, the BTK inhibitor is an irreversible BTK inhibitor. In some embodiments, the ACK inhibitor is a compound of Formula (A):

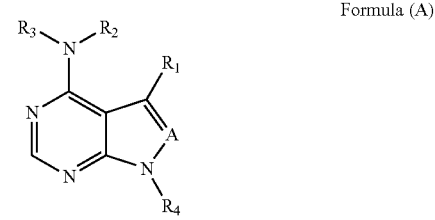

Formula (A)

wherein
A is independently selected from N or $CR_5$;
$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);
$R_2$ and $R_3$ are independently selected from H, lower alkyl and substituted lower alkyl;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —$NR_9$, —NHC(O), —C(O)NH, —$NR_9$C(O), —C(O)$NR_9$, —S(=O)$_2$NH, —NHS(=O)$_2$, —S(=O)$_2$$NR_9$—, —$NR_9$S(=O)$_2$, —OC(O)NH—, —NHC(O)O—, —OC(O)$NR_9$—, —$NR_9$C(O)O—, —CH=NO—, —ON=CH—, —$NR_{10}$C(O)$NR_{10}$—, heteroaryl, aryl, —$NR_{10}$C(=$NR_{11}$)$NR_{10}$—, —$NR_{10}$C(=$NR_{11}$)—, —C(=$NR_{11}$)$NR_{10}$—, —OC(=$NR_{11}$)—, or —C(=$NR_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;
G is -continued

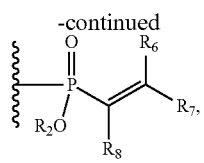

wherein,
$R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_5$ is H, halogen, $-L_6$-(substituted or unsubstituted $C_1$-$C_3$ alkyl), $-L_6$-(substituted or unsubstituted $C_2$-$C_4$ alkenyl), $-L_6$-(substituted or unsubstituted heteroaryl), or $-L_6$-(substituted or unsubstituted aryl), wherein $L_6$ is a bond, O, S, —S(═O), S(═O)$_2$, NH, C(O), —NHC(O)O, —OC(O)NH, —NHC(O), or —C(O)NH;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_9$ and $R_{10}$ can together form a 5-, 6-, 7-, or 8-membered heterocyclic ring; or each $R_{11}$ is independently selected from H, —S(═O)$_2$$R_8$, —S(═O)$_2$NH$_2$, —C(O)$R_8$, —CN, —NO$_2$, heteroaryl, or heteroalkyl.

In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

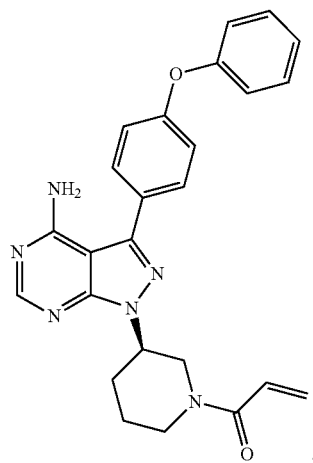

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B):

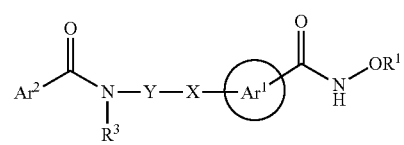

Formula (B)

wherein:
$R^1$ is hydrogen or alkyl;

X is —O—, —NR$^2$—, or —S(O)$_n$ where n is 0-2 and $R^2$ is hydrogen or alkyl;

Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

Ar$^1$ is phenylene or heteroarylene wherein said Ar$^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and

Ar$^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl. In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

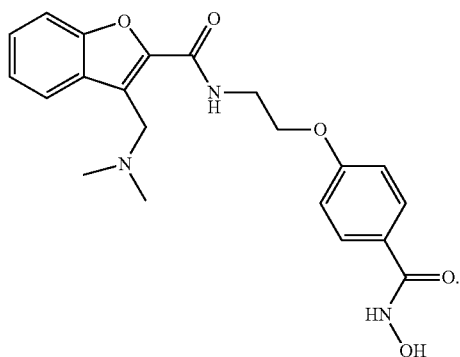

Abexinostat

In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

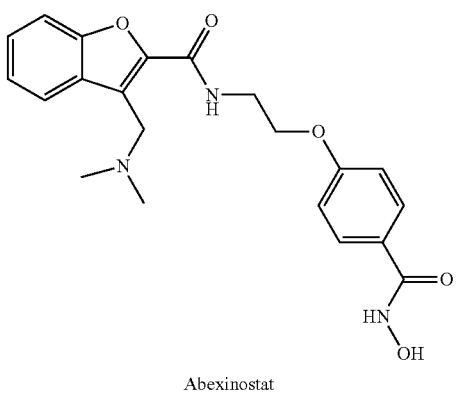 [SMILES: CN(C)Cc1c(C(=O)NCCOc2ccc(C(=O)NO)cc2)oc2ccccc12]

Abexinostat and,
the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

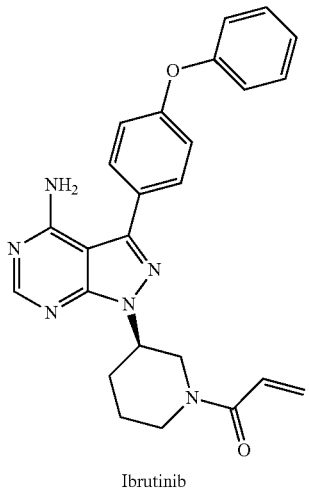

Ibrutinib

In some embodiments the combination is administered in a solid dosage form. In some embodiments the combination is administered in a capsule. In some embodiments the combination is administered in a solution. In some embodiments the combination is administered in a solution for intravenous administration. In some embodiments the combination, comprises 140 mg of ibrutinib. In some embodiments, the combination is for use in treatment of a solid tumor. In some embodiments, the combination is for use in treatment of a sarcoma or carcinoma. In some embodiments, the combination is for use in treatment of a sarcoma. In some embodiments, the combination is for use in treatment of a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extrasketetal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the non-small cell lung cancer is large cell lung cancer. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, the combination of ibrutinib and abexinostat is 5%, 10%, 15%, 20%, 25%, 30%, 35%, 40%, 45%, 50%, 55% or 60% more efficacious than administration of abexinostat alone. In some embodiments, the combination of the ibrutinib and abexinostat is 50% more efficacious than administration of abexinostat alone. In some embodiments, the combination of ibrutinib and abexinostat is 5%, 10%, 15%, 20%, 25%, 30%, or 35% more efficacious than administration of ibrutinib alone. In some embodiments, the combination of ibrutinib and abexinostat is 25% more efficacious than administration of ibrutinib alone. In some embodiments the combination is administered in a unified dosage form or separate dosage forms. In some embodiments the combination is administered simultaneously or sequentially.

Disclosed herein, in certain embodiments, are methods for treating a solid tumor comprising co-administering to an individual in need thereof an ACK inhibitor compound and an HDAC inhibitor compound. In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

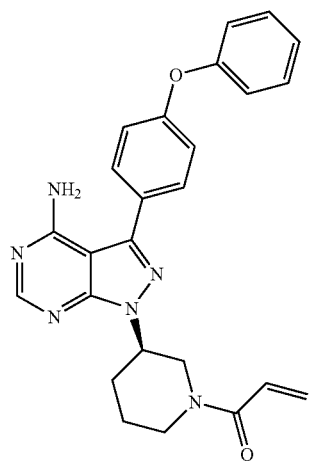

Ibrutinib

In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

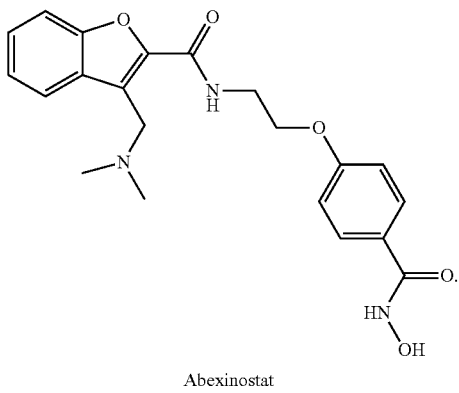 [SMILES: CN(C)Cc1c(C(=O)NCCOc2ccc(C(=O)NO)cc2)oc2ccccc12]

Abexinostat

In some embodiments, the solid tumor is a carcinoma. In some embodiments, the carcinoma is breast cancer. In some embodiments, the carcinoma is pancreatic cancer. In some embodiments, the carcinoma is colorectal cancer. In some embodiments, the carcinoma is bladder cancer. In some embodiments, the carcinoma is lung cancer. In some embodiments, the lung cancer is a non-small cell lung cancer. In some embodiments, the lung cancer is a large cell lung cancer. In some embodiments, the carcinoma is prostate cancer. In some embodiments, the carcinoma is ovarian cancer. In some embodiments, the carcinoma is bile duct cancer. In some embodiments, co-administration of the ACK inhibitor and the HDAC inhibitor is 50% more efficacious than administration of the HDAC inhibitor alone. In some embodiments, co-administration of the ACK inhibitor and the HDAC inhibitor is 25% more efficacious than administration of the ACK inhibitor alone. In some embodiments, the ACK inhibitor and the HDAC inhibitor are administered in a unified dosage form or separate dosage forms. In some embodiments, the ACK inhibitor and the HDAC inhibitor are administered simultaneously or sequentially.

Disclosed herein, in certain embodiments, are methods for treating a solid tumor comprising co-administering to an individual in need thereof an ACK inhibitor compound and an HDAC inhibitor compound. In some embodiments, the ACK inhibitor compound is a BTK inhibitor. In some embodiments, the BTK inhibitor is an irreversible BTK inhibitor. In some embodiments, the ACK inhibitor is a compound of Formula (A):

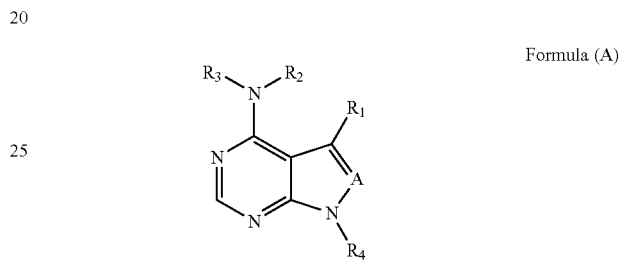

Formula (A)

wherein

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

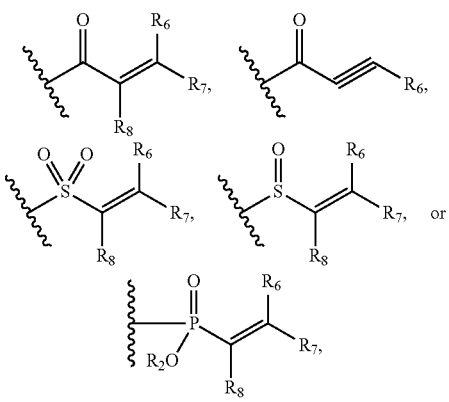

wherein,
$R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(═O), S(═O)$_2$, NH, C(O), —NHC(O)O, —OC(O)NH, —NHC(O), or —C(O)NH;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_9$ and $R_{10}$ can together form a 5-, 6-, 7-, or 8-membered heterocyclic ring; or
each $R_{11}$ is independently selected from H, —S(═O)$_2$$R_8$, —S(═O)$_2$NH$_2$, —C(O)$R_8$, —CN, —NO$_2$, heteroaryl, or heteroalkyl.

In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B):

Formula (B)

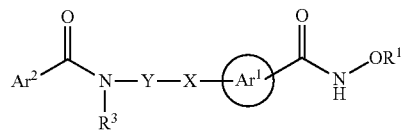

wherein:
$R^1$ is hydrogen or alkyl;
X is —O—, —NR$^2$—, or —S(O)$_n$ where n is 0-2 and $R^2$ is hydrogen or alkyl;
Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;
$Ar^1$ is phenylene or heteroarylene wherein said $Ar^1$ is optionally substituted with one or two groups independently selected from alkyl, halo, hydroxy, alkoxy, haloalkoxy, or haloalkyl;
$R^3$ is hydrogen, alkyl, hydroxyalkyl, or optionally substituted phenyl; and
$Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl. In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

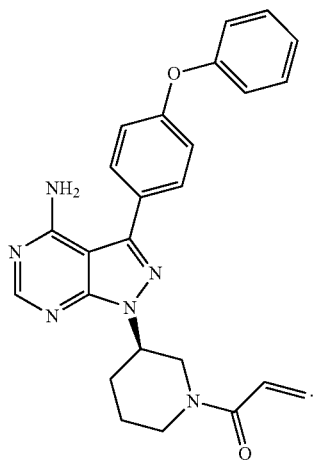

Ibrutinib

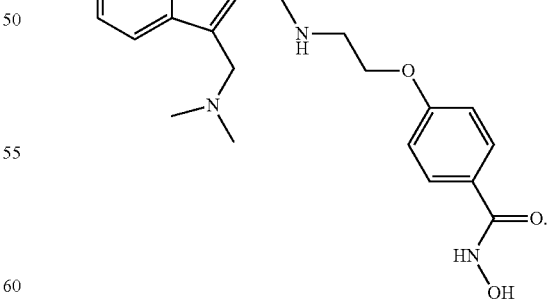

Abexinostat

In some embodiments, the solid tumor is a sarcoma or carcinoma. In some embodiments, the solid tumor is a sarcoma. In some embodiments, the solid tumor is a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extraskeletal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, co-administration of the ACK inhibitor and the HDAC inhibitor is 5%, 10%, 15%, 20%, 25%, 30%, 35%, 40%, 45%, 50%, 55% or 60% more efficacious than administration of the HDAC inhibitor alone. In some embodiments, co-administration of the ACK inhibitor and the HDAC inhibitor is 50% more efficacious than administration of the HDAC inhibitor alone. In some embodiments, co-administration of the ACK inhibitor and the HDAC inhibitor is 5%, 10%, 15%, 20%, 25%, 30%, or 35% more efficacious than administration of the ACK inhibitor alone. In some embodiments, co-administration of the ACK inhibitor and the HDAC inhibitor is 25% more efficacious than administration of the ACK inhibitor alone. In some embodiments, the ACK inhibitor and the HDAC inhibitor are administered in a unified dosage form or separate dosage forms. In some embodiments, the ACK inhibitor and the HDAC inhibitor are administered simultaneously or sequentially.

Disclosed herein, in certain embodiments, are methods for treating a solid tumor comprising co-administering to an individual in need thereof an HDAC inhibitor compound and (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

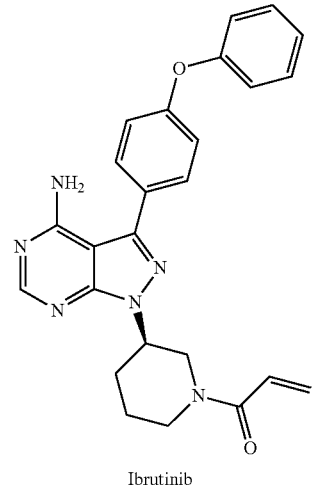

Ibrutinib

In some embodiments, the HDAC inhibitor is a compound of Formula (B):

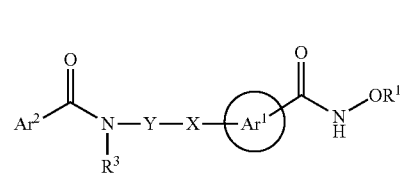

Formula (B)

wherein:
$R^1$ is hydrogen or alkyl;
X is —O—, —$NR^2$—, or —S(O)$_n$— where n is 0-2 and $R^2$ is hydrogen or alkyl;
Y is alkylene optionally substituted with cycloalkyl, optionally substituted phenyl, alkylthio, alkylsulfinyl, alkylsulfonyl, optionally substituted phenylalkylthio, optionally substituted phenylalkylsulfonyl, hydroxy, or optionally substituted phenoxy;
$Ar^1$ is phenylene or heteroarylene wherein said $Ar^1$ is optionally substituted with one or two groups independently selected from alkyl, halo, hydroxy, alkoxy, haloalkoxy, or haloalkyl;

R³ is hydrogen, alkyl, hydroxyalkyl, or optionally substituted phenyl; and

Ar² is aryl, aralkenyl, heteroaryl, heteroaralkyl, heteroaralkenyl, cycloalkyl, cycloalkylalkyl, heterocycloalkyl, or heterocycloalkylalkyl.

In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

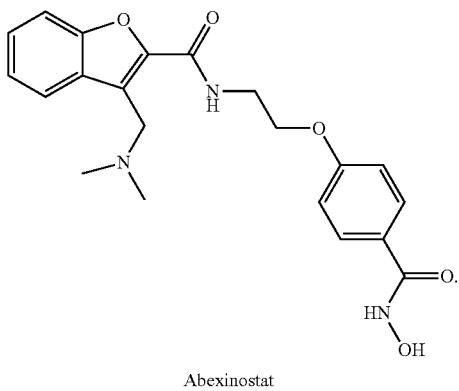 [SMILES: CN(C)Cc1c(C(=O)NCCOc2ccc(C(=O)NO)cc2)oc2ccccc12]

Abexinostat

In some embodiments, the solid tumor is a sarcoma or carcinoma. In some embodiments, the solid tumor is a sarcoma. In some embodiments, the solid tumor is a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extrasketetal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, co-administration of ibrutinib and the HDAC inhibitor is 5%, 10%, 15%, 20%, 25%, 30%, 35%, 40%, 45%, 50%, 55% or 60% more efficacious than administration of the HDAC inhibitor alone. In some embodiments, co-administration of ibrutinib and the HDAC inhibitor is 50% more efficacious than administration of the HDAC inhibitor alone. In some embodiments, co-administration of ibrutinib and the HDAC inhibitor is 5%, 10%, 15%, 20%, 25%, 30%, or 35% more efficacious than administration of ibrutinib alone. In some embodiments, co-administration of ibrutinib and the HDAC inhibitor is 25% more efficacious than administration of ibrutinib alone. In some embodiments, ibrutinib and the HDAC inhibitor are administered in a unified dosage form or separate dosage forms. In some embodiments, ibrutinib and the HDAC inhibitor are administered simultaneously or sequentially.

Disclosed herein, in certain embodiments, are methods for treating a solid tumor comprising co-administering to an individual in need thereof an ACK inhibitor compound and 3-[(dimethylamino)methyl]-N-{2-[4-(hydroxycarbamoyl)phenoxy]ethyl}-1-benzofuran-2-carboxamide (i.e. PCI-24781/abexinostat)

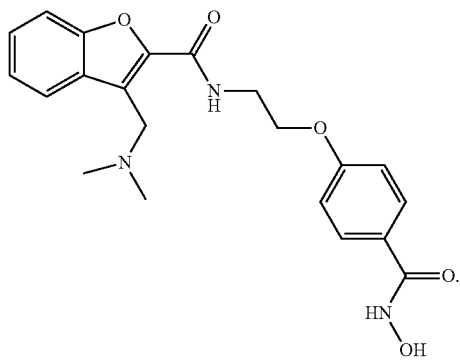

Abexinostat

In some embodiments, the ACK inhibitor compound is a BTK inhibitor. In some embodiments, the BTK inhibitor is an irreversible BTK inhibitor. In some embodiments, the ACK inhibitor is a compound of Formula (A):

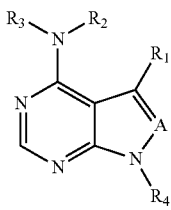

Formula (A)

wherein

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

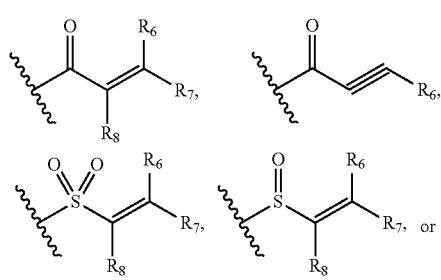

-continued

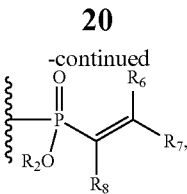

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_9$ and $R_{10}$ can together form a 5-, 6-, 7-, or 8-membered heterocyclic ring; or each $R_{11}$ is independently selected from H, —S(=O)$_2$R$_8$, —S(=O)$_2$NH$_2$, —C(O)R$_8$, —CN, —NO$_2$, heteroaryl, or heteroalkyl. In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

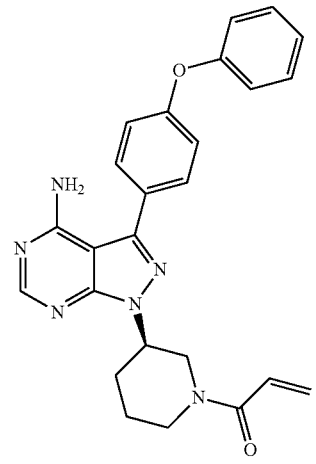

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the solid tumor is a sarcoma or carcinoma. In some embodiments, the solid tumor is a sarcoma. In some embodiments, the solid tumor is a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extrasketetal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, co-administration of the abexinostat and the ACK inhibitor is 5%, 10%, 15%, 20%, 25%, 30%, 35%, 40%, 45%, 50%, 55% or 60% more efficacious than administration of abexinostat alone. In some embodiments, co-administration of the abexinostat and the ACK inhibitor is 50% more efficacious than administration of abexinostat alone. In some embodiments, co-administration of the abexinostat and the ACK inhibitor is 5%, 10%, 15%, 20%, 25%, 30%, or 35% more efficacious than administration of the ACK inhibitor alone. In some embodiments, co-administration of the abexinostat and the ACK inhibitor is 25% more efficacious than administration of the ACK inhibitor alone. In some embodiments, the ACK inhibitor and abexinostat are administered in a unified dosage form or separate dosage forms. In some embodiments, the ACK inhibitor and abexinostat are administered simultaneously or sequentially.

Disclosed herein, in certain embodiments, are methods for treating a solid tumor comprising administering to an individual in need thereof a combination of (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

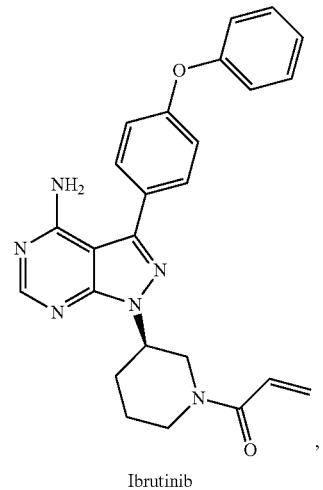 [SMILES: C=CC(=O)N1CCC[C@@H](n2nc(-c3ccc(Oc4ccccc4)cc3)c3c(N)ncnc32)C1]

Ibrutinib and 3-[(dimethylamino)methyl]-N-{2-[4-(hydroxycarbamoyl)phenoxy]ethyl}-1-benzofuran-2-carboxamide (i.e. PCI-24781/abexinostat)

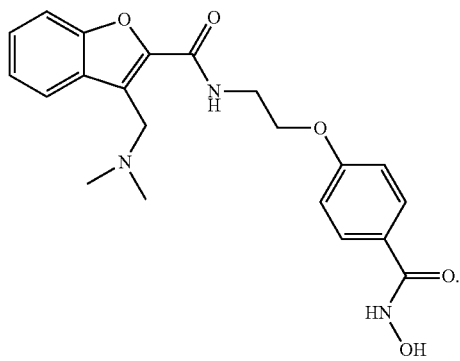

Abexinostat

In some embodiments, the solid tumor is a sarcoma or carcinoma. In some embodiments, the solid tumor is a sarcoma. In some embodiments, the solid tumor is a carcinoma. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extrasketetal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma. In some embodiments, co-administration of ibrutinib and abexinostat is 5%, 10%, 15%, 20%, 25%, 30%, 35%, 40%, 45%, 50%, 55% or 60% more efficacious than administration of abexinostat alone. In some embodiments, co-administration of the ibrutinib and abexinostat is 50% more efficacious than administration of abexinostat alone. In some embodiments, co-administration of ibrutinib and abexinostat is 5%, 10%, 15%, 20%, 25%, 30%, or 35% more efficacious than administration of ibrutinib alone. In some embodiments, co-administration of ibrutinib and abexinostat is 25% more efficacious than administration of ibrutinib alone. In some embodiments, abexinostat and ibrutinib are administered in a unified dosage form or separate dosage forms. In some embodiments, abexinostat and ibrutinib are administered simultaneously or sequentially.

Disclosed herein, in certain embodiments, are compositions comprising a therapeutically effective amount of an ACK inhibitor compound, a therapeutically effective amount of an HDAC inhibitor compound, and a pharmaceutically acceptable excipient. In some embodiments, the ACK inhibitor compound is a BTK inhibitor. In some embodiments, the BTK inhibitor is an irreversible BTK inhibitor. In some embodiments, the ACK inhibitor is a compound of Formula (A):

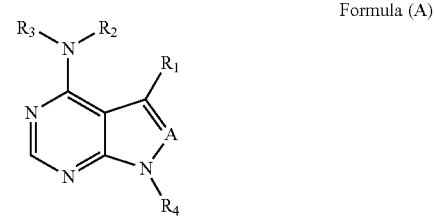

Formula (A)

wherein
A is independently selected from N or CR$_5$;
R$_1$ is H, L$_2$-(substituted or unsubstituted alkyl), L$_2$-(substituted or unsubstituted cycloalkyl), L$_2$-(substituted or unsubstituted alkenyl), L$_2$-(substituted or unsubstituted cycloalkenyl), L$_2$-(substituted or unsubstituted heterocycle), L$_2$-(substituted or unsubstituted heteroaryl), or L$_2$-(substituted or unsubstituted aryl), where L$_2$ is a bond, O, S, —S(=O), —S(=O)$_2$, C(=O), -(substituted or unsubstituted C$_1$-C$_6$ alkyl), or -(substituted or unsubstituted C$_2$-C$_6$ alkenyl);
R$_2$ and R$_3$ are independently selected from H, lower alkyl and substituted lower alkyl;
R$_4$ is L$_3$-X-L$_4$-G, wherein,
L$_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_1$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
L$_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or L$_3$, X and L$_4$ taken together form a nitrogen containing heterocyclic ring;

G is

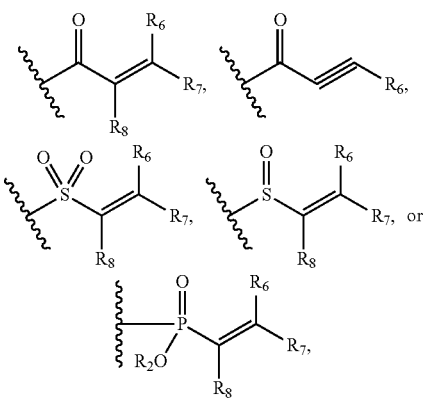

wherein,
R$_6$, R$_7$ and R$_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

R$_5$ is H, halogen, -L$_6$-(substituted or unsubstituted C$_1$-C$_3$ alkyl), -L$_6$-(substituted or unsubstituted C$_2$-C$_4$ alkenyl), -L$_6$-(substituted or unsubstituted heteroaryl), or -L$_6$-(substituted or unsubstituted aryl), wherein L$_6$ is a bond, O, S, —S(=O), S(=O)$_2$, NH, C(O), —NHC(O)O, —OC(O)NH, —NHC(O), or —C(O)NH;

each R$_9$ is independently selected from among H, substituted or unsubstituted lower alkyl, and substituted or unsubstituted lower cycloalkyl;

each R$_{10}$ is independently H, substituted or unsubstituted lower alkyl, or substituted or unsubstituted lower cycloalkyl; or two R$_{10}$ groups can together form a 5-, 6-, 7-, or 8-membered heterocyclic ring; or R$_9$ and R$_{10}$ can together form a 5-, 6-, 7-, or 8-membered heterocyclic ring; or each R$_{11}$ is independently selected from H, —S(=O)$_2$R$_8$, —S(=O)$_2$NH$_2$, —C(O)R$_8$, —CN, —NO$_2$, heteroaryl, or heteroalkyl. In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B):

Formula (B)

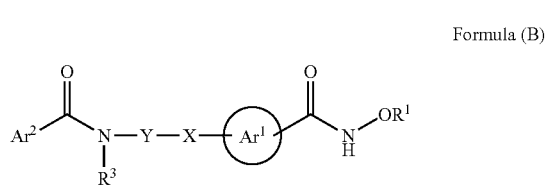

wherein:
R$^1$ is hydrogen or alkyl;
X is —O—, —NR$^2$—, or —S(O)$_n$ where n is 0-2 and R$^2$ is hydrogen or alkyl;
Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;
Ar$^1$ is phenylene or heteroarylene wherein said Ar$^1$ is optionally substituted with one or two groups independently selected from alkyl, halo, hydroxy, alkoxy, haloalkoxy, or haloalkyl;
R$^3$ is hydrogen, alkyl, hydroxyalkyl, or optionally substituted phenyl; and
Ar$^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl. In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

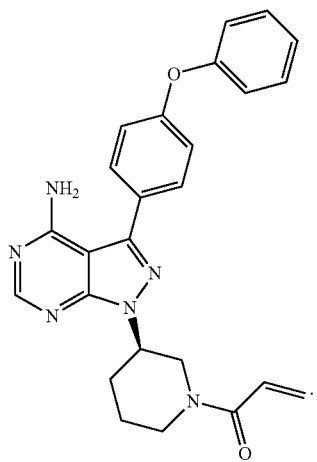

Ibrutinib

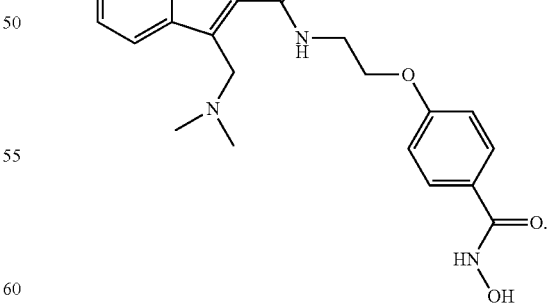

Abexinostat

In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat)

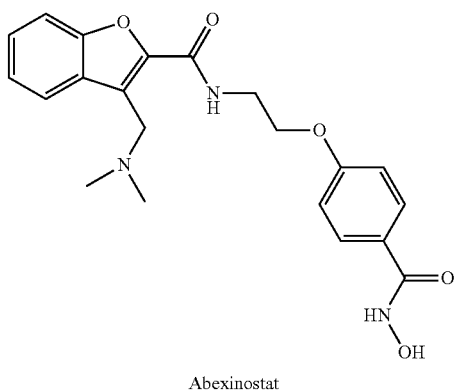 [SMILES: CN(C)Cc1c(C(=O)NCCOc2ccc(C(=O)NO)cc2)oc2ccccc12]

Abexinostat and, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

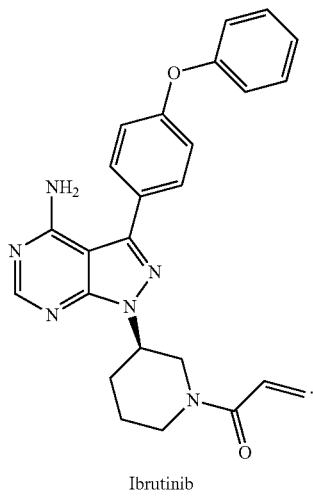 [SMILES: C=CC(=O)N1CCC[C@@H](n2nc(-c3ccc(Oc4ccccc4)cc3)c3c(N)ncnc32)C1]

Ibrutinib

In some embodiments, the composition is in the form of a solid dosage form. In some embodiments, the composition is in the form of a capsule. In some embodiments, the composition is in the form of a solution. In some embodiments, the composition is in the form of a solution for intravenous administration. In some embodiments, the composition comprises 140 mg of ibrutinib.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

BRIEF DESCRIPTION OF THE FIGURES

FIG. 11: Is a table exemplifying the effects of the combination of abexinostat and ibrutinib is MDA-MB-453 cells (breast carcinoma), DLD-1 cells (colorectal adenocarcinoma), NCI-H460 cells (large cell lung cancer), A549 cells (lung carcinoma) and LNCap cells (prostate carcinoma). The combination showed synergy for MDA-MB-453 cells, weak synergy for DLD-1 cells, additivity for NCI-H460 cells, and no additional effect for A549 and LNCaP cells.

DETAILED DESCRIPTION OF THE INVENTION

Figure 1:
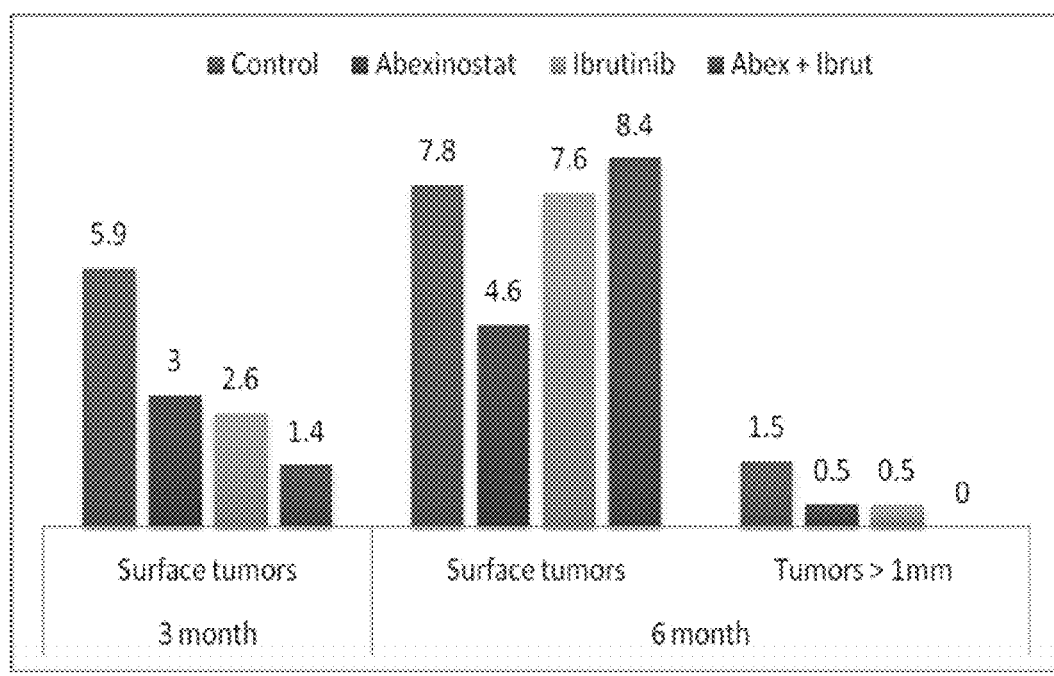
FIG. 1: Is an illustrative example of the average number of tumors on the lung surface for control and drug-treated (abexinostat, ibrutinib, or abexinostat+ibrutinib) Grg1 transgenic mice. The bars at the left show mice treated for 4 weeks beginning at 2 months (3 month samples) and the bars in the middle show mice treated for 4 weeks beginning at 5 months (6 month samples). The average number of tumors over 1 mm for 6 month samples is also shown.

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

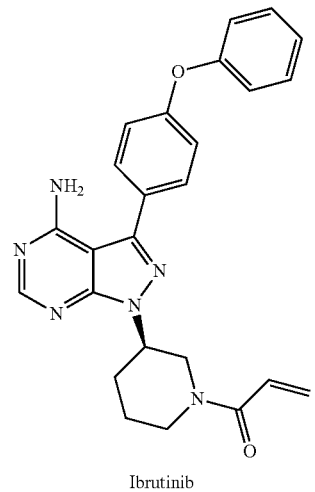 [SMILES: C=CC(=O)N1CCC[C@@H](n2nc(-c3ccc(Oc4ccccc4)cc3)c3c(N)ncnc32)C1]

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

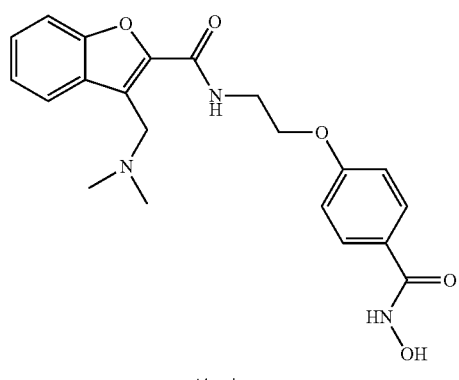

Abexinostat

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, "ACK" and "Accessible Cysteine Kinase" are synonyms. They mean a kinase with an accessible cysteine residue. ACKs include, but are not limited to, BTK, ITK, Bmx/ETK, TEC, EFGR, HER4, HER4, LCK, BLK, C-src, FGR, Fyn, HCK, Lyn, YES, ABL, Brk, CSK, FER, JAK3, SYK. In some embodiments, the ACK is HER4.

As used herein, "amelioration" refers to any lessening of severity, delay in onset, slowing of growth, slowing of metastasis, or shortening of duration of a solid tumor, whether permanent or temporary, lasting or transient that can be attributed to or associated with administration of the compound or composition.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ").

The term "HER4", also known as ERBB4, also known as "V-erb-a erythroblastic leukemia viral oncogene homolog 4" means either (a) the nucleic acid sequence encoding a receptor tyrosine kinase that is a member of the epidermal growth factor receptor subfamily, or (b) the protein thereof. For the nucleic acid sequence that comprises the human HER4 gene see GenBank Accession No. NM_001042599. For the amino acid sequence that comprises the human HER4 protein see GenBank Accession No. NP_001036064.

The terms "co-administration" or the like, as used herein, encompass administration of an ACK inhibitor compound and an HDAC inhibitor compound to a single patient, and are intended to include treatment regimens in which the agents are administered by the same or different route of administration, in the same or a different dosage form, and at the same or different time.

The term "homologous cysteine," as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

Figure 7:
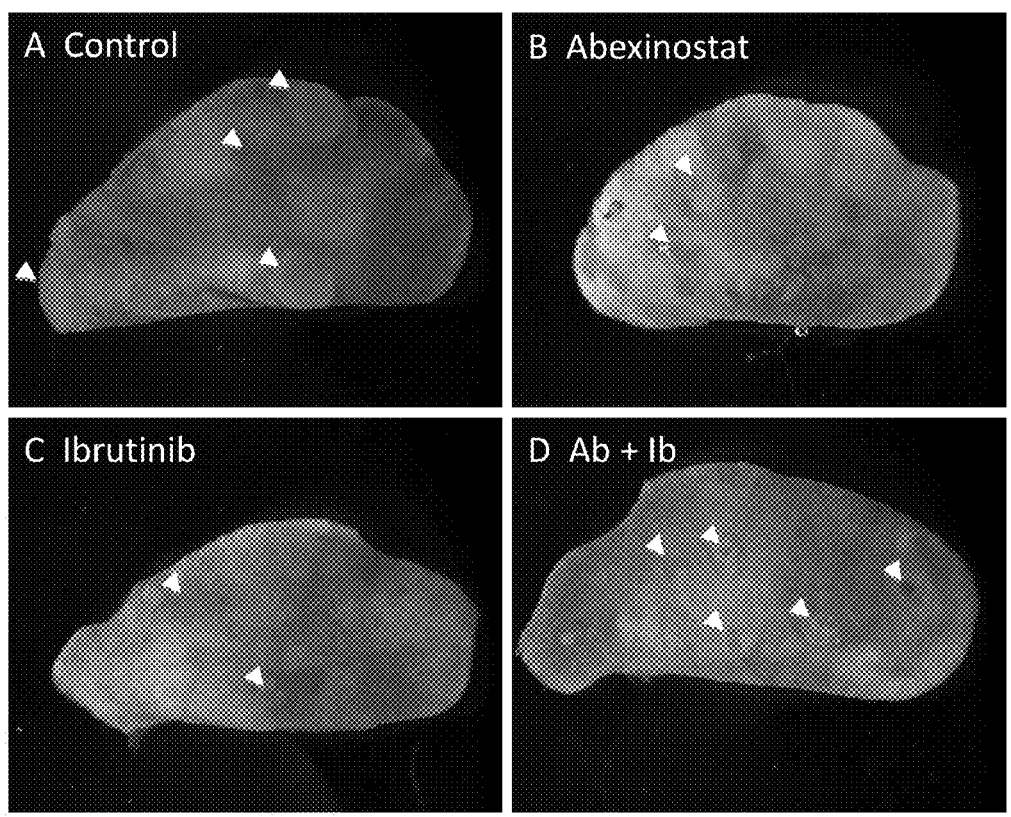
FIG. 7: Is an illustrative example of whole left lung lobes from 6 month Grg1 transgenic mice after 4 weeks of treatment with abexinostat, ibrutinib, or the combination of abexinostat and ibrutinib. Three large tumors and one small tumor are visible in the control sample (A); medium and small tumors are visible in Abexinostat-treated (B), Ibrutinib-treated (C) and Abexinostat+Ibrutinib-treated (D) samples.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in FIG. 7.

As used herein, the term "pERK" refers to phosphorylated ERK1 and ERK2 at Thr202/Tyr 204 as detected by commercially available phospho-specific antibodies (e.g. Cell Signaling Technologies #4377).

The terms "individual", "patient" and "subject" are used interchangeable. They refer to a mammal (e.g., a human) which is the object of treatment, or observation. The term is not to be construed as requiring the supervision of a medical practitioner (e.g., a physician, physician's assistant, nurse, orderly, hospice care worker).

The terms "treat," "treating" or "treatment", as used herein, include lessening of severity of a solid tumor, delay in onset of a solid tumor, slowing the growth of a solid tumor, slowing metastasis of cells of a solid tumor, shortening of duration of a solid tumor, arresting the development of a solid tumor, causing regression of a solid tumor, relieving a condition caused by of a solid tumor, or stopping symptoms which result from a solid tumor. The terms "treat," "treating" or "treatment", include, but are not limited to, prophylactic and/or therapeutic treatments.

Therapeutic Methods

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

Solid Tumors

As used herein, a "solid tumor" is an abnormal mass of tissue resulting from the abnormal growth or division of cells (i.e., neoplasia). Solid tumors are characterized by an absence of liquid areas. In some embodiments, the solid tumor is benign. In some embodiments, the solid tumor is malignant (i.e., a cancer).

In some embodiments, the solid tumor is a sarcoma, or carcinoma.

In some embodiments, the solid tumor is a sarcoma. Sarcomas are cancers of the bone, cartilage, fat, muscle, blood vessels, or other connective or supportive tissue. Sarcomas include, but are not limited to, alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor;

extraskeletal myxoid chondrosarcoma; extrasketetal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma.

In some embodiments, the solid tumor is a carcinoma. Carcinomas are cancers that begin in the epithelial cells. Carcinomas are classified as adenocarcinoma, squamous cell carcinoma, adenosquamous carcinoma, anaplastic carcinoma, large cell carcinoma, small cell carcinoma. By way of non-limiting example, carcinomas include, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer (e.g., basal cell carcinoma, squamous cell carcinoma, malignant melanoma); stomach cancer; testicular cancer; throat cancer; thyroid cancer; uterine cancer; vaginal cancer; or vulvar cancer.

In some embodiments, the solid tumor is breast cancer. In some embodiments, the breast cancer is invasive ductal carcinoma (e.g., triple-negative breast cancer), ductal carcinoma in situ, invasive lobular carcinoma, or lobular carcinoma in situ.

In some embodiments, the solid tumor is pancreatic cancer. In some embodiments, the pancreatic cancer is adenocarcinoma, or islet cell carcinoma.

In some embodiments, the solid tumor is colorectal cancer. In some embodiments, the colorectal cancer is adenocarcinoma. In some embodiments, the solid tumor is a colon polyp, for example associated with familial adenomatous polyposis.

In some embodiments, the solid tumor is bladder cancer. In some embodiments, the bladder cancer is transitional cell bladder cancer, squamous cell bladder cancer, or adenocarcinoma.

In some embodiments, the solid tumor is lung cancer. In some embodiments, the lung cancer is a non-small cell lung cancer. In some embodiments, the lung cancer is a small cell lung cancer. In some embodiments, the non-small cell lung cancer is adenocarcinoma, squamous-cell lung carcinoma, or large-cell lung carcinoma. In some embodiments, the lung cancer is large cell lung cancer.

In some embodiments, the solid tumor is prostate cancer. In some embodiments, the prostate cancer is adenocarcinoma or small cell carcinoma.

In some embodiments, the solid tumor is ovarian cancer (e.g., epithelial ovarian cancer).

In some embodiments, the solid tumor is bile duct cancer. In some embodiments, the bile duct cancer is proximal bile duct carcinoma or distal bile duct carcinoma.

Synergistic Effects

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl) phenoxy]ethyl}-1-benzofuran-2-carboxamide (i.e. PCI-24781/abexinostat).

In some embodiments, the co-administration of and ACK inhibitor (e.g., ibrutinib) and an HDAC inhibitor (e.g., abexinostat) results in a synergistic effect for the treatment of a solid tumor (e.g., reduction in the number of tumors, growth/size of tumors, metastasis of tumors)

In some embodiments, co-administration of an ACK inhibitor (e.g., ibrutinib) and an HDAC inhibitor (e.g., abexinostat) is 5%, 10%, 15%, 20%, 25%, 30%, 35%, 40%, 45%, 50%, 55% or 60% more efficacious than administration of an HDAC inhibitor (e.g., abexinostat) alone. In some embodiments, co-administration of an ACK inhibitor (e.g., ibrutinib) and an HDAC inhibitor (e.g., abexinostat) is 50% more efficacious than administration of an HDAC inhibitor (e.g., abexinostat) alone. In some embodiments, co-administration of an ACK inhibitor (e.g., ibrutinib) and an HDAC inhibitor (e.g., abexinostat) is 1.1×, 1.2×, 1.3×, 1.4×, 1.5×, or 1.6× more efficacious than administration of an HDAC inhibitor (e.g., abexinostat) alone. In some embodiments, co-administration of an ACK inhibitor (e.g., ibrutinib) and an HDAC inhibitor (e.g., abexinostat) is 1.5× more efficacious than administration of an HDAC inhibitor (e.g., abexinostat) alone.

In some embodiments, co-administration of an ACK inhibitor (e.g., ibrutinib) and an HDAC inhibitor (e.g., abexinostat) is 5%, 10%, 15%, 20%, 25%, 30%, or 35% more efficacious than administration of an ACK inhibitor (e.g., ibrutinib) alone. In some embodiments, co-administration of an ACK inhibitor (e.g., ibrutinib) and an HDAC inhibitor (e.g., abexinostat) is 25% more efficacious than administration of an ACK inhibitor (e.g., ibrutinib) alone. In some embodiments, co-administration of an ACK inhibitor (e.g., ibrutinib) and an HDAC inhibitor (e.g., abexinostat) is 1.1×, 1.15×, 1.2×, 1.25×, or 1.3× more efficacious than administration of an ACK inhibitor (e.g., ibrutinib) alone. In some embodiments, co-administration of an ACK inhibitor (e.g., ibrutinib) and an HDAC inhibitor (e.g., abexinostat) is 1.25× more efficacious than administration of an ACK inhibitor (e.g., ibrutinib) alone.

In some embodiments, co-administration of ibrutinib and abexinostat is 5%, 10%, 15%, 20%, 25%, 30%, 35%, 40%, 45%, 50%, 55% or 60% more efficacious than administration of abexinostat alone. In some embodiments, co-administration of ibrutinib and abexinostat is 50% more efficacious than administration of abexinostat alone. In some embodiments, co-administration of ibrutinib and abexinostat is 1.1×, 1.2×, 1.3×, 1.4×, 1.5×, or 1.6× more efficacious than administration of abexinostat alone. In some embodiments, co-administration of ibrutinib and abexinostat is 1.5× more efficacious than administration of abexinostat alone.

In some embodiments, co-administration of ibrutinib and abexinostat is 5%, 10%, 15%, 20%, 25%, 30%, or 35% more efficacious than administration of ibrutinib alone. In some embodiments, co-administration of ibrutinib and abexinostat is 25% more efficacious than administration of ibrutinib alone. In some embodiments, co-administration of ibrutinib and abexinostat is 1.1×, 1.15×, 1.2×, 1.25×, or 1.3× more efficacious than administration of ibrutinib alone. In some embodiments, co-administration of ibrutinib and abexinostat is 1.25× more efficacious than administration of ibrutinib alone.

Administration

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

In some embodiments, the ACK inhibitor compound (e.g., a BTK inhibitor, such as for example, an irreversible BTK inhibitor, such as for example, ibrutinib) and the HDAC inhibitor are administered in the same composition. In some embodiments, the ACK inhibitor compound (e.g., a BTK inhibitor, such as for example an irreversible BTK inhibitor, such as for example ibrutinib) and the HDAC inhibitor are not administered in the same composition. In some embodiments, the ACK inhibitor compound (e.g., a BTK inhibitor, such as for example an irreversible BTK inhibitor, such as for example ibrutinib) and the HDAC inhibitor are administered by different routes. In some embodiments, the ACK inhibitor compound (e.g., a BTK inhibitor, such as for example an irreversible BTK inhibitor, such as for example ibrutinib) and the HDAC inhibitor are administered simultaneously or sequentially.

If simultaneously, the multiple therapeutic agents are optionally provided in a single, unified form, or in multiple forms (by way of example only, either as a single pill or as two separate pills). In some embodiments, one of therapeutic agents is given in multiple doses, or both are given as multiple doses. If not simultaneous, the timing between the multiple doses is from about more than zero weeks to less than about four weeks.

In some embodiments, the ACK inhibitor compound (e.g., a BTK inhibitor, such as for example an irreversible BTK inhibitor, such as for example ibrutinib) and the HDAC inhibitor are administered in a combined dosage form, or in separate dosage forms intended for substantially simultaneous administration. In some embodiments, the ACK inhibitor compound (e.g., a BTK inhibitor, such as for example an irreversible BTK inhibitor, such as for example ibrutinib) and the HDAC inhibitor are administered sequentially, with either therapeutic compound being administered by a regimen calling for two-step administration. In some embodiments, the two-step administration regimen calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval.

The ACK inhibitor compound (e.g., a BTK inhibitor, such as for example an irreversible BTK inhibitor, such as for example ibrutinib) and the HDAC inhibitor compounds described herein are administered before, during or after the development of a solid tumor. In some embodiments, the ACK inhibitor compound (e.g., a BTK inhibitor, such as for example an irreversible BTK inhibitor, such as for example ibrutinib) and the HDAC inhibitor compounds are used as a prophylactic and are administered continuously to subjects with a propensity to develop a solid tumor. In some embodiments, the ACK inhibitor compound (e.g., a BTK inhibitor, such as for example an irreversible BTK inhibitor, such as for example ibrutinib) and the HDAC inhibitor compounds are administered to an individual during or as soon as possible after the development of a solid tumor. In some embodiments, the administration of the ACK inhibitor compound (e.g., a BTK inhibitor, such as for example an irreversible BTK inhibitor, such as for example ibrutinib) and the HDAC inhibitor compounds is initiated within the first 48 hours of the onset of the symptoms, within the first 6 hours of the onset of the symptoms, or within 3 hours of the onset of the symptoms. In some embodiments, the initial administration of the ACK inhibitor compound (e.g., a BTK inhibitor, such as for example an irreversible BTK inhibitor, such as for example ibrutinib) and the HDAC inhibitor compounds is via any route practical, such as, for example, an intravenous injection, a bolus injection, infusion over 5 minutes to about 5 hours, a pill, a capsule, transdermal patch, buccal delivery, and the like, or combination thereof. The ACK inhibitor compound (e.g., a BTK inhibitor, such as for example an irreversible BTK inhibitor, such as for example ibrutinib) and the HDAC inhibitor compounds should be administered as soon as is practicable after the onset of a disorder is detected or suspected, and for a length of time necessary for the treatment of the disease, such as, for example, from about 1 month to about 3 months. The length of treatment can vary for each subject, and the length can be determined using the known criteria. In some embodiments, the ACK inhibitor compound (e.g., a BTK inhibitor, such as for example an irreversible BTK inhibitor, such as for example ibrutinib) and the HDAC inhibitor compounds are administered for at least 2 weeks, between about 1 month to about 5 years, or from about 1 month to about 3 years.

Therapeutically effective amounts will depend on the severity and course of the disorder, previous therapy, the patient's health status, weight, and response to the drugs, and the judgment of the treating physician. Prophalactically effective amounts depend on the patient's state of health, weight, the severity and course of the disease, previous therapy, response to the drugs, and the judgment of the treating physician.

In some embodiments, the ACK inhibitor compound (e.g., a BTK inhibitor, such as for example an irreversible BTK inhibitor, such as for example ibrutinib) and HDAC inhibitor compounds are administered to the patient on a regular basis, e.g., three times a day, two times a day, once a day, every other day or every 3 days. In other embodiments, the ACK inhibitor compound (e.g., a BTK inhibitor, such as for example an irreversible BTK inhibitor, such as for example ibrutinib) ACK inhibitor compound (e.g., a BTK inhibitor, such as for example an irreversible BTK inhibitor, such as for example ibrutinib) and HDAC inhibitor compounds are administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the ACK inhibitor compound (e.g., a BTK inhibitor, such as for example an irreversible BTK inhibitor, such as for example ibrutinib) and HDAC inhibitor compounds are administered only when the patient exhibits a particular symptom, e.g., the onset of pain, or the onset of a fever, or the onset of an inflammation, or the onset of a skin disorder. Dosing schedules of each compound may depend on the other or may be independent of the other.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance regimen is administered if necessary. Subsequently, the dosage or the frequency of administration, or both, of one or both of the ACK inhibitor compound (e.g., a BTK inhibitor, such as for example an irreversible BTK inhibitor, such as for example ibrutinib) and HDAC inhibitor compounds can be reduced, as a function of the symptoms, to a level at which the individual's improved condition is retained. Individuals can, however, require intermittent treatment on a long-term basis upon any recurrence of symptoms.

The amount of the ACK inhibitor compound (e.g., a BTK inhibitor, such as for example an irreversible BTK inhibitor, such as for example ibrutinib) and HDAC inhibitor compounds will vary depending upon factors such as the particular compound, disorder and its severity, the identity (e.g., weight) of the subject or host in need of treatment, and is determined according to the particular circumstances surrounding the case, including, e.g., the specific agents being administered, the routes of administration, the solid tumor being treated, and the subject or host being treated. In general, however, doses employed for adult human treatment will typically be in the range of 0.02-5000 mg per day, or from about 1-1500 mg per day of each compound. The desired dose of each compound may be presented in a single dose or as divided doses administered simultaneously (or over a short period of time) or at appropriate intervals, for example as two, three, four or more sub-doses per day.

In some embodiments, the amount of the ACK inhibitor (e.g., a BTK inhibitor, such as for example an irreversible BTK inhibitor, such as for example ibrutinib) is from 300 mg/day up to, and including, 1000 mg/day. In some embodiments, the amount of the irreversible Btk inhibitor is from 420 mg/day up to, and including, 840 mg/day. In some embodiments, the amount of the irreversible Btk inhibitor is about 420 mg/day, about 560 mg/day, or about 840 mg/day. In some embodiments, the amount of the irreversible Btk inhibitor is about 420 mg/day.

In some embodiments, the HDAC inhibitor (e.g., abexinostat) is administered for 4 consecutive days, followed by three consecutive days without administration of the HDAC inhibitor (e.g., abexinostat).

The ACK inhibitor compound (e.g., a BTK inhibitor, such as for example an irreversible BTK inhibitor, such as for example ibrutinib) and HDAC inhibitor compounds described herein may be individually or combined into unit dosage forms suitable for single administration of precise dosages. In unit dosage form, the formulation is divided into unit doses containing appropriate quantities of one or both compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

It is understood that a medical professional will determine the dosage regimen in accordance with a variety of factors. These factors include the solid tumor from which the subject suffers, the degree of metastasis, as well as the age, weight, sex, diet, and medical condition of the subject.

Compounds

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound.

Definition of standard chemistry terms are found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —$CH_2$— group; and an ethylene is a diradical of an ethyl group, i.e., —$CH_2CH_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, isobutyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=$CH_2$, —C($CH_3$)=$CH_2$, —CH=CH$CH_3$, —C($CH_3$)=CH$CH_3$. Alkenylene groups include, but are not limited to, —CH=CH—, —C($CH_3$)=CH—, —CH=CH$CH_2$—, —CH=CH$CH_2CH_2$— and —C($CH_3$)=CH$CH_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡C$CH_3$, —C≡C$CH_2CH_3$, and —C≡C$CH_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkylhydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)2-, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

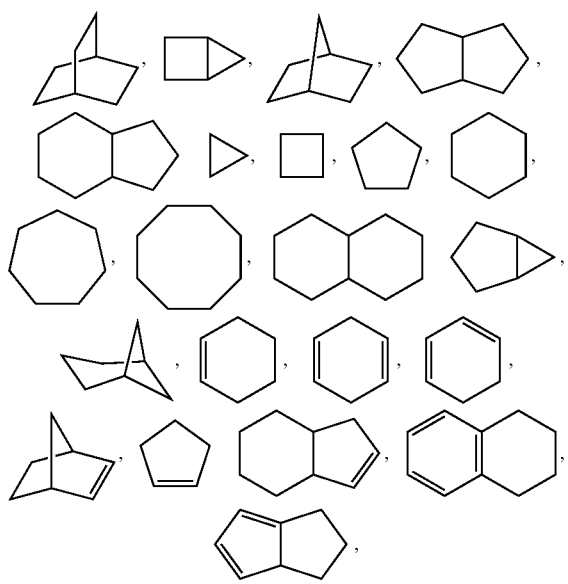

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

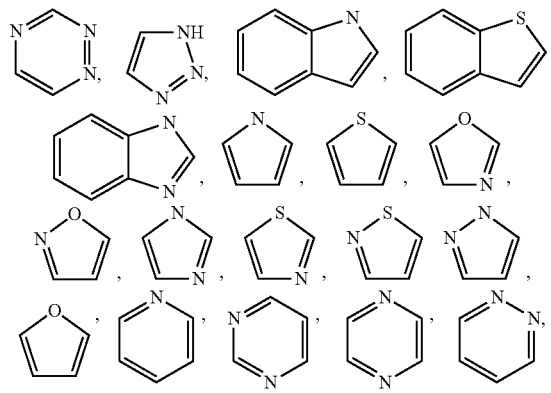

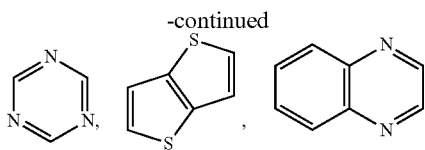

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

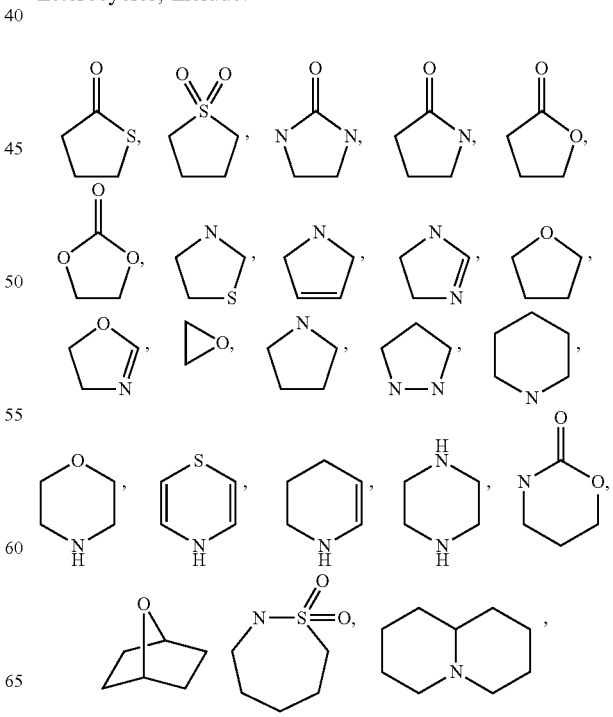

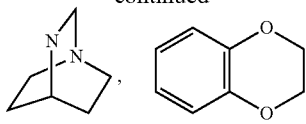

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, in some embodiments, up to two heteroatoms are consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$alkyl), (substituted or unsubstituted $C_3$-$C_6$cycloalkyl), heteroaryl, or heteroalkyl. The protecting groups that form the protective derivatives of the above substituents include those found in sources such as Greene and Wuts, above.

ACK Inhibitor Compounds

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

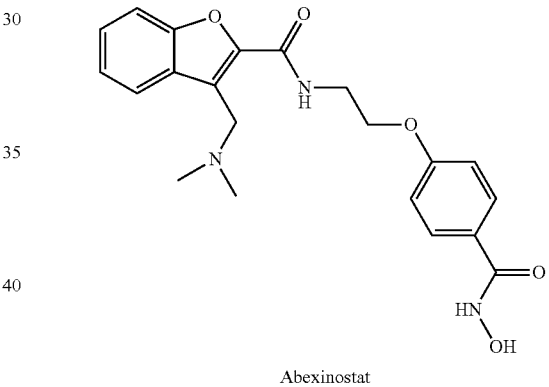

Abexinostat

The ACK inhibitor compounds described herein are selective for kinases having an accessible cysteine that is able to form a covalent bond with a Michael acceptor moiety on the inhibitor compound. In some embodiments, the cysteine residue is accessible or becomes accessible when the binding site moiety of the irreversible inhibitor binds to the kinase. That is, the binding site moiety of the irreversible inhibitor binds to an active site of the ACK and the Michael acceptor moiety of irreversible inhibitor gains access (in one embodiment the step of binding leads to a conformational change in the ACK, thus exposing the cysteine) or is otherwise exposed to the cysteine residue of the ACK; as a result a covalent bond is formed between the "S" of the cysteine residue and the Michael acceptor of the irreversible inhibitor. Consequently, the binding site moiety of the irreversible inhibitor remains bound or otherwise blocks the active site of the ACK.

In one embodiment, the ACK is Btk, a homolog of Btk or a tyrosine kinase having a cysteine residue in an amino acid sequence position that is homologous to the amino acid sequence position of cysteine 481 in Btk. In some embodiments, the ACK is HER4 Inhibitor compounds described herein include a Michael acceptor moiety, a binding site moiety and a linker that links the binding site moiety and the Michael acceptor moiety (and in some embodiments, the structure of the linker provides a conformation, or otherwise directs the Michael acceptor moiety, so as to improve the selectivity of the irreversible inhibitor for a particular ACK).

In some embodiments, the ACK inhibitor is a compound of Formula (A):

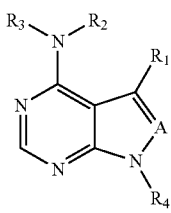

Formula (A)

wherein
A is independently selected from N or $CR_5$;
$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);
$R_2$ and $R_3$ are independently selected from H, lower alkyl and substituted lower alkyl;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_1$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;
G is

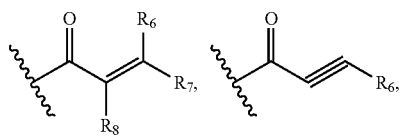

-continued

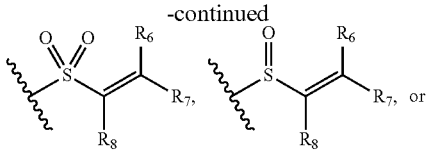

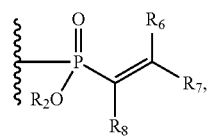

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_9$ and $R_{10}$ can together form a 5-, 6-, 7-, or 8-membered heterocyclic ring; or
each $R_{11}$ is independently selected from H, —S(=O)$_2$R$_8$, —S(=O)$_2$NH$_2$, —C(O)R$_8$, —CN, —NO$_2$, heteroaryl, or heteroalkyl; and
pharmaceutically active metabolites, pharmaceutically acceptable solvates, pharmaceutically acceptable salts, or pharmaceutically acceptable prodrugs thereof.

In some embodiments, the ACK inhibitor is R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

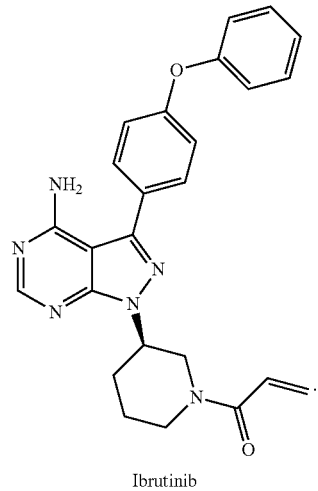 [SMILES: C=CC(=O)N1CCC[C@@H](n2nc(-c3ccc(Oc4ccccc4)cc3)c3c(N)ncnc32)C1]

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited).

In some embodiments, the ACK inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3,3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066).

In some embodiments, the ACK inhibitor is:

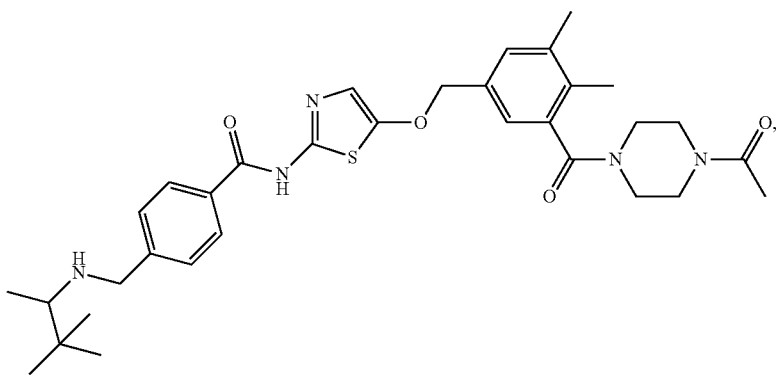

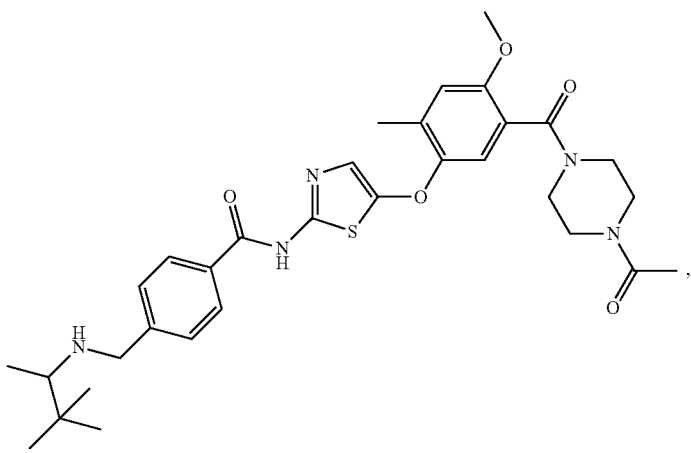

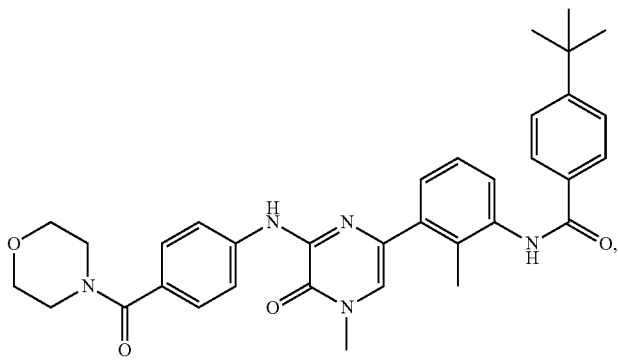

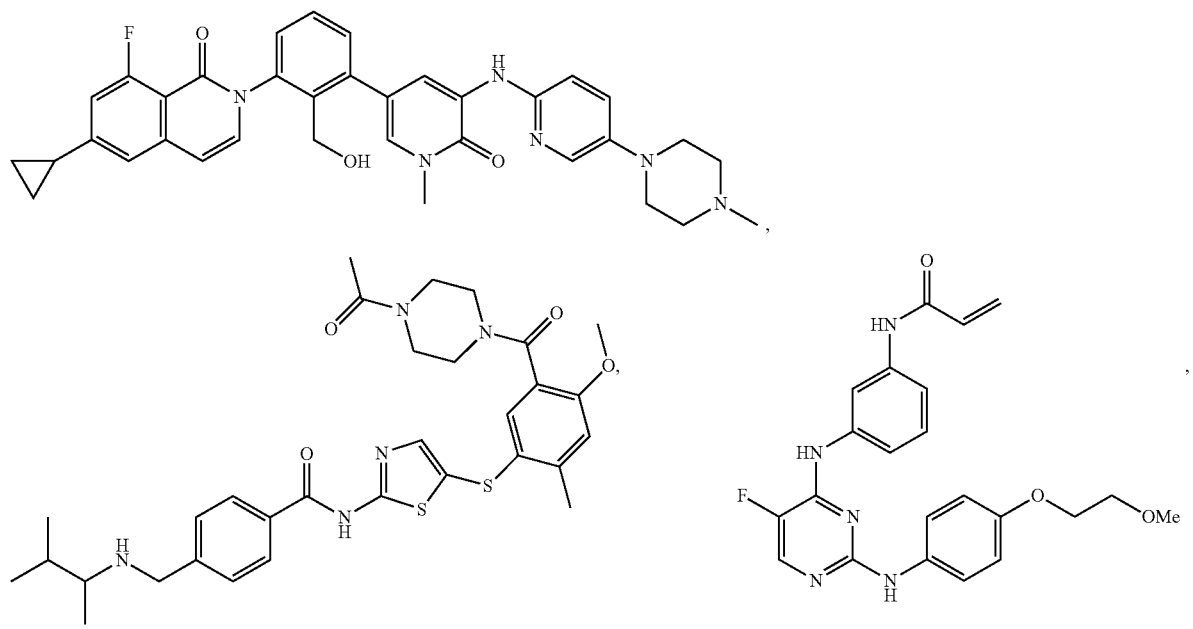
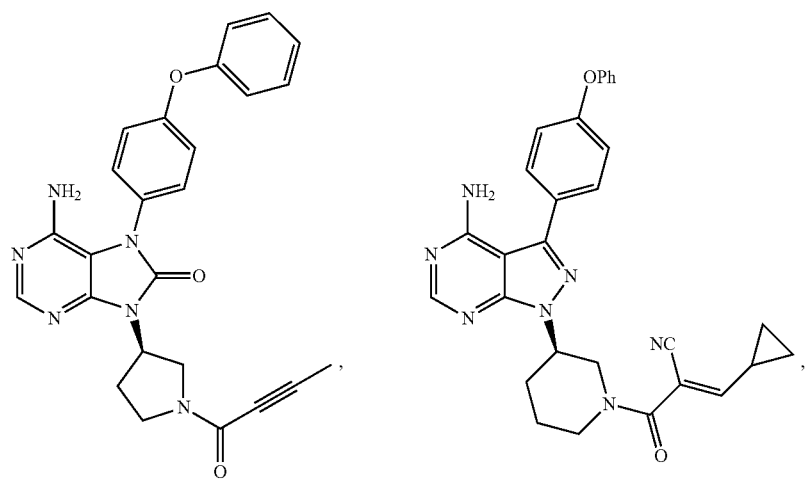
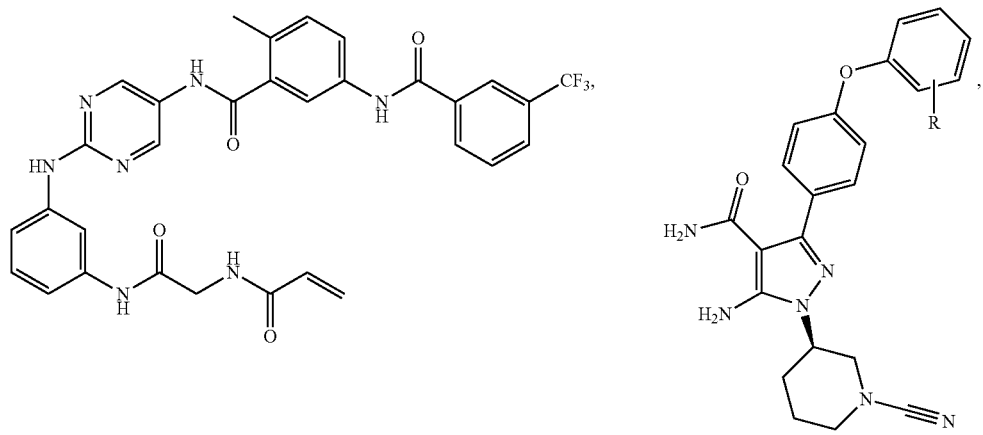

-continued
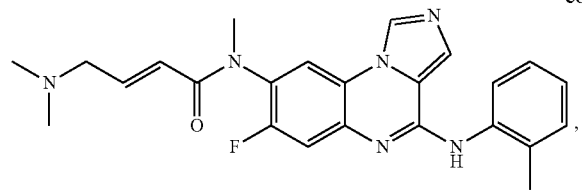
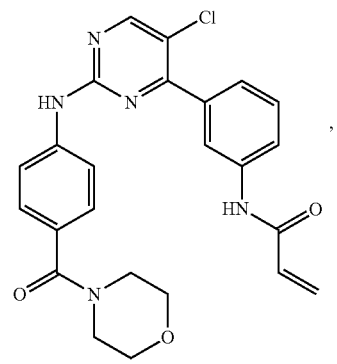
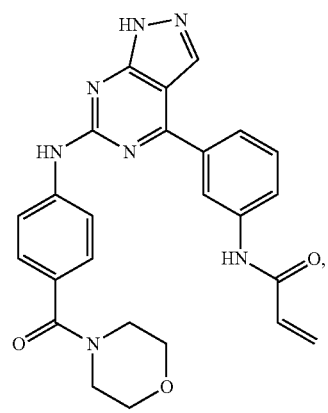
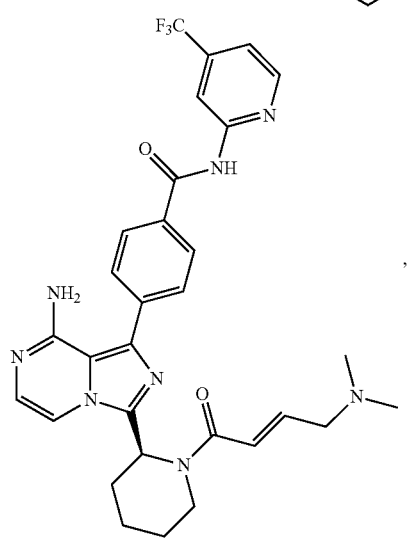
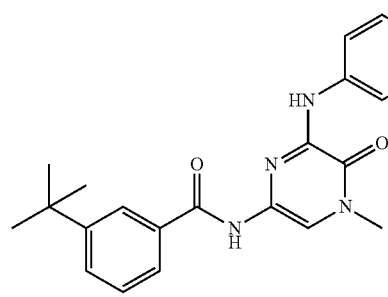
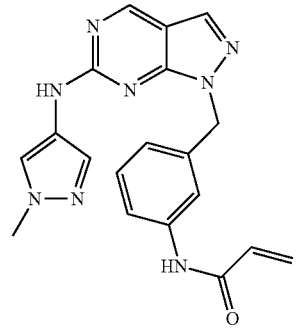
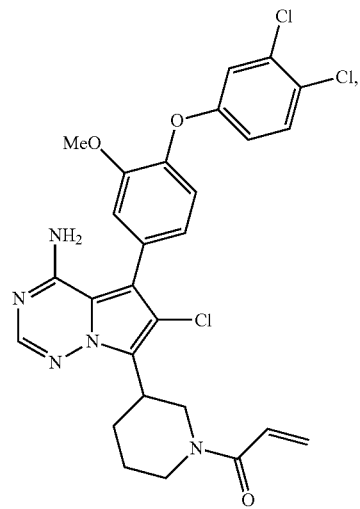
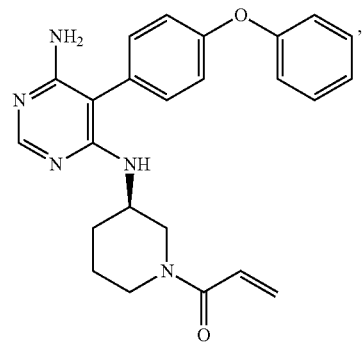

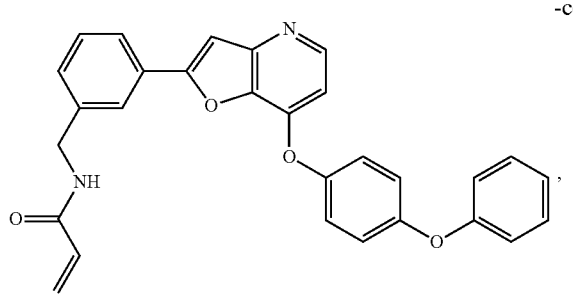, or 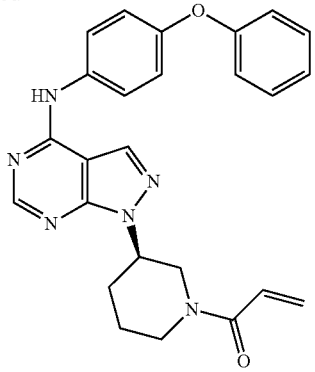

HDAC Inhibitor Compounds

Described herein methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib).

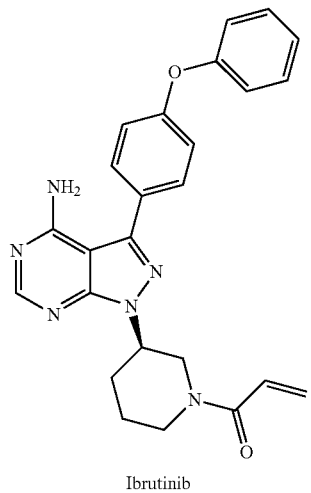 [SMILES: C=CC(=O)N1CCC[C@@H](n2nc(-c3ccc(Oc4ccccc4)cc3)c3c(N)ncnc32)C1]

Ibrutinib

In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited).

In some embodiments, the HDAC inhibitor has the structure of Formula (B):

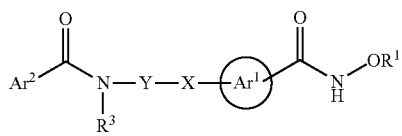

Formula (B)

wherein:

$R^1$ is hydrogen or alkyl;

X is —O—, —NR$^2$—, or —S(O)$_n$— where n is 0-2 and $R^2$ is hydrogen or alkyl;

Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

$Ar^1$ is phenylene or heteroarylene wherein said $Ar^1$ is optionally substituted with one or two groups independently selected from alkyl, halo, hydroxy, alkoxy, haloalkoxy, or haloalkyl;

$R^3$ is hydrogen, alkyl, hydroxyalkyl, or optionally substituted phenyl; and $Ar^2$ is aryl, aralkyl, aralkenyl, heteroaryl, heteroaralkyl, heteroaralkenyl, cycloalkyl, cycloalkylalkyl, heterocycloalkyl, or heterocycloalkylalkyl;

and individual stereoisomers, individual geometric isomers, or mixtures thereof; or a pharmaceutically acceptable salt thereof.

In some embodiments, the histone deacetylase inhibitor is 3-((dimethylamino)methyl)-N-(2-(4-(hydroxycarbamoyl)phenoxy)ethyl)benzofuran-2-carboxamide (i.e. PCI-24781/abexinostat).

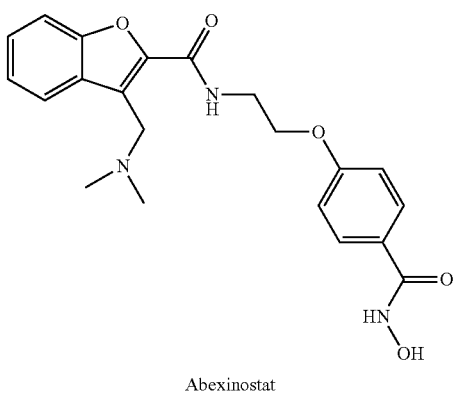 [SMILES: CN(C)Cc1c(C(=O)NCCOc2ccc(C(=O)NO)cc2)oc2ccccc12]

Abexinostat

Pharmaceutical Compositions/Formulations

Disclosed herein, in certain embodiments, are compositions comprising a therapeutically effective amount of an ACK inhibitor compound and/or a therapeutically effective amount of an HDAC inhibitor compound, and a pharmaceutically acceptable excipient. Further disclosed herein, in certain embodiments, are compositions comprising a therapeutically effective amount of an ACK inhibitor compound, a therapeutically effective amount of an HDAC inhibitor compound, and a pharmaceutically acceptable excipient. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

Pharmaceutical compositions of ACK inhibitor compound (e.g., a BTK inhibitor, such as for example an irreversible BTK inhibitor, such as for example ibrutinib) and/or HDAC inhibitor compound are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of an ACK inhibitor compound (e.g., a BTK inhibitor, such as for example an irreversible BTK inhibitor, such as for example ibrutinib) and/or HDAC inhibitor compound with other chemical components, such as carriers, stabilizers, diluents, dispersing agents, suspending agents, thickening agents, and/or excipients.

Pharmaceutical compositions are optionally manufactured in a conventional manner, such as, by way of example only, by means of conventional mixing, dissolving, granulating, dragee-making, levigating, emulsifying, encapsulating, entrapping or compression processes.

The pharmaceutical formulations described herein are administered by any suitable administration route, including but not limited to, oral, parenteral (e.g., intravenous, subcutaneous, intramuscular), intranasal, buccal, topical, rectal, or transdermal administration routes.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In some embodiments, the pharmaceutical compositions are formulated such that the amount of the ACK inhibitor (e.g., a BTK inhibitor, such as for example an irreversible BTK inhibitor, such as for example ibrutinib) in each unit dosage form is about 140 mg per.

Kits/Articles of Manufacture

Described herein are methods of treating solid tumors comprising co-administering an ACK inhibitor compound (e.g., a BTK inhibitor, such as for example an irreversible BTK inhibitor, such as for example ibrutinib) and an HDAC inhibitor compound. In some embodiments, the ACK inhibitor compound (e.g., a BTK inhibitor, such as for example an irreversible BTK inhibitor, such as for example ibrutinib) is a compound of Formula (A). In some embodiments, the ACK inhibitor compound is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the ACK inhibitor is AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited). In some embodiments, the HDAC inhibitor is a compound of Formula (B). In some embodiments, the HDAC inhibitor is 3-[(dimethylamino)methyl]-N-{2-[4-(hydroxycarbamoyl)phenoxy]ethyl}-1-benzofuran-2-carboxamide (i.e. PCI-24781/abexinostat).

For use in therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of Btk, or in which Btk is a mediator or contributor to the symptoms or cause.

For example, a container may include one or both of the irreversible BTK inhibitor and HDAC inhibitor compounds. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising one or both the ACK inhibitor compound (e.g., a BTK inhibitor, such as for example an irreversible BTK inhibitor, such as for example ibrutinib) and the HDAC inhibitor compounds is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Example 1

The aim of the experiment is to evaluate the effect of two drugs on tumor development in a mouse model of non-small cell lung cancer.

The two drugs tested were Abexinostat (PCI-24781), and Ibrutinib (PCI-32765).

Grg1 transgenic mice were used to evaluate the drugs. Grg1 transgenic mice overexpress the Groucho-related gene 1 (Grg1). The mice develop lung tumors that resemble human non-small cell lung cancer. Tumors initiate at 1 month of age and progress to invasive adenocarcinoma by 8 months of age. The drugs were administered to 2 month-old mice or to 5 month-old mice, and mice were treated for 4 weeks. The former group is referred to as the 3 month samples and the latter as the 6 month samples.

Summary

Drug treatment of 2 to 3 month old mice reduced tumor number compared to the control group. The combination of abexinostat and ibrutinib reduced tumor number by 75%.

With the combination of abexinostat and ibrutinib treatment for 5 to 6 months, there were no large tumors.

Methods a. Mice

Mice were housed and treated following the applicable Standard Operating Procedures and according to the Canadian Animal Care Committee standards.

Mice were bred to generate double transgenic (Grg1/Cre recombinase) mice on a CD1 background. Four groups of female double transgenic mice were established:

Group 1—Control (no treatment, injection of PBS, or water with carrier and no drug)

Group 2—Abexinostat—treated

Group 3—Ibrutinib—treated

Group 4—Abexinostat+Ibrutinib—treated

At least 8 mice in each group were treated at 2 months old and 8 mice in each group were treated at 5 months old. Treatments lasted 4 weeks, and mice were sacrificed at 3 months and 6 months. Therefore samples are referred to as 3 month samples or 6 month samples.

b. Drug Preparation and Dosage

Abexinostat was administered by intraperitoneal (i.p.) injection, twice per day for five days each week. Mice were weighed and injected with 6 µl per gram body weight of a 1 mg/ml solution. The dosage was 12 mg/kg BID.

Ibrutinib was administered by supplying it in the drinking water, for a dosage of ~22 mg/kg/day.

Mice were treated for 4 weeks. After treatment, mice were euthanized and lung tissue was examined.

Drugs were prepared and administered as follows:

Abexinostat

Formulation: Add DMSO to powder stock in vial to make a 200 mg/ml solution. Aliquot out into 100 µl. Every two weeks, as required, thaw a 100 µl aliquot and add 900 µl sterile water. Aliquot into 20 µl aliquots of 20 mg/ml. Store this stock at 4 C.

Dosage

20 µl of 20 mg/ml stock in the fridge; inject at 1 mg/ml concentration in sterile water. On the day of injection, add 380 µl sterile water or PBS and pipet well to mix thoroughly. Inject 6 µl per g body weight TWICE DAILY.

Ibrutinib

Formulation: 100 ml of the 10× concentrate of Ibrutinib. Dilute 1 part of concentrate with 9 parts water. Both the 10× and 1× dilutions can be stored at room temperature. PCI-32765 is >99% stable in this formulation after 6 weeks at room temperature (22° C.).

Dosage

Administered by drinking water; Average consumption is ~4 mL/day/mouse, corresponding to a final dose of ~22 mg/kg/day. Thus 4 ml×4 mice=16 ml/day×7 days=140 ml per week c. Quantitation For quantitation of tumors, the total visible tumors on the lung surface were counted using a dissecting microscope. In addition, the left lung lobe was fixed in 4% PFA, paraffin-embedded and 5 µm sections were taken for 100 µm at two levels. The first level began 30 µm below the lung surface and the second level began 130 µm below the lung surface. Alternate slides were H&E stained, and tumors were detected and counted using a dissecting microscope. Tumor diameter was measured using an inverted microscope and reticule.

The right lung lobes were snap-frozen and stored for DNA or protein analysis.

d. Blood Samples

For 6 month-old mice, blood samples were collected in EDTA tubes, and peripheral blood mononuclear cells (PBMC) and plasma were prepared, frozen and stored as follows:

1. A minimum of 500 µL of blood is drawn into the EDTA tube

2. Transfer the blood into 1.5 mL eppendort tubes and centrifuge at 350×g for 5 minutes to separate the plasma and the cells. Save the supernatant/plasma.

3. Save the supernatant/plasma.

4. Add 1 ml of 1×RBC Lysis Buffer (Sigma #R7757) to the pellet

5. Gently vortex each tube immediately after adding the lysing solution.

6. Incubate at room temperature, protected from light, for 5 minutes.

7. Centrifuge 350×g for 2 minutes.

8. Aspirate supernatant without disturbing pellet.

9. Wash the pellet once with 1 mL of PBS to the sample and centrifuge 350×g for 2 minutes 10. Aspirate supernatant without disturbing the pellet.

11. Freeze the PBMC pellet at ~80 C

Results a. Three Month Old

Figure 2:
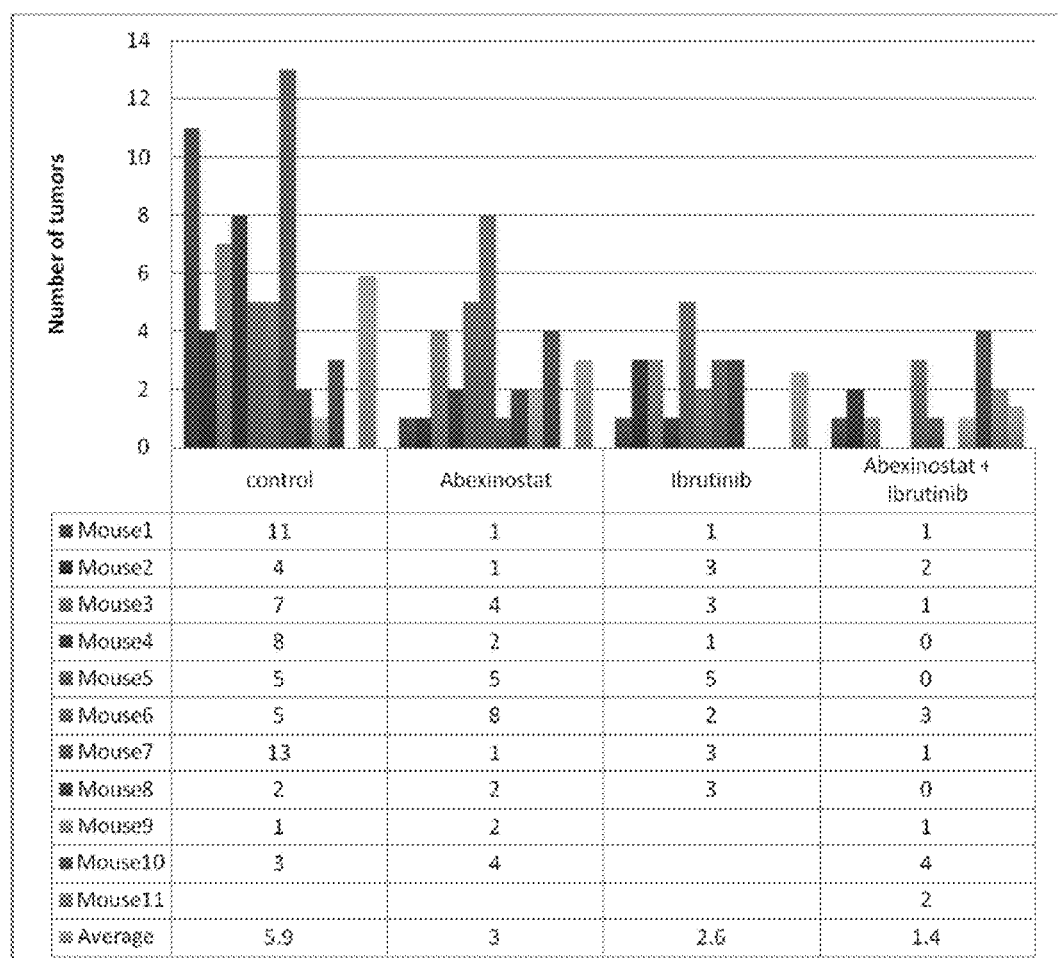
FIG. 2: Is an illustrative example of the number of surface tumors per Grg1 transgenic mice at 3 months after 4 weeks of treatment with abexinostat, ibrutinib, or the combination of abexinostat and ibrutinib.

The total number of surface tumors visible at 3 months, after 4 weeks of treatment, is shown in a table and corresponding bar graph in FIG. 2. Each number in the table represents the number of tumors in one mouse. The average number of tumors per mouse for each treatment is shown in the bottom row of the table and right-most bar for each group. For the control group, the average number of tumors was 5.9 (n=10). For the Abexinostat-treated mice, the average tumor number was 3.0 (n=10), for Ibrutinib it was 2.6 (n=8), and for treatment with both drugs 1.4 (n=11).

Figure 3:
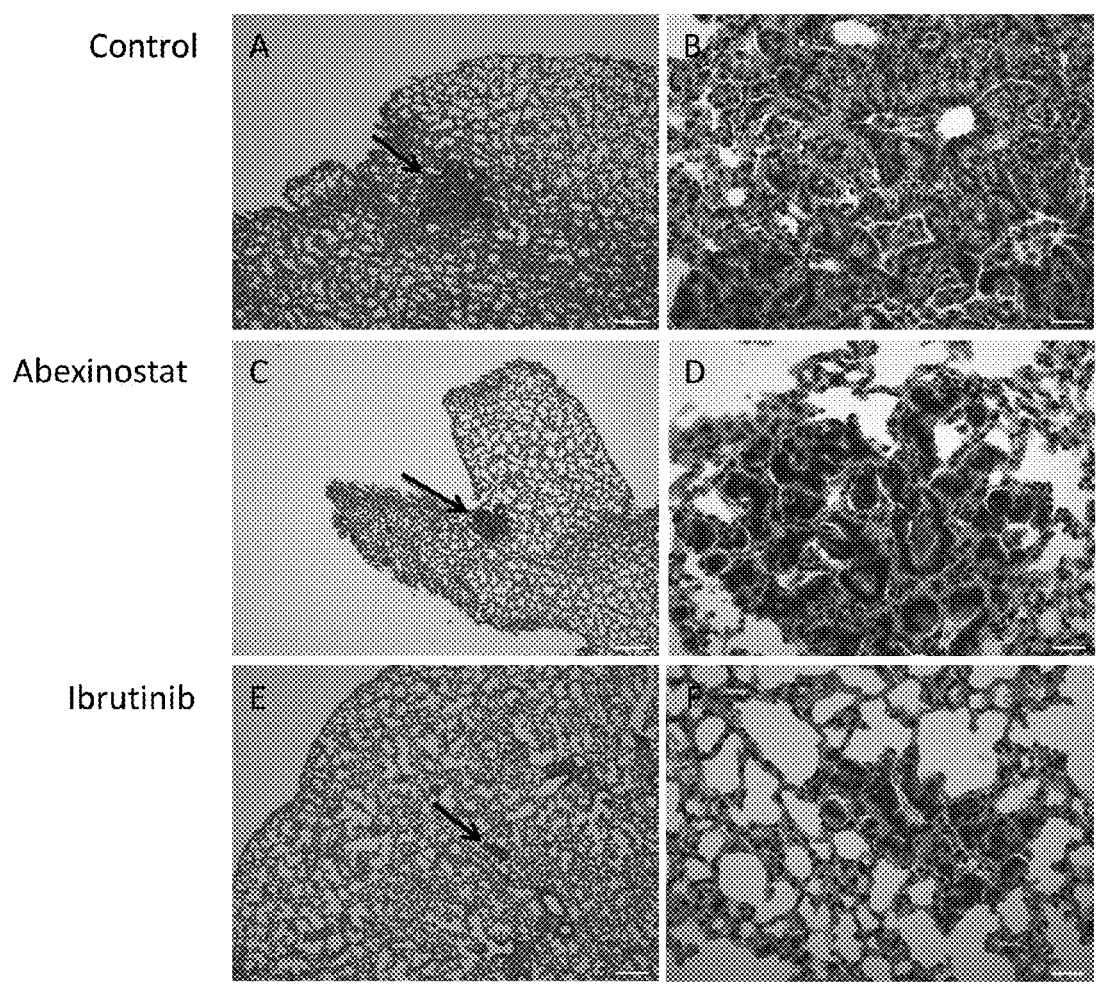
FIG. 3: Is an illustrative example of tumor sections from Grg1 transgenic mice at 3 months. Tumor sections from control mice (A, B), Abexinostat-treated mice (C, D), and Ibrutinib-treated mice (E, F). Arrows in A, C, E point to tumors. Original magnification of images in the left column was 50× and in the right column was 400×.

Tumors in the 3 month samples were further analyzed for four mice in each treatment group by sectioning the left lung lobe, and H&E staining alternate slides. The tumor histology is presented in FIG. 3 and all images are available on disk.

The tumors are carcinoma that are less than 400 The tumor histology appears similar in treated and control mice.

b. Six Month Old

Figure 4:
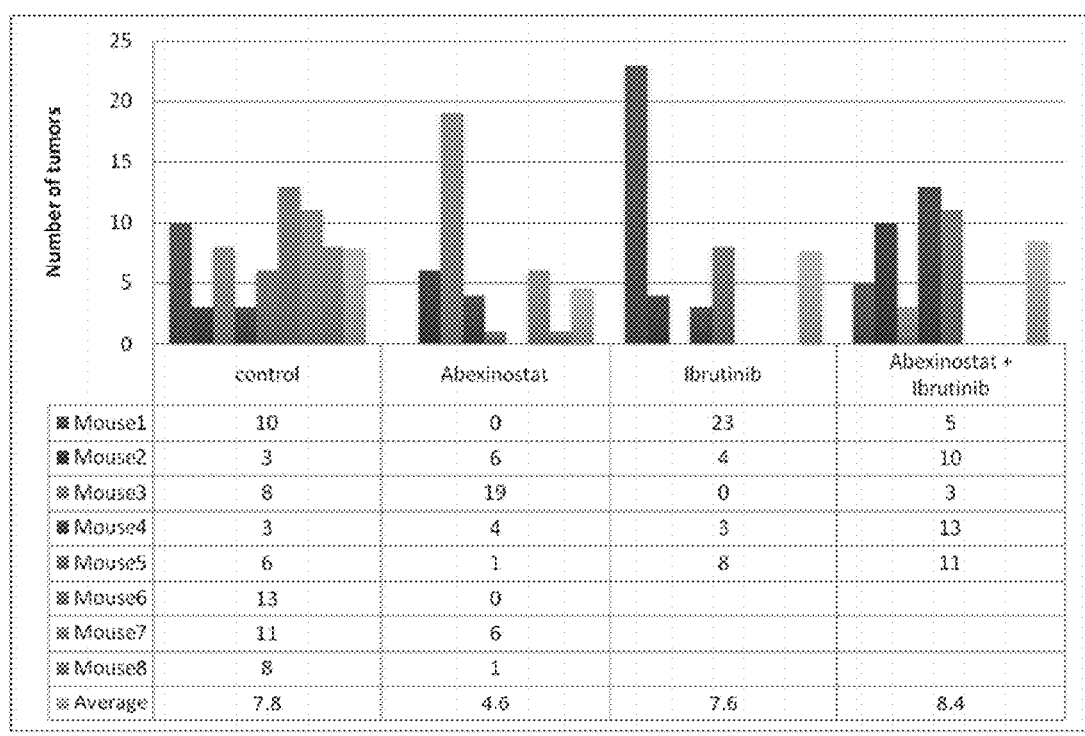
FIG. 4: Is an illustrative example of the number of surface tumors per Grg1 transgenic mice at 6 months after 4 weeks of treatment with abexinostat, ibrutinib, or the combination of abexinostat and ibrutinib.

The total number of surface tumors visible at 6 months, after 4 weeks of treatment, is shown in a table and corresponding bar graph in FIG. 4. Each number in the table represents the number of tumors in one mouse. The average number of tumors per mouse for each treatment is shown in the bottom row and the right-most bar for each group. For the control group, the average number of tumors was 7.8 (n=8). For the Abexinostat-treated mice, the average tumor number was 4.6 (n=8), for Ibrutinib it was 7.6 (n=5), and for treatment with both drugs 8.4 (n=5).

The number of visible surface tumors in the 6 month-old mice was quite variable and did not show a trend between treatment groups.

Figure 5:
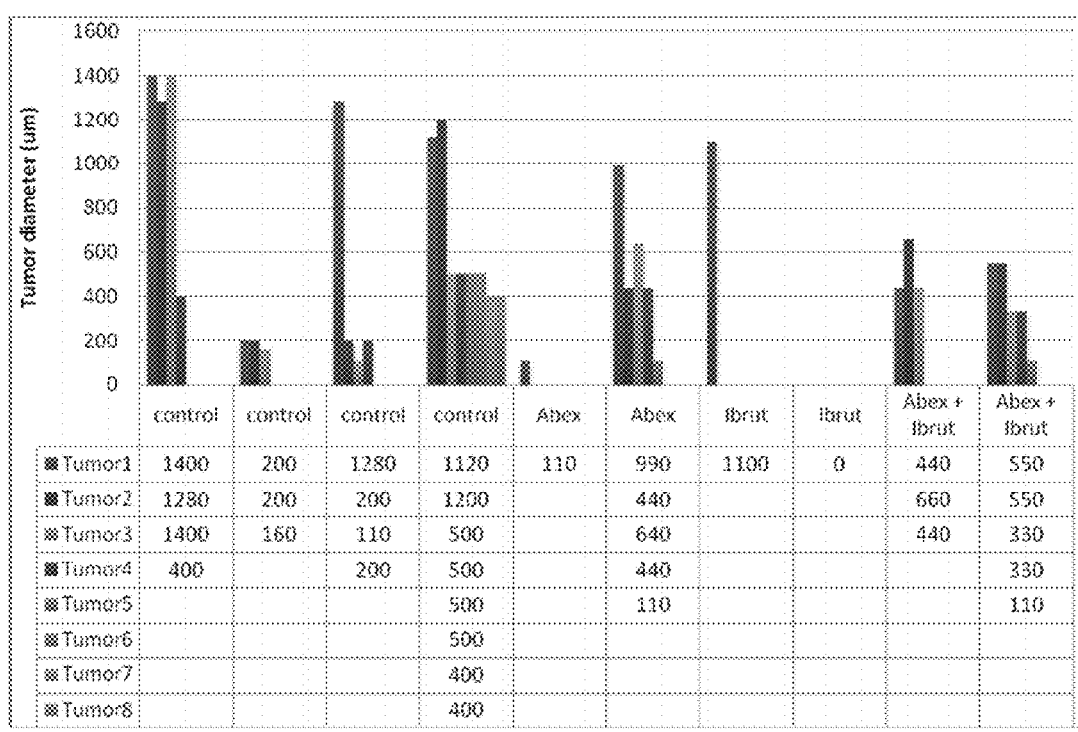
FIG. 5: Is an illustrative example of tumor diameter in tissue sections at 6 months for Grg1 transgenic mice after 4 weeks of treatment with abexinostat, ibrutinib, or the combination of abexinostat and ibrutinib. Each column represents one mouse sample, and the size of each tumor present in the sectioned slides for that mouse sample is given in the column. Each bar in the graph represents the diameter of one tumor and each group of bars represents one mouse. Four mice were analyzed from the control group, and two mice were analyzed for each of the drug-treated groups.

The tumors were further analyzed for two to four mice in each group by sectioning the left lung lobe, and H&E staining alternate slides. To measure and compare the tumor load in the mice in the 6 month samples, the tumor diameter in the tissue sections was measured. The number of tumors in the sections and the size of each tumor is recorded in the table and corresponding bar graph in FIG. 5. Each column in the table and group of bars in the graph shows the tumor sizes for one mouse.

Figure 6:
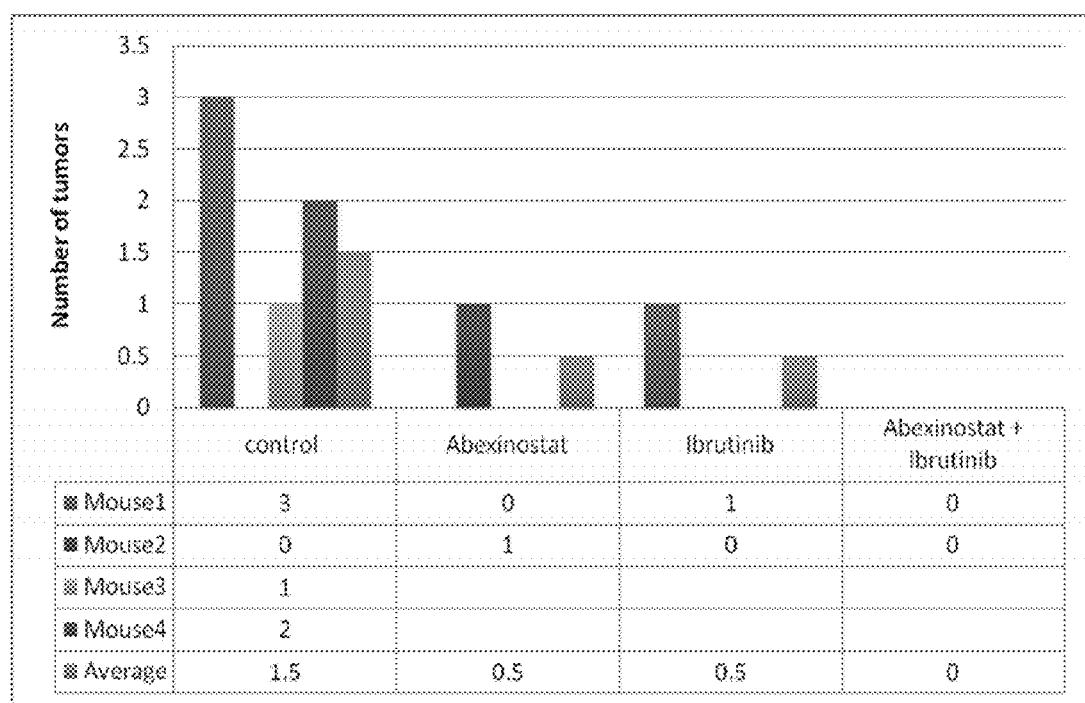
FIG. 6: Is an illustrative example of the number of tumors over 1 mm in 6 month samples from Grg1 transgenic mice after 4 weeks of treatment with abexinostat, ibrutinib, or the combination of abexinostat and ibrutinib. Each number in the table and bar in the graph represents the number of tumors>1 mm for one mouse. The average number of large tumors per mouse for each treatment group is shown in the bottom row of the table and the right-most bar for each group.

The treated mice had fewer large tumors than the control mice. The number of tumors over 1 mm in diameter for each mouse is shown in FIG. 6. Control mice had an average of 1.5 large tumors per mouse, Abexinostat- and Ibrutinib-treated mice had an average of 0.5 large tumors per mouse and Abexinostat+Ibrutinib-treated mice had 0 large tumors per mouse.

Figure 8:
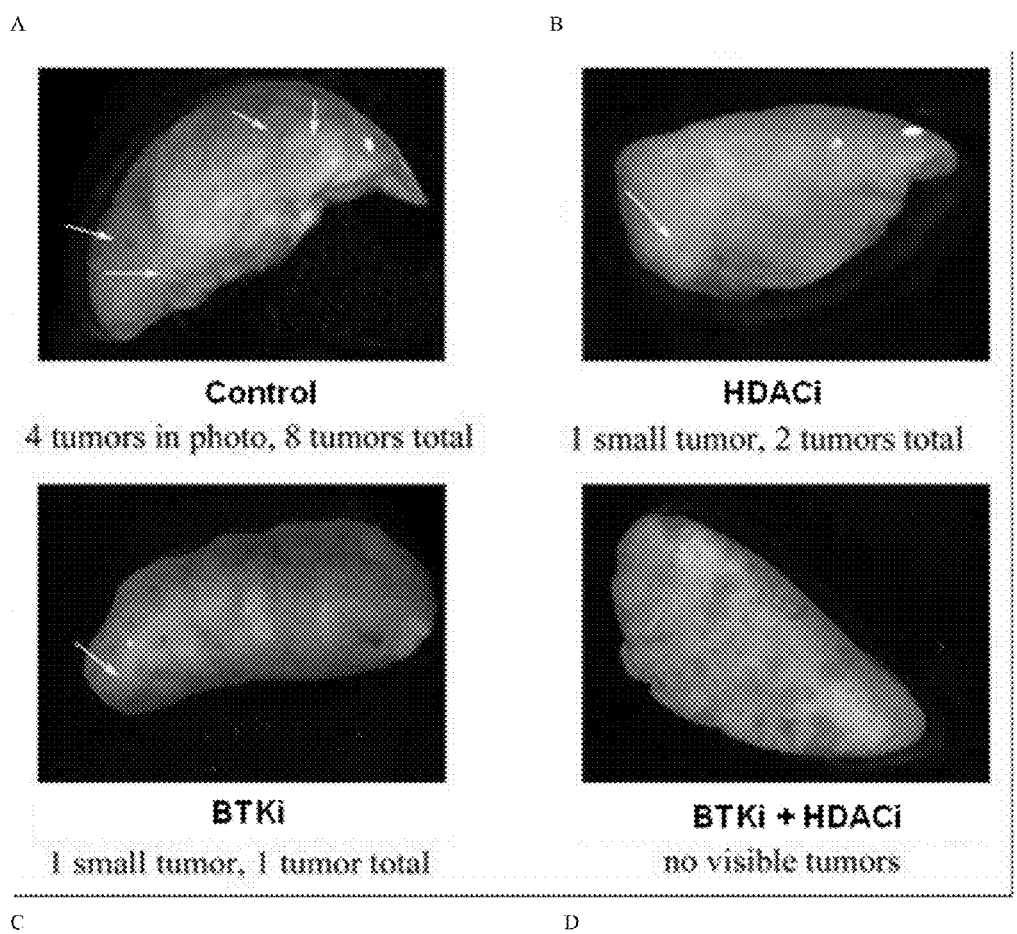
FIG. 8: Is an illustrative example of whole lung lobes from 3 month Grg1 transgenic mice after 4 weeks of treatment with abexinostat, ibrutinib, or the combination of abexinostat and ibrutinib. Four large tumors are visible in the control sample (A); one small tumor is visible in Abexinostat-treated (B) and Ibrutinib-treated (C) samples, and no visible tumors are seen in the Abexinostat+Ibrutinib-treated (D) samples.
Figure 9:
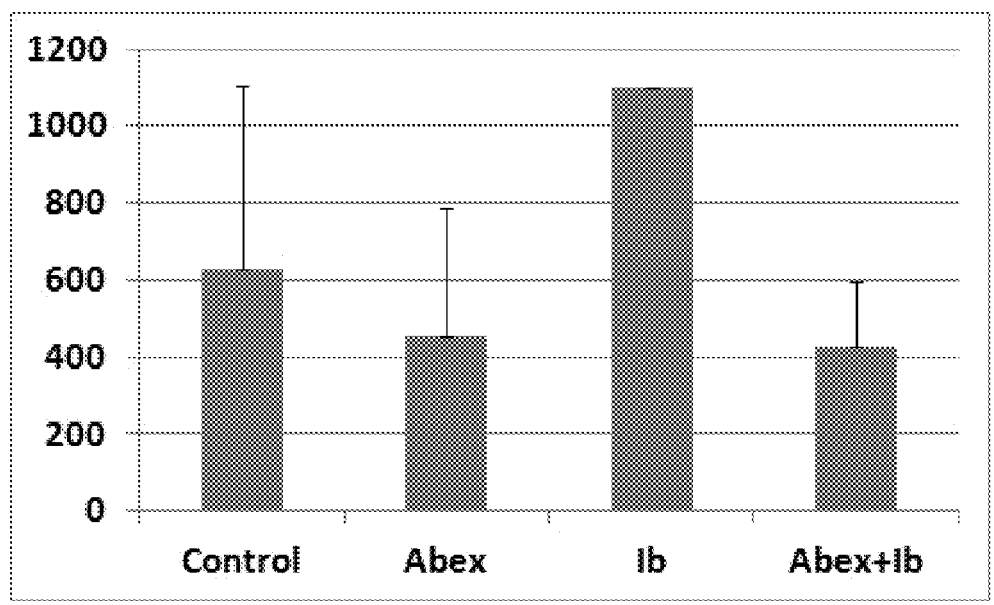
FIG. 9: Is a table exemplifying the effects on tumor diameter in 6 month sections of the combination of abexinostat and ibrutinib. The first bar is the control. The second bar shows the results following treatment with abexinostat alone. The third bar shows the results following treatment with ibrutinib alone. The fourth bar shows the results following treatment with abexinostat and ibrutinib. There were many large tumors in controls compared to treated groups. Interestingly, there were no small tumors in Ib-treated sections, just one large tumor.
Figure 10:
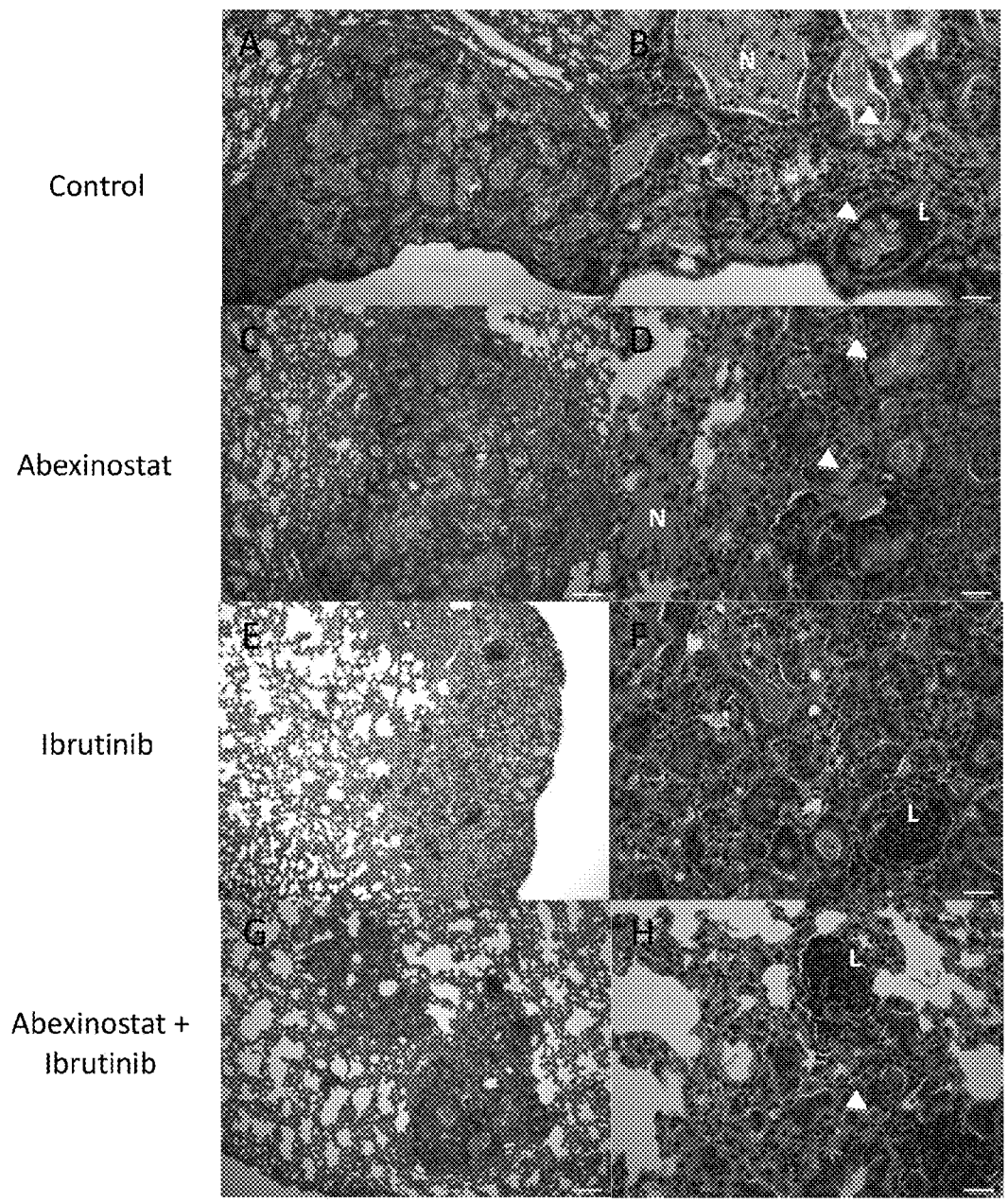
FIG. 10: Is an illustrative example of lung tissue sections from 6 month Grg1 transgenic mice after 4 weeks of treatment with abexinostat, ibrutinib, or the combination of abexinostat and ibrutinib. In the tissue sections, tumors in control mice exhibit lymphocyte infiltration (L), necrosis (N) and a high number of apoptotic macrophages (FIGS. 8A and B). Tumors from Abexinostat-treated mice have lymphocyte infiltration, necrosis and large areas with apoptotic cells (FIGS. 8C and 8D). Tumors from Ibrutinib-treated mice have lymphocyte infiltration but not the apoptotic macrophages seen in the control and in Abexinostat-treated mice (FIGS. 8E and 8F). Tumors from Abexinostat+Ibrutinib-treated mice have lymphocyte infiltration and macrophage present but not a high number of apoptotic macrophage (FIGS. 8G and 8H).
Figure 12:
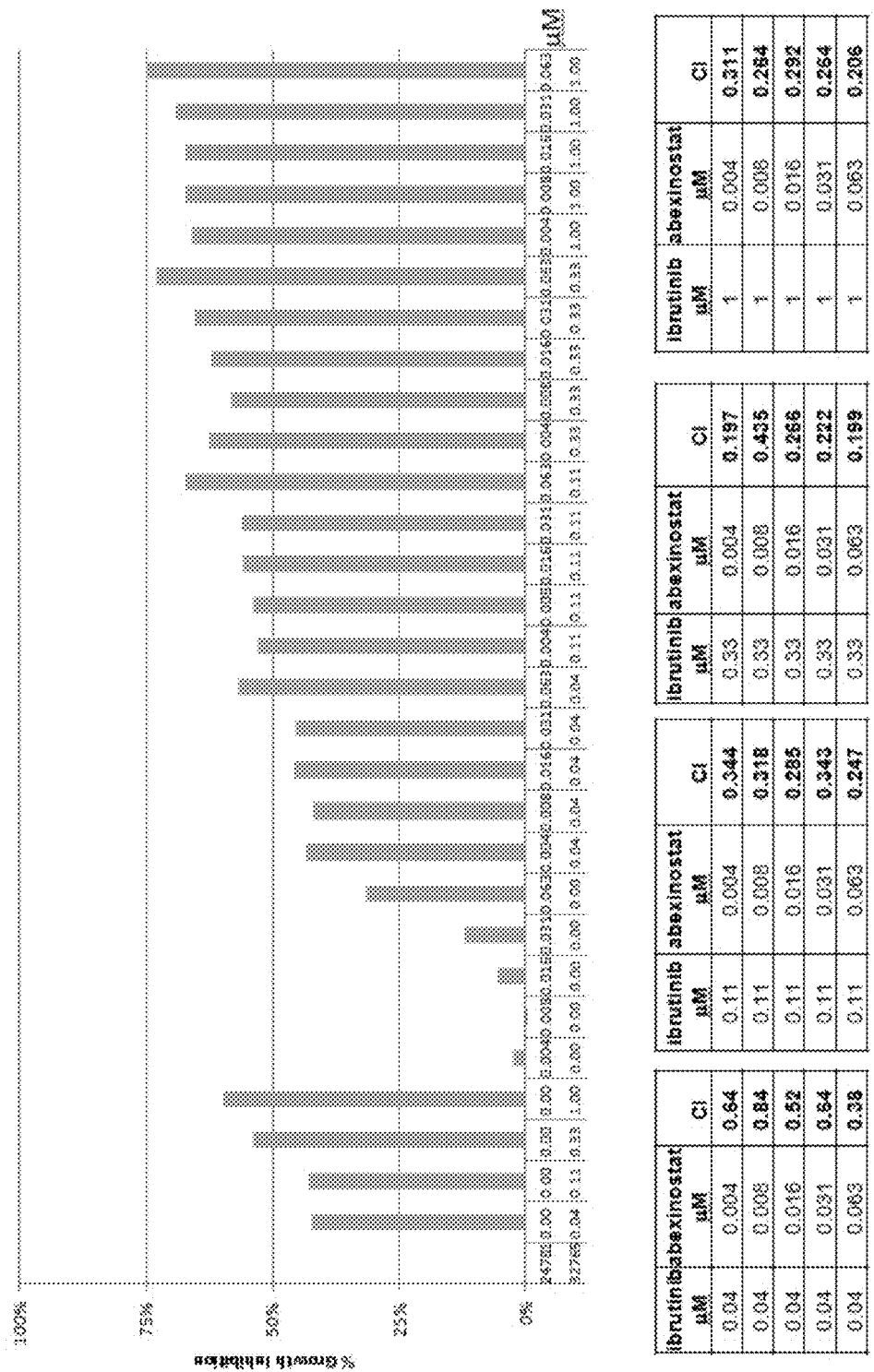
FIG. 12: Is an illustrative example of the effects of the combination of abexinostat and ibrutinib in MDA-MB-453 cells (breast carcinoma). 24781 is abexinostat and 32765 is ibrutinib. CI value<1 indicates synergy, CI value=1 indicates additive, and CI value>1 indicate antagonist.
Figure 13:
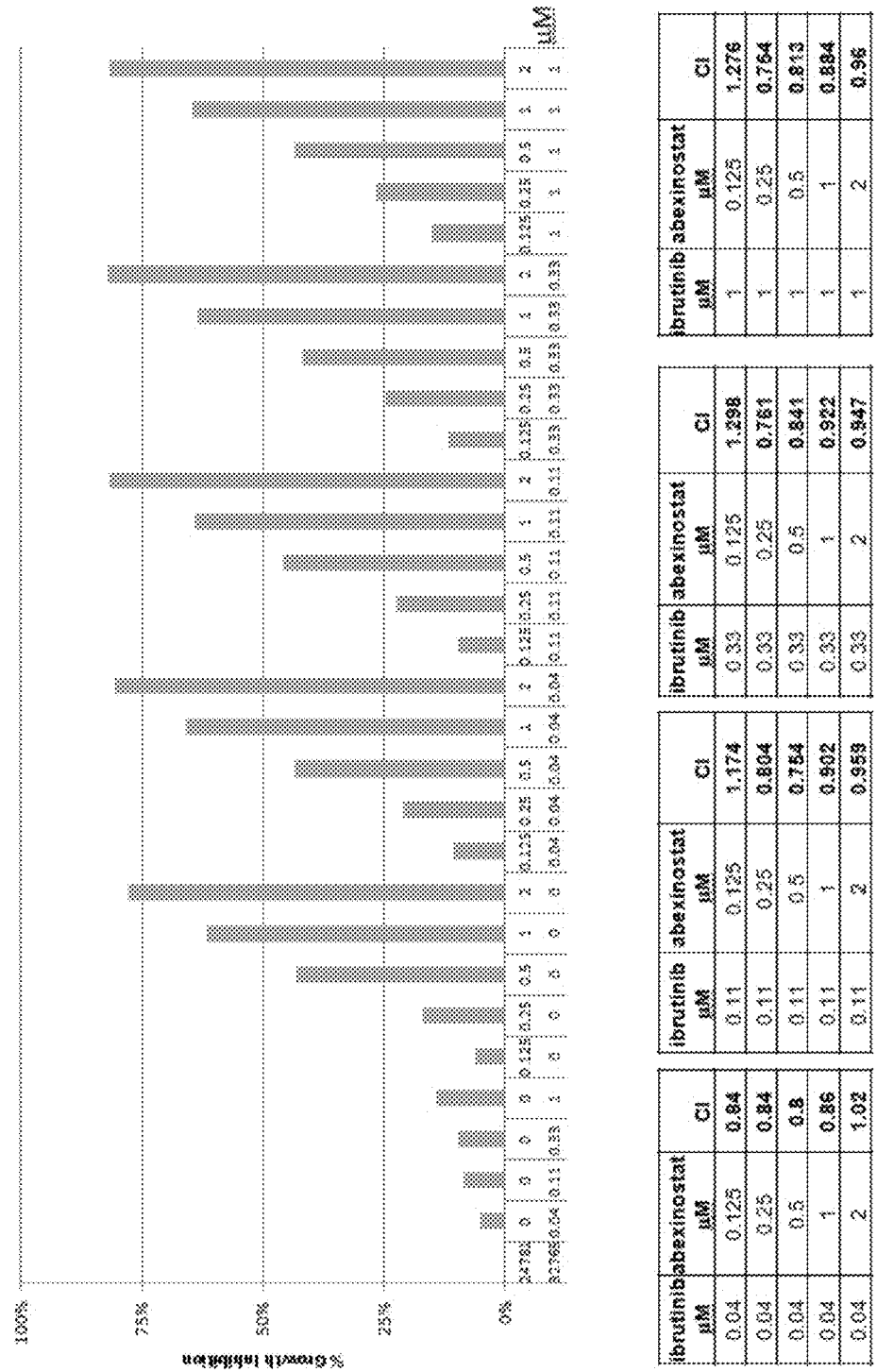
FIG. 13: Is an illustrative example of the effects of the combination of abexinostat and ibrutinib in DLD-1 cells (colorectal adenocarcinoma). 24781 is abexinostat and 32765 is ibrutinib. CI value<1 indicates synergy, CI value=1 indicates additive, and CI value>1 indicate antagonist.
Figure 14:
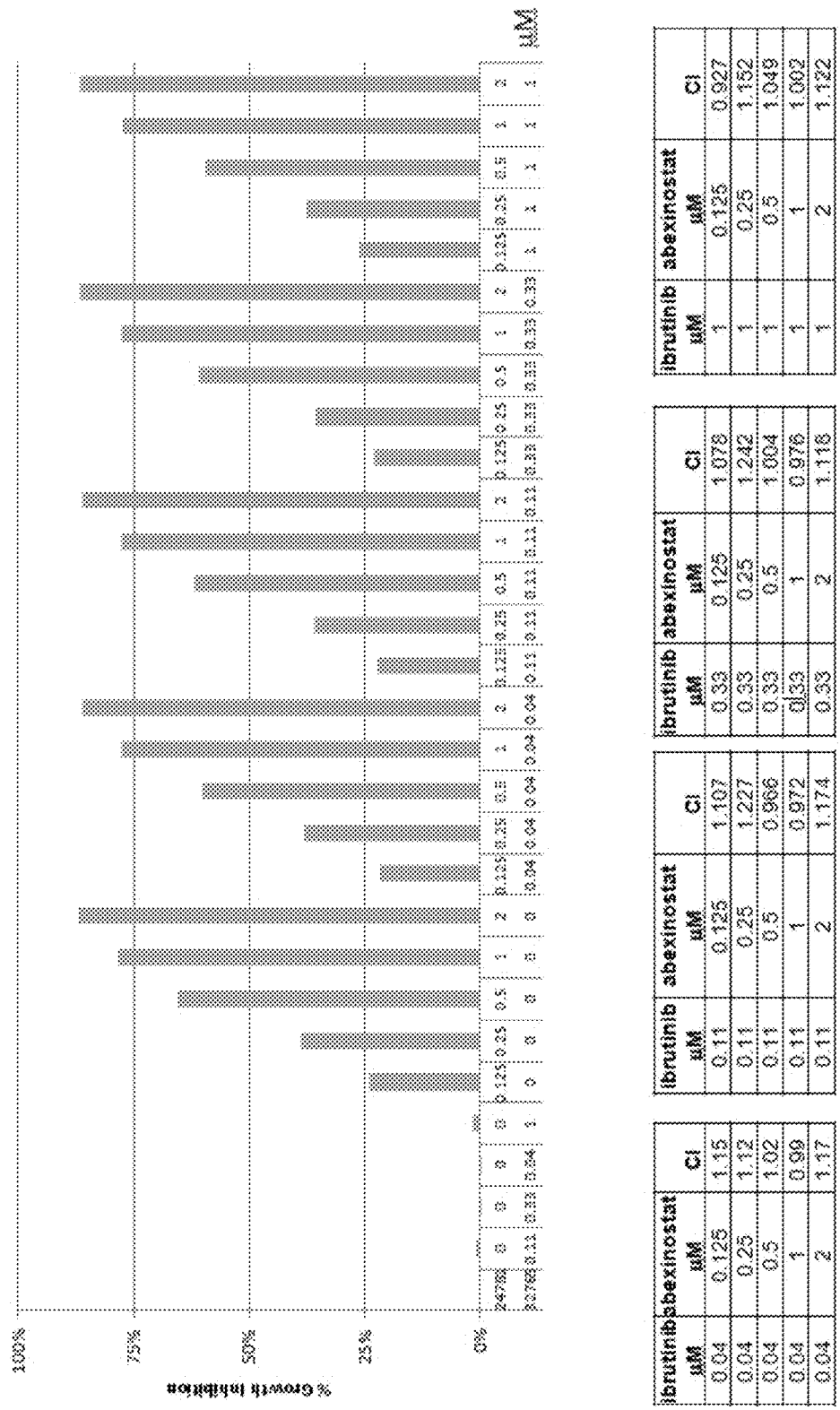
FIG. 14: Is an illustrative example of the effects of the combination of abexinostat and ibrutinib in NCI-H460 cells (large cell lung cancer). 24781 is abexinostat and 32765 is ibrutinib. CI value<1 indicates synergy, CI value=1 indicates additive, and CI value>1 indicate antagonist.
Figure 15:
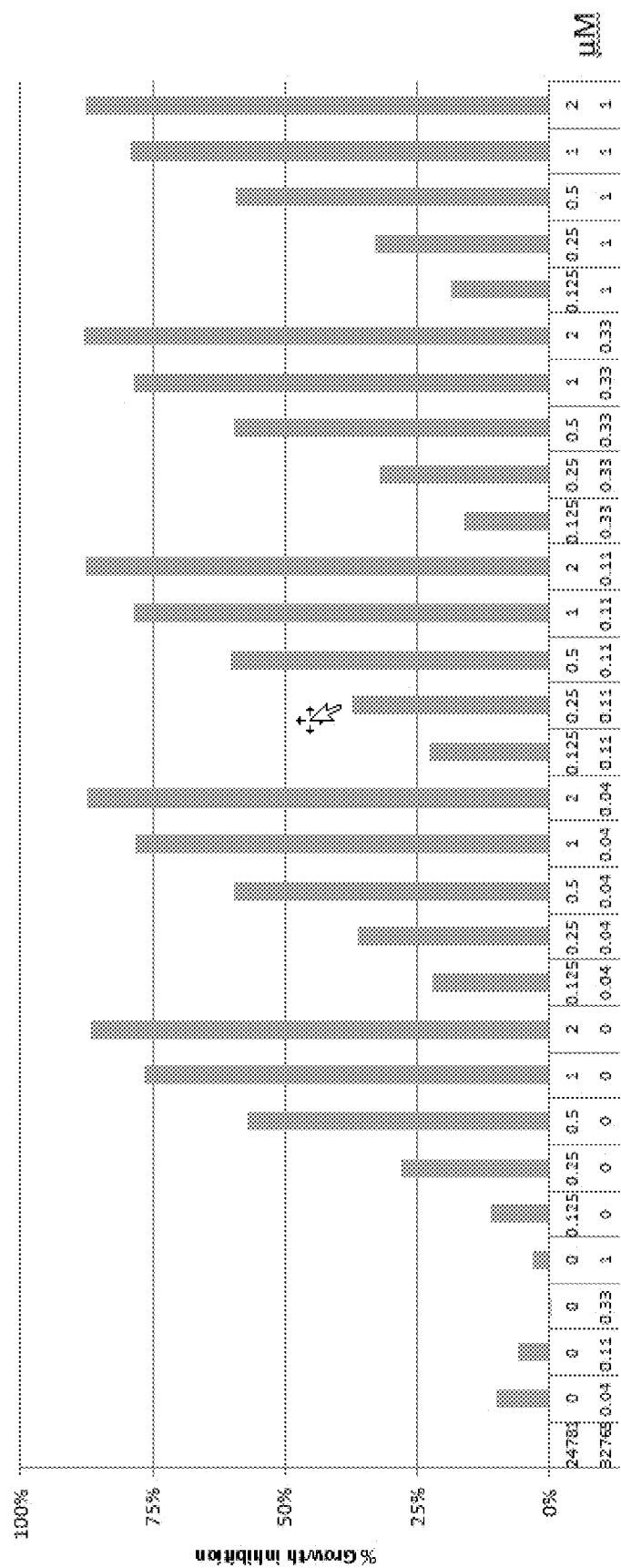
FIG. 15: Is an illustrative example of the effects of the combination of abexinostat and ibrutinib in A549 cells (lung carcinoma). 24781 is abexinostat and 32765 is ibrutinib.
Figure 16:
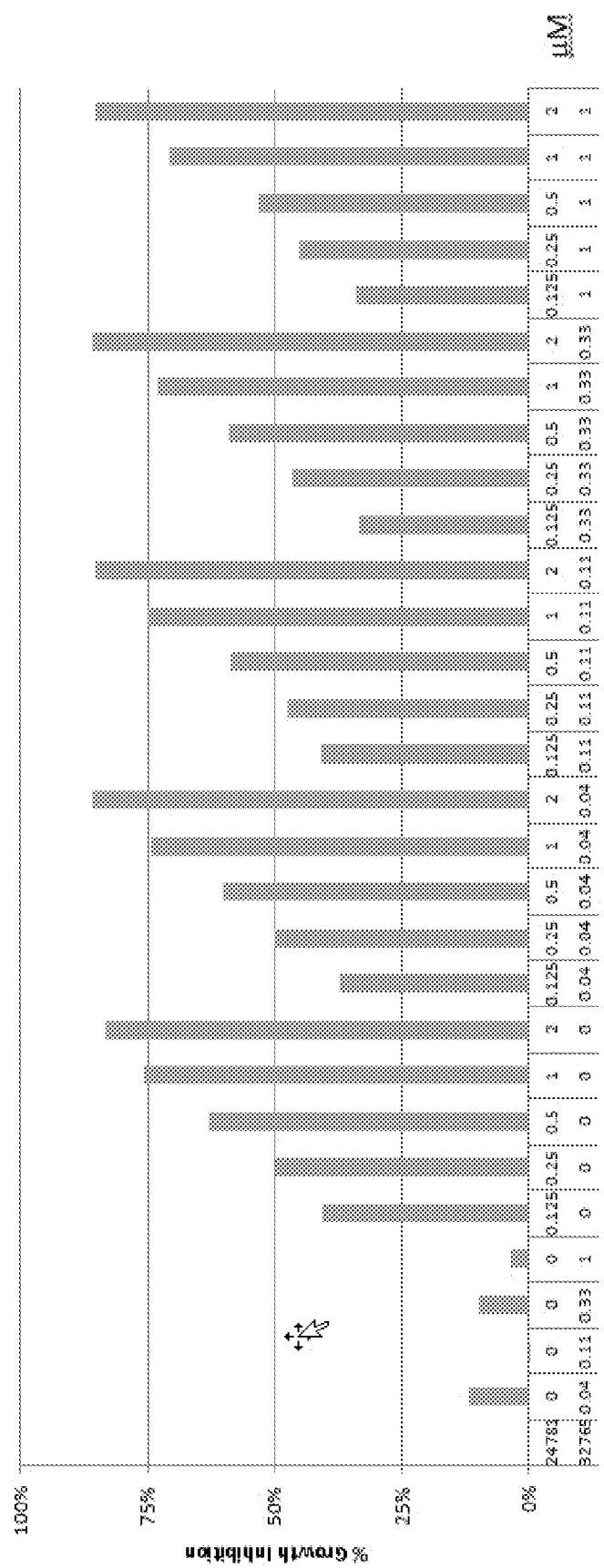
FIG. 16: Is an illustrative example of the effects of the combination of abexinostat and ibrutinib in LNCaP cells (prostate carcinoma). 24781 is abexinostat and 32765 is ibrutinib.

Images of the whole left lung lobe from control and treated mice are shown in FIG. 7 and the tissue sections showing the tumor histology are shown in FIG. 8.

Conclusion

The data analysis reveals that both Abexinostat and Ibrutinib greatly reduce tumor number in mice treated from 2 to 3 months and the drugs appear to act synergistically. The reduction was 50-60% for each drug alone and 75% when the drugs were used together. Although the drugs reduce tumor number, the tumors appear morphologically similar between treated and control samples at 3 months.

At 6 months, the tumor number is variable, but in treated mice the number of large tumors (over 1 mm) is much lower. The drugs also appear to act synergistically at this stage to reduce the number of large tumors. The tumors for control and treated mice have lymphocyte infiltration. However tumors in mice receiving Abexinostat have a high number of apoptotic cells. Tumors in mice receiving Ibrutinib lack the high number of apoptotic macrophages seen in the control and Abexinostat-treated mice, and have less tumor necrosis than the control samples.

Example 2

Clinical Trial for Pancreatic Cancer

Study Type: Interventional
Study Design: Allocation: Non-Randomized
Endpoint Classification: Safety/Efficacy Study
Intervention Model: Single Group Assignment
Masking: Open Label
Primary Purpose: Treatment
Primary Outcome Measures: To assess the response rate associated with ibrutinib and abexinostat in patients with advanced pancreatic cancer
Secondary Outcome Measures: To assess the side effects of ibrutinib and abexinostat in patients with advanced pancreatic cancer
Detailed Description
Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.
Eligibility
  Ages Eligible for Study: 18 Years and older
  Genders Eligible for Study: Both
  Accepts Healthy Volunteers: No
  Inclusion Criteria:
  Metastatic pancreatic carcinoma (excluding pancreatic endocrine tumors)
  Only patients with measurable disease
  ECOG performance status<or equal to 1
  Life expectancy>12 weeks
  Signed informed consent
  Failed or intolerance to first-line therapy for metastatic disease with a gemcitabine-containing regimen. Patients may have received adjuvant therapy in addition to one prior regimen for metastatic disease.
  >4 weeks must have elapsed from the completion of previous chemotherapy and patients must have recovered from any related toxicities
  >4 weeks must have elapsed from the participation in any investigational drug study
  Laboratory values: ANC>1500/mm3; Hemoglobin>9.0 gm/dl; Platelets>100,000/mm3; SGOT<2.5× upper limit of normal; or <5× upper limit of normal if evidence of liver metastases; Alkaline phosphatase<2.5× upper limit of normal; or <5× upper limit of normal if evidence of liver metastases; Total bilirubin<1.5× upper limit of normal; Creatinine clearance>50 cc/min (by Cockroft-Gault or as determined from a 24-hour urine collection).
  Exclusion Criteria:
  More than one prior chemotherapy treatment regimen for metastatic disease
  Clinically apparent central nervous system (CNS) metastases or carcinomatous meningitis
  Clinically significant cardiac disease (e.g. congestive heart failure, symptomatic coronary artery disease and cardiac arrhythmias not well controlled with medication or heart attack within the last 12 months).
  Major surgery within 4 weeks of the start of study treatment, without complete recovery.
  Evidence of CNS metastases (unless CNS metastases have been stable for >3 months) or history of uncontrolled seizures, central nervous system disorders
  Uncontrolled serious medical or psychiatric illness
  Women must not be pregnant or lactating
  Concurrent radiation therapy
  Other active malignancy
  Inability to swallow capsules
  Patients lacking physical integrity of the upper gastrointestinal tract or who have malabsorption syndrome Example 3

Colon Cancer

Study Type: Interventional
Study Design: Allocation: Randomized
Endpoint Classification: Efficacy Study
Intervention Model: Parallel Assignment
Masking: Double Blind (Subject, Investigator)
Primary Outcome Measures: Disease-free Survival following therapy with ibrutinib and abexinostat
Secondary Outcome Measures: Survival as Assessed by Death From Any Cause
Detailed Description
Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.
Eligibility
  Ages Eligible for Study: 18 Years and older
  Genders Eligible for Study: Both
  Accepts Healthy Volunteers: No
  Inclusion Criteria:
  Patients must consent to be in the study and must have signed and dated an IRB approved consent form conforming to federal and institutional guidelines
  Randomization must occur during the three-week interval beginning on postoperative day 29 and ending on postoperative day 50
  The distal extent of the tumor must be >=12 cm from the anal verge on endoscopy; if the patient is not a candidate for endoscopy, then the distal extent of the tumor must be >=12 cm from the anal verge as determined by surgical examination
  The patient must have had an en bloc complete gross resection of tumor (curative resection) by open laparotomy or laparoscopically-assisted colectomy; patients who have had a two-stage surgical procedure, to first provide a decompressive colostomy and then in a later procedure to have the definitive surgical resection, are eligible Patients must have histologically confirmed adenocarcinoma of the colon that meets one of the following criteria: Stage II carcinoma (T3,4 N0 M0); the tumor invades through the muscularis propria into the subserosa or into non-peritonealized pericolic or perirectal tissues (T3); or directly invades other organs or structures, and/or perforates visceral peritoneum (T4); Stage III carcinoma (any T N1,2 M0); the tumor has invaded to any depth, with involvement of regional lymph nodes Patients with T4 tumors that have involved an adjacent structure (e.g., bladder, small intestine, ovary, etc.) by direct extension from the primary tumor are eligible if all of the following conditions are met: All or a portion of the adjacent structure was removed en bloc with the primary tumor; In the opinion of the surgeon, all grossly visible tumor was completely resected ("curative resection"); Histologic evaluation by the pathologist confirms the margins of the resected specimen are not involved by malignant cells; and Local radiation therapy will not be utilized Patients with more than one synchronous primary colon tumor are eligible; (staging classification will be based on the more advanced primary tumor)

Patients must have an ECOG performance status of 0 or 1

At the time of randomization, postoperative absolute granulocyte count (AGC) must be >=1500/mm^3 (or <1500/mm^3, if in the opinion of the investigator, this represents an ethnic or racial variation of normal)

At the time of randomization, the postoperative platelet count must be >=100,000/mm^3

Bilirubin must be =<ULN for the lab unless the patient has a chronic grade 1 bilirubin elevation due to Gilbert's disease or similar syndrome due to slow conjugation of bilirubin Alkaline phosphatase must be <2.5×ULN for the lab AST must be <1.5×ULN for the lab. If AST is >ULN, serologic testing for hepatitis B and C must be performed and results must be negative Serum creatinine=<1.5×ULN for the lab Urine protein/creatinine (UPC) ratio of <1.0; patients with a UPC ratio>=1.0 must undergo a 24-hour urine collection, which must be an adequate collection and must demonstrate <1 gm of protein in the 24-hour urine collection in order to participate in the study Patients with prior malignancies, including colorectal cancers, are eligible if they have been disease-free for >=5 years and are deemed by their physician to be at low risk for recurrence; patients with squamous or basal cell carcinoma of the skin, melanoma in situ, carcinoma in situ of the cervix, or carcinoma in situ of the colon or rectum that have been effectively treated are eligible, even if these conditions were diagnosed within 5 years prior to randomization Exclusion Criteria:

Patients<18 years old

Colon tumor other than adenocarcinoma

Rectal tumors, i.e. a tumor located <12 cm from the anal verge on endoscopy, or by surgical exam if the patient is not a candidate for endoscopy Isolated, distant, or non-contiguous intra-abdominal metastases, even if resected Any systemic or radiation therapy initiated for this malignancy Any significant bleeding that is not related to the primary colon tumor within 6 months before study entry Serious or non-healing wound, skin ulcers, or bone fracture Gastroduodenal ulcer(s) determined by endoscopy to be active Invasive procedures defined as follows: Major surgical procedure, open biopsy, or significant traumatic injury within 28 days prior to randomization; Anticipation of need for major surgical procedures during the course of the study; Core biopsy or other minor procedure, excluding placement of a vascular access device, within 7 days prior to randomization Uncontrolled blood pressure defined as >150/90 mmHg History of TIA or CVA History of arterial thrombotic event within 12 months before study entry Symptomatic Peripheral Vascular Disease PT/INR>1.5, unless the patient is on therapeutic doses of warfarin. If so, the following criteria must be met for enrollment: The subject must have an in-range INR (usually between 2 and 3) on a stable dose of warfarin; The subject must not have active bleeding or a pathological condition that is associated with a high-risk of bleeding Concomitant halogenated antiviral agents Clinically significant peripheral neuropathy at the time of randomization (defined in the NCI Common Terminology Criteria for Adverse Events Version 3.0 [CTCAE v3.0] as grade 2 or greater neurosensory or neuromotor toxicity)

Non-malignant systemic disease (cardiovascular, renal, hepatic, etc.) that would preclude any of the study therapy drugs; specifically excluded are the following cardiac conditions: New York Heart Association Class III or IV cardiac disease; History of myocardial infarction within 12 months before study entry; Unstable angina within 12 months before study entry; and Symptomatic arrhythmia History of chronic or persistent viral hepatitis or other chronic liver disease Psychiatric or addictive disorders or other conditions that, in the opinion of the investigator, would preclude the patient from meeting the study requirements Example 4

Breast and Ovarian Cancer

Study Type: Interventional
Study Design: Allocation: Non-Randomized
Endpoint Classification: Safety Study
Intervention Model: Single Group Assignment
Masking: Open Label
Primary Purpose: Treatment
Primary Outcome Measures: Determine the safety and toxicity of the combination of ibrutinib and abexinostat in BRCA 1/2-associated recurrent breast and ovarian cancer patients
Secondary Outcome Measures: Assess clinical activity of the combination;
Detailed Description Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.

Eligibility
    Ages Eligible for Study: 18 Years and older
    Genders Eligible for Study: Both
    Accepts Healthy Volunteers: No
    Inclusion Criteria
    Patients must have breast and/or epithelial ovarian cancer, primary peritoneal cancer, and/or fallopian tube cancer histologically or cytologically confirmed at the NCI that is metastatic or unresectable and for which standard curative measures do not exist or are no longer effective.
    All patients in cohort 1 must have measurable and/or evaluable disease.
    Patients in the expansion cohort 2 must have safely biopsible disease as determine by an interventional radiologist and must agree to the first mandatory biopsy (the other two biopsies optional).
    Breast cancer patients with locally advanced, unresectable disease must have been previously treated with standard therapy.
        There is no limit on number of prior therapy.
        ECOG performance status less than or equal to 2 (Karnofsky greater than or equal to 60%).
        Life expectancy greater than 3 months.
        Patients must have normal organ and marrow function defined as follows: hemoglobin greater than or equal to 10 g/dL; leukocytes greater than or equal to 3,000/mcL; absolute neutrophil count greater than or equal to 1,500/mcL; platelets greater than or equal to 100,000/mcL; total bilirubin less than or equal to upper limit of normal (ULN) in the absence of Gilbert's syndrome; AST(SGOT)/ALT(SGPT) less than or equal to 2.5×ULN; creatinine clearance greater than or equal to 60 mL/min by 24-hour urine; corrected or Ionized Calcium less than or equal to ULN; potassium within normal limits
        A documented deleterious BRCA 1/2 germline mutation or BRCAPRO score of greater than or equal to 30% for patients enrolling in Group A.
        For patients enrolling in the sporadic serous epithelial ovarian cancer group, Group B, a negative family history (BRCAPRO score less than or equal to 20% or negative BRCA1/2 mutation test).
        For patients enrolling in the triple negative breast cancer (ER-/PR-/Her2-) group, Group B, a negative family history and/or BRCAPRO score less than or equal to 10% or negative BRCA1/2 mutation test).
    Exclusion Criteria
    Patients who have had chemotherapy, biological therapy, hormonal therapy (with the exception of raloxifene or others approved for bone health) or radiotherapy within 4 weeks (6 weeks for nitrosoureas or mitomycin C) prior to entering the study.
    Patients may not be receiving any other investigational agents or had them in the previous 28 days.
    Patients with known brain metastases diagnosed within 1 year should be excluded from this clinical trail because of their poor prognosis and because they often develop progressive neurological dysfunction that would confound the evaluation of neurologic and other adverse events.
        Clinically significant bleeding.
        Inability to swallow capsules.
        Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.
        Pregnant and breast-feeding women.
        HIV-positive patients on combination antiretroviral therapy are ineligible because of the potential for pharmacokinetic interactions with AZD2281. In addition, these patients are at increased risk of lethal infections when treated with marrow-suppressive therapy such as carboplatin.
        Major surgery within the past 28 days.
        Patients with locally advanced breast tumors presenting for their initial therapy, or patients with local (only in breast or chest wall) recurrence only will not be eligible for this trial
        For subjects in the dose-expansion cohorts, history of prior invasive malignancies within the past 5 years (with the exception of non-melanomatous skin cancers, non-invasive bladder cancer, stage I endometrial cancer or cervical cancer cured by surgical resection).

Example 5

Bladder Cancer

Study Type: Interventional
    Study Design: Allocation: Randomized
    Primary Purpose: Treatment with combination of ibrutinib and abexinostat
    Objectives
    I. Determine whether treatment with ibrutinib and abexinostat is effective in preventing recurrence of tumor after transurethral resection in patients with low grade, superficial transitional cell carcinoma of the bladder.
    II. Determine the incidence and severity of toxicities associated with the long-term use of this drug in this patient population.
Eligibility
    Ages Eligible for Study: 18 Years and older
    Genders Eligible for Study: Both
    Accepts Healthy Volunteers: No
Criteria
    Disease Characteristics
    Histologically confirmed low grade (grade 1 or 2), superficial (stage Ta or T1) transitional cell carcinoma (TCC) of the bladder
    Newly diagnosed or recurrent
    All visible tumor must have been resected within the past 12 weeks
    Standard clinical management determined to be expectant observation without further surgery, intravesical therapy, or systemic therapy
    No prior upper tract TCC
    No history of grade 3 TCC, carcinoma in situ including severe dysplasia, non-TCC histology, or TCC greater than or equal to T2
    No involvement of upper urinary tract prior to or at the time of initial tumor resection
    Abdominal CT scan, IVP, or retrograde pyelogram within the past 3 months to rule out upper urinary tract tumor
    Patient Characteristics
    Not pregnant or nursing
    Negative pregnancy test
    Fertile patients must use effective contraception
    No prior malignancy within the past 5 years and no concurrent malignancy except nonmelanomatous skin cancer or carcinoma in situ of the cervix
    No clinically significant hearing loss (i.e., hearing loss effects everyday life and/or wears a hearing aide)
        No other significant medical or psychiatric condition

Example 6

Lung Cancer

Study Type: Interventional
Study Design: Allocation: Randomized
Endpoint Classification: Safety/Efficacy Study
Masking: Double Blind (Subject, Investigator)
Primary Purpose: Treatment with ibrutinib and abexinostat
Primary Outcome Measures: Immune-related Progression-free Survival (irPFS) in Participants With Nonsmall-cell Lung Cancer (NSCLC) Per Immune-related Response Criteria (irRC) [Time Frame: Tumor assessed at screening, every 6 weeks on treatment to Week 24, and every 12 weeks on maintenance until immune-related Progressive Disease (irPD) or death (of censored, maximum reached: 16.5 months)]

irPFS is defined as the time between the randomization date and date of immune-related Progressive Disease (irPD) (at least 25% increase percentage change in total tumor burden, including new lesions) or death, whichever occurs first. For patients with no recorded postbaseline tumor assessments, irPFS is censored at randomization. Participant who die without reported irPD are considered to have progressed on the date of death. For those who remain alive and have no irPD, irPFS is censored on the date of last evaluable tumor assessment. Independent review committee performed tumor assessment Detailed Description Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.

Inclusion Criteria

Histologically or cytologically confirmed lung cancer (Stage IIIb/IV nonsmall-cell lung cancer or extensive stage small-cell lung cancer [SCLC])

Measurable tumor lesion (as long as it is not located in a previously irradiated area) as defined by modified World Health Organization criteria Eastern Cooperative Oncology Group performance status of <1 at study entry Accessible for treatment and follow-up Exclusion Criteria:

Brain metastases

Malignant pleural effusion

Autoimmune disease

Motor neuropathy of autoimmune origin

SCLC-related paraneoplastic syndromes

Any concurrent malignancy other than nonmelanoma skin cancer; carcinoma in situ of the cervix or breast; or prostate cancer treated with systemic therapy (participants with a previous malignancy but without evidence of disease for 5 years were allowed to enter the study)

Prior systemic therapy for lung cancer. Prior radiation therapy or locoregional surgeries performed later than at least 3 weeks prior to randomization date were allowed.

Known HIV or hepatitis B or C infection

Chronic use of immunosuppressants and/or systemic corticosteroids (used in the management of cancer or noncancer-related illnesses). However, use of corticosteroids was allowed if used as premedication for paclitaxel infusion or for treating immune-related adverse events or adrenal insufficiencies.

Inadequate hematologic function defined by an absolute neutrophil count<1,500/mm^3, a platelet count<100,000/mm^3, or hemoglobin level<9 g/dL.

Inadequate hepatic function defined by a total bilirubin level>2.0 times the upper limit of normal (ULN), or ≥2.5 times the ULN if liver metastases are present, aspartate aminotransferase and alanine aminotransferase levels≥2.5 times the ULN or ≥5 times the ULN if liver metastases are present.

Inadequate renal function defined by a serum creatinine level≥2.5 times the ULN

Inadequate creatinine clearance defined as less than 50 mL/min.

Example 7

Prostate Cancer

Study Type: Interventional
Study Design: Endpoint Classification: Safety/Efficacy Study
Intervention Model: Single Group Assignment
Masking: Open Label
Primary Purpose: Treatment
Primary Outcome Measures: PSA response rate with abexinostat and ibrutinib therapy in androgen independent non-metastatic prostate cancer [Time Frame: An average every 6 weeks for up to 3 months]
Secondary Outcome Measures: Overall survival of androgen independent non-metastatic prostate cancer patients treated with abexinostata nd ibrutinib [Time Frame: Every 3 months]

Detailed Description

Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.

Eligibility

Ages Eligible for Study: 18 Years and older

Genders Eligible for Study: Both

Accepts Healthy Volunteers: No

Inclusion Criteria:

A histologic diagnosis of prostate adenocarcinoma.

No evidence of bone/visceral metastases as visualized on standard imaging such as bone scan, chest X-ray, CT scan or MRI of abdomen and pelvis.

PSA-only progression despite androgen deprivation therapy. PSA progression is defined as 3 rising levels, with a minimum interval of 2 weeks between each determination. The last determination must have a minimum value of 1 ng/ml and be determined within two weeks prior to registration. If the second or third confirmatory value is less than the previous value, the patient will still be eligible if a repeat value (No. 4) is found to be greater than all the prior values.

If patient has been on antiandrogen in the past 28 days, then PSA progression after withdrawal period (28 days for flutamide and 42 days for bicalutamide or nilutamide) is required.

ECOG performance status of 0-1.

No investigational or commercial agents or therapies (except LHRH agonists) may be administered concurrently with the intent to treat the patient's malignancy. Patients on LHRH agonists must continue the use of LHRH agonist therapy. Bisphosphonates can be administered per treating physician discretion.

At least 4 weeks must have elapsed since prior systemic therapy, except for LHRH analogue therapy and steroids. If steroids are being used for therapy of prostate cancer, these should be discontinued prior to starting avastin therapy.

Life expectancy of at least 6 months.

Ability to understand and the willingness to sign a written informed consent that is approved by the Institutional Human Investigation Committee.

Use of effective means of contraception in subjects.

Exclusion Criteria:

Inability to comply with study and/or follow-up procedures.

Inadequately controlled hypertension (defined as systolic blood pressure>150 and/or diastolic blood pressure>100 mmHg on antihypertensive medications).

Any prior history of hypertensive crisis or hypertensive encephalopathy.

New York Heart Association (NYHA) Grade II or greater congestive heart failure

History of myocardial infarction or unstable angina within last 12 months prior to study enrollment.

History of stroke or transient ischemic attack within 6 months prior to study enrollment.

Known CNS disease.

Significant vascular disease (e.g., aortic aneurysm, aortic dissection).

Symptomatic peripheral vascular disease.

Evidence of bleeding diathesis or coagulopathy.

Patients on anticoagulants are allowed if patient has been on therapy for at least 4 weeks and patient has no acute thromboembolic activity.

Major surgical procedure, open biopsy, or significant traumatic injury within. 28 days prior to study enrollment or anticipation of need for major surgical procedure during the course of the study.

Core biopsy or other minor surgical procedure, excluding placement of a vascular access device, within 7 days prior to study enrollment.

History of abdominal fistula, gastrointestinal perforation, or intra-abdominal abscess within 6 months prior to study enrollment.

Serious, non-healing wound, ulcer, or bone fracture.

Proteinuria at screening as demonstrated by: Urine protein:creatinine (UPC) ratio≥1.0 at screening Refusal to use effective means of contraception.

Patients with known brain metastases should be excluded from this clinical trial because of their poor prognosis and because they often develop progressive neurologic dysfunction that would confound the evaluation of neurologic and other adverse events.

History of allergic reactions attributed to compounds of similar chemical or biologic composition to avastin.

Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.

Patients with immune deficiency such as HIV-positive patients or those receiving combination anti-retroviral therapy are excluded from the study because of lack of safety data for avastin in these patients.

Example 8

Bile Duct Cancer

Study Type: Interventional

Study Design: Endpoint Classification: Safety/Efficacy Study

Intervention Model: Single Group Assignment

Masking: Open Label

Primary Purpose: Treatment

Primary Outcome Measures: Overall survival with abexinostat and ibrutinib therapy [Time Frame: 3 years]

Secondary Outcome Measures: Response rate defined as proportion of patients with complete response (CR), partial response (PR), stable disease (SD), or progressive disease (PD), using based on the RECIST version 1.1

Detailed Description

Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.

Eligibility

Ages Eligible for Study: 18 Years and older

Genders Eligible for Study: Both

Accepts Healthy Volunteers: No

Inclusion Criteria:

Histologically and cytologically proven cholangiocarcinoma of any type (including intrahepatic cholangiocarcinoma, extrahepatic primary cholangiocarcinoma, hilar cholangiocarcinomas, cholangiocarcinomas located in the gall bladder or hepatic capsule effraction, and carcinoma of the Ampulla of Vater, etc.) that is not amenable to surgery, radiation, or combined modality therapy with curative intent, and has failed or is not eligible for available chemotherapies such as gemcitabine with or without platinum Local, locally-advanced, or metastatic disease documented as having shown progression on a scan (e.g., computed tomography [CT], magnetic resonance imaging [MRI])

Measurable tumor according to Response Evaluation Criteria in Solid Tumors (RECIST) 1.1 criteria with at least one unidimensionally measurable target lesion No evidence of biliary duct obstruction, unless obstruction is controlled by local treatment or, in whom the biliary tree can be decompressed by endoscopic or percutaneous stenting with subsequent reduction in bilirubin to below 1.5× upper level of normal (ULN)

Eastern Cooperative Oncology Group (ECOG) performance status being 0-3

Expected survival>3 months

Women of child-bearing potential (i.e., women who are pre-menopausal or not surgically sterile) must use accepted contraceptive methods (abstinence, intrauterine device [IUD], oral contraceptive or double barrier device) during the study, and must have a negative serum or urine pregnancy test within 1 week prior to treatment initiation Fertile men must practice effective contraceptive methods during the study, unless documentation of infertility exists Granulocyte count>=1500/mm^3

White blood cell (WBC)>=3500 cells/mm^3 or >=3.5 bil/L

Platelet count>=150,000 cells/mm^3 or >=150 bil/L

Absolute neutrophil count (ANC)>=1500 cells/mm^3 or >=1.5 bil/L

Hemoglobin>=9 g/dL or >=90 g/L

Aspartate aminotransferase (AST/serum glutamic oxaloacetic transaminase [SGOT])=<3× upper normal limit (UNL), alanine aminotransferase (ALT/serum glutamate pyruvate transaminase [SGPT])=<3×UNL (=<5×UNL if liver metastases present)

Bilirubin=<1.5×UNL

Serum creatinine=<2.0 mg/dL or 177 µmol/L

International normalized ratio or INR must be =<1.5

No evidence of active infection and no serious infection within the past month

Mentally competent, ability to understand and willingness to sign the informed consent form Exclusion Criteria:

Patients receiving any other standard or investigational treatment for their cancer Serious medical illness that would potentially increase patients' risk for toxicity Any active uncontrolled bleeding, and any patients with a bleeding diathesis (e.g., active peptic ulcer disease)

Pregnant women, or women of child-bearing potential not using reliable means of contraception Lactating females Fertile men unwilling to practice contraceptive methods during the study period Life expectancy less than 3 months Unwilling or unable to follow protocol requirements Dyspnea with moderate exertion; patients with pleural or pericardial effusions Active heart disease including but not limited to symptomatic congestive heart failure, symptomatic coronary artery disease, symptomatic angina pectoris, symptomatic myocardial infarction, arrhythmias requiring medication, or symptomatic congestive heart failure; also patients with a history of myocardial infarction that is <1 year prior to registration, or patients with previous congestive heart failure (<1 year prior to registration) requiring pharmacologic support or with left ventricular ejection fraction<50%)

A marked baseline prolongation of QT/corrected QT (QTc) interval (e.g., repeated exhibition of a QTc interval>470 ms)

A history of additional risk factors for torsade de pointes (e.g., heart failure, hypokalemia, family history of long QT syndrome)

Evidence of active infection, or serious infection within the past month

Patients with known human immunodeficiency virus (HIV) infection

Requirement for immediate palliative treatment of any kind including surgery

Patients that have received a chemotherapy regimen with stem cell support in the previous 6 months Prior illicit drug addiction Any condition or abnormality which may, in the opinion of the investigator, compromise the safety of the patient Example 9

Large Cell Lung Cancer

Study Type: Interventional

Study Design: Endpoint Classification: Safety/Efficacy Study

Intervention Model: Single Group Assignment

Masking: Open Label

Primary Purpose: Treatment

Primary Outcome Measures: The proportion of subjects progression-free at Month 3. Time Frame [Time Frame: 3 months]

Secondary Outcome Measures: the proportion of subjects progression-free at Month 6 [Time Frame: 6 months]; overall response rate (ORR) is the proportion of patients with a best overall response of Complete Response (CR) or Partial Response (PR) at Month 3 [Time Frame: 3 months]; disease control rate (DCR) is the proportion of patients with a best overall response of CR or PR or Stable Disease (SD) at Month 3 (C4D21) [Time Frame: 3 months]; progression Free Survival [Time Frame: approximately 3-6 months]; overall Survival [Time Frame: estimated 12 months]

Detailed Description

Patients will be treated three times daily ibrutinib (140 mg/dose) and once daily with abexinostat for 4 consecutive days, followed by 3 days off of abexinostat (a cycle is 7 days). At day 1 of each cycle a physical exam and blood work will be performed. Reassessment of tumor size will be conducted at 6 weeks, 12 weeks and then every 9 weeks thereafter. Patients will remain on treatment until one of the following occur: disease progression, illness that prevents further treatment or unacceptable adverse events.

Eligibility

Ages Eligible for Study: 18 Years and older

Genders Eligible for Study: Both

Accepts Healthy Volunteers: No

Inclusion Criteria:

Written informed consent obtained according to local guidelines

Histologically confirmed diagnosis of stage IV lung cancer of LC-NEC type according to WHO classification:

Histolocial analysis of newly diagnosed disease must not be older than 8 weeks from signed consent Relapse must be confirmed by histology Neuroendocrine differentiation 3. World Health organisation (WHO) performance status grade≤1

4. measurable disease

5. Adequate bone marrow function

6. Adequate liver function

7. Adequate renal function

Exclusion Criteria:

Clinical evidence of central nervous system (CNS) metastases.

Presence of SCLC cells

Patients who have a history of another primary malignancy≤3 years, with the exception of inactive basal or squamous cell carcinoma of the skin or cervical cancer in situ, early stages of breast cancer (LCIS and DCIS) and prostate cancer (stage T1a)

Prior chemotherapy for the treatment of advanced lung cancer and/or not having recovered from the side effects of any other therapy (adjuvant treatment for earlier stages I-III is allowed if finished at least one year before study entry)

Treatment with any investigational drug≤28 days before starting study treatment or who have not recovered from side effects of such therapy Women who are pregnant or lactating.

What is claimed is:

1. A method for treating a solid tumor comprising administering to an individual in need thereof, (R)-1-(3-(4-amino-3-(4-phenoxyphenyl)-1H-pyrazolo[3,4-d]pyrimidin-1-yl)piperidin-1-yl)prop-2-en-1-one

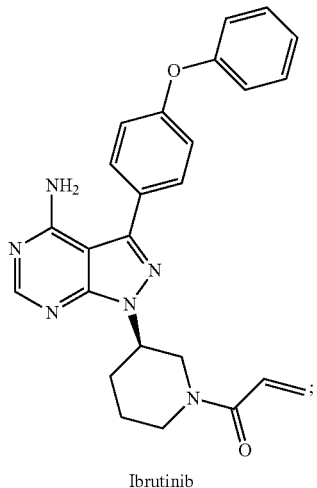 [SMILES: C=CC(=O)N1CCC[C@@H](n2nc(-c3ccc(Oc4ccccc4)cc3)c3c(N)ncnc32)C1]

Ibrutinib and 3-[(dimethylamino)methyl]-N-{2-[4-(hydroxycarbamoyl)phenoxy]ethyl}-1-benzofuran-2-carboxamide

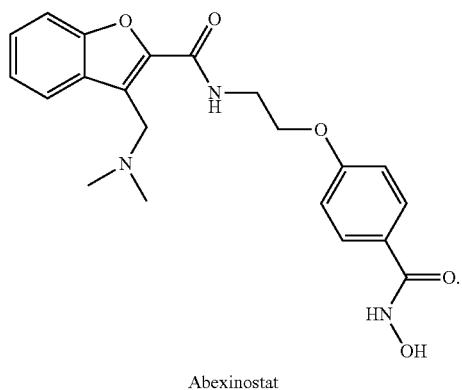 [SMILES: CN(C)Cc1c(C(=O)NCCOc2ccc(C(=O)NO)cc2)oc2ccccc12]

Abexinostat

2. The method of claim 1, wherein the solid tumor is a carcinoma.
3. The method of claim 2, wherein the carcinoma is breast cancer.
4. The method of claim 2, wherein the carcinoma is pancreatic cancer.
5. The method of claim 2, wherein the carcinoma is colorectal cancer.
6. The method of claim 2, wherein the carcinoma is bladder cancer.
7. The method of claim 2, wherein the carcinoma is lung cancer.
8. The method of claim 7, wherein the lung cancer is a non-small cell lung cancer.
9. The method of claim 7, wherein the lung cancer is a large cell lung cancer.
10. The method of claim 2, wherein the carcinoma is prostate cancer.
11. The method of claim 2, wherein the carcinoma is ovarian cancer.
12. The method of claim 2, wherein the carcinoma is bile duct cancer.
13. The method of claim 1, wherein ibrutinib and abexinostat are administered in a unified dosage form or separate dosage forms.
14. The method of claim 1, wherein ibrutinib and abexinostat are administered simultaneously or sequentially.
15. A composition comprising a therapeutically effective amount of (R)-1-(3-(4-amino-3-(4-phenoxyphenyl)-1H-pyrazolo[3,4-d]pyrimidin-1-yl)piperidin-1-yl)prop-2-en-1-one

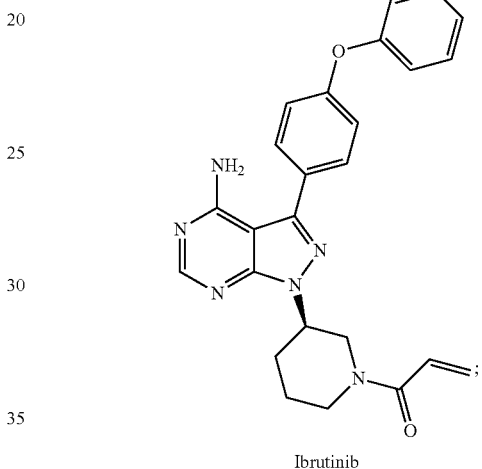

Ibrutinib and a therapeutically effective amount of 3-[(dimethylamino)methyl]-N-{2-[4-(hydroxycarbamoyl)phenoxy]ethyl}-1-benzofuran-2-carboxamide

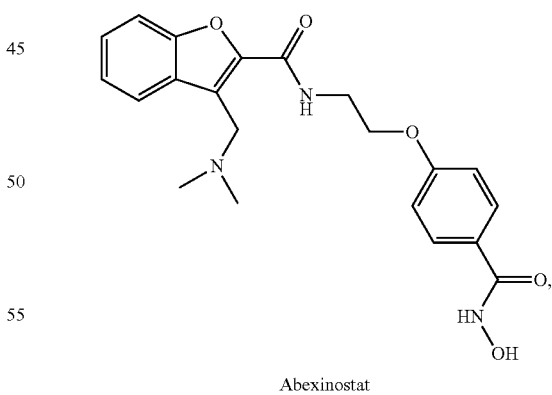

Abexinostat and a pharmaceutically acceptable excipient.

* * * * *